(12) United States Patent
Shenoy et al.

(10) Patent No.: US 11,730,519 B2
(45) Date of Patent: Aug. 22, 2023

(54) METHOD AND APPARATUS FOR FORCE REDISTRIBUTION IN ARTICULAR JOINTS

(71) Applicant: The Foundry, LLC, Menlo Park, CA (US)

(72) Inventors: Vivek Shenoy, Redwood City, CA (US); Mark Deem, Mountain View, CA (US); Hanson S. Gifford, III, Woodside, CA (US)

(73) Assignee: The Foundry, LLC, Menlo Park, CA (US)

( * ) Notice: Subject to any disclaimer, the term of this patent is extended or adjusted under 35 U.S.C. 154(b) by 1000 days.

(21) Appl. No.: 15/790,619

(22) Filed: Oct. 23, 2017

(65) Prior Publication Data
US 2018/0055541 A1 Mar. 1, 2018

Related U.S. Application Data

(63) Continuation of application No. 13/002,829, filed as application No. PCT/US2010/046996 on Aug. 27, 2010, now Pat. No. 9,795,410.

(60) Provisional application No. 61/237,518, filed on Aug. 27, 2009, provisional application No. 61/288,692, filed on Dec. 21, 2009.

(51) Int. Cl.
*A61B 17/02* (2006.01)
*A61B 17/34* (2006.01)
*A61F 2/00* (2006.01)
*A61B 17/56* (2006.01)
(Continued)

(52) U.S. Cl.
CPC ............... *A61B 17/56* (2013.01); *A61F 2/32* (2013.01); *A61B 2017/564* (2013.01); *A61B 2017/565* (2013.01); *A61F 2002/30688* (2013.01)

(58) Field of Classification Search
CPC .............. A61B 17/025; A61B 17/7055; A61B 17/1739; A61B 17/1668; A61B 17/1746; A61B 17/56; A61B 17/175; A61B 17/0401; A61B 17/151; A61B 17/155;
(Continued)

(56) References Cited

U.S. PATENT DOCUMENTS 2,632,440 A 3/1953 Hauser
2,877,033 A 3/1959 Koetke
(Continued)

FOREIGN PATENT DOCUMENTS

CA 1205602 6/1986
CN 2788765 6/2006
(Continued)

OTHER PUBLICATIONS

PCT International Search Report and Written Opinion dated Oct. 20, 2010, for related application PCT/US2010/046996 filed Aug. 27, 2010 entitled "Method and Apparatus for Force Redistribution in Articular Joints"; Vivek Shenoy, Mark Deem and Hanson Gifford.
(Continued)

*Primary Examiner* — Ann Schillinger
(74) *Attorney, Agent, or Firm* — Downs Rachlin Martin PLLC

(57) ABSTRACT

Pathologies of joints arising from improper force distributions are addressed by displacement of targeted connective and muscle tissues surrounding the joint in order to realign force vectors and alter moment arms loading the joint.

8 Claims, 32 Drawing Sheets

(51) Int. Cl.
*A61F 2/32* (2006.01)
*A61F 2/30* (2006.01)

(58) Field of Classification Search
CPC ........ A61B 2017/0464; A61B 17/1742; A61B 17/68; A61B 5/4528; A61B 17/1664
See application file for complete search history.

(56) References Cited

U.S. PATENT DOCUMENTS

| | | |
|---|---|---|
| 3,242,922 A | 3/1966 | Thomas |
| 3,648,294 A | 3/1972 | Shahrestani |
| 3,681,786 A | 8/1972 | Lynch |
| 3,779,654 A | 12/1973 | Horne |
| 3,872,519 A | 3/1975 | Giannestras et al. |
| 3,875,594 A | 4/1975 | Lynch |
| 3,879,767 A | 4/1975 | Stubstad |
| 3,886,599 A | 6/1975 | Schlien |
| 3,889,300 A | 6/1975 | Smith |
| 3,902,482 A | 9/1975 | Taylor |
| 3,964,106 A | 6/1976 | Hutter, Jr. et al. |
| 3,985,127 A | 10/1976 | Volkov et al. |
| 3,988,783 A | 11/1976 | Treace |
| 4,007,495 A | 2/1977 | Frazier |
| 4,041,550 A | 8/1977 | Frazier |
| 4,052,753 A | 10/1977 | Dedo |
| 4,054,955 A | 10/1977 | Seppo |
| 4,069,518 A | 1/1978 | Groth, Jr. et al. |
| 4,156,944 A | 6/1979 | Schreiber et al. |
| 4,158,894 A | 6/1979 | Worrell |
| 4,164,793 A | 8/1979 | Swanson |
| 4,187,841 A | 2/1980 | Knutson |
| 4,246,660 A | 1/1981 | Wevers |
| 4,285,070 A | 8/1981 | Averill |
| 4,308,863 A | 1/1982 | Fischer |
| 4,353,361 A | 10/1982 | Foster |
| 4,367,562 A | 1/1983 | Gauthier |
| 4,470,158 A | 9/1984 | Pappas et al. |
| 4,501,266 A | 2/1985 | McDaniel |
| 4,570,625 A | 2/1986 | Harris |
| 4,576,158 A | 3/1986 | Boland |
| 4,621,627 A | 11/1986 | DeBastiani et al. |
| 4,637,382 A | 1/1987 | Walker |
| 4,642,122 A | 2/1987 | Steffee |
| 4,696,293 A | 9/1987 | Ciullo |
| 4,759,765 A | 7/1988 | Van Kampen |
| 4,759,766 A | 7/1988 | Buettner-Janz et al. |
| 4,776,851 A | 10/1988 | Bruchman et al. |
| 4,778,472 A | 10/1988 | Homsy et al. |
| 4,846,842 A | 7/1989 | Connolly et al. |
| 4,863,471 A | 9/1989 | Mansat |
| 4,871,367 A | 10/1989 | Christensen et al. |
| 4,873,967 A | 10/1989 | Sutherland |
| 4,883,486 A | 11/1989 | Kapadia et al. |
| 4,904,261 A | 2/1990 | Dove et al. |
| 4,919,672 A | 4/1990 | Millar et al. |
| 4,923,471 A | 5/1990 | Morgan |
| 4,942,875 A | 7/1990 | Hlavacek et al. |
| 4,955,915 A | 9/1990 | Swanson |
| 4,959,065 A | 9/1990 | Arnett et al. |
| 4,988,349 A | 1/1991 | Pennig |
| 4,988,350 A | 1/1991 | Herzberg |
| 5,002,574 A | 3/1991 | May et al. |
| 5,011,497 A | 4/1991 | Persson et al. |
| 5,019,077 A | 5/1991 | DeBastiani et al. |
| 5,019,104 A | 5/1991 | Whiteside et al. |
| 5,026,372 A | 6/1991 | Sturtzkopf et al. |
| 5,035,700 A | 7/1991 | Kenna |
| 5,041,112 A | 8/1991 | Mingozzi et al. |
| 5,100,403 A | 3/1992 | Hotchkiss et al. |
| 5,103,811 A | 4/1992 | Crupi |
| 5,121,742 A | 6/1992 | Engen |
| 5,152,280 A | 10/1992 | Danieli |
| 5,152,790 A | 10/1992 | Rosenberg et al. |
| 5,197,966 A | 3/1993 | Sommerkamp |
| 5,197,986 A | 3/1993 | Mikhail |
| 5,231,977 A | 8/1993 | Graston |
| 5,258,032 A | 11/1993 | Bertin |
| 5,304,180 A | 4/1994 | Slocum |
| 5,314,481 A | 5/1994 | Bianco |
| 5,318,567 A | 6/1994 | Vichard |
| 5,326,364 A | 6/1994 | Clift, Jr. et al. |
| 5,352,190 A | 10/1994 | Fischer |
| 5,375,823 A | 12/1994 | Navas |
| 5,383,937 A | 1/1995 | Mikhail |
| 5,405,347 A | 4/1995 | Lee et al. |
| 5,415,661 A | 5/1995 | Holmes |
| 5,425,775 A | 6/1995 | Kovacevic et al. |
| 5,456,722 A | 10/1995 | McLeod et al. |
| 5,480,443 A | 1/1996 | Elias |
| 5,540,688 A | 7/1996 | Navas |
| 5,545,229 A | 8/1996 | Parsons et al. |
| 5,571,198 A | 11/1996 | Drucker et al. |
| 5,575,819 A | 11/1996 | Amis |
| 5,578,038 A | 11/1996 | Slocum |
| 5,580,353 A | 12/1996 | Mendes et al. |
| 5,601,553 A | 2/1997 | Trebling et al. |
| 5,624,440 A | 4/1997 | Huebner |
| 5,662,648 A | 9/1997 | Faccioli et al. |
| 5,662,650 A | 9/1997 | Bailey et al. |
| 5,676,667 A | 10/1997 | Hausman |
| 5,681,313 A | 10/1997 | Diez |
| 5,695,496 A | 12/1997 | Orsak et al. |
| 5,702,460 A | 12/1997 | Carls et al. |
| 5,702,465 A | 12/1997 | Burkinshaw |
| 5,702,467 A | 12/1997 | Gabriel et al. |
| 5,716,357 A | 2/1998 | Rogozinski |
| 5,733,287 A | 3/1998 | Tepic et al. |
| 5,749,872 A | 5/1998 | Kyle et al. |
| 5,766,251 A | 6/1998 | Koshino |
| 5,803,924 A | 9/1998 | Oni et al. |
| 5,824,106 A | 10/1998 | Fournol |
| 5,871,540 A | 2/1999 | Weissman et al. |
| 5,873,843 A | 2/1999 | Draper |
| 5,879,386 A | 3/1999 | Jore |
| 5,888,203 A | 3/1999 | Goldberg |
| 5,928,234 A | 7/1999 | Manspeizer |
| 5,944,757 A | 8/1999 | Grammont |
| 5,976,125 A | 11/1999 | Graham |
| 5,976,136 A | 11/1999 | Bailey et al. |
| 5,989,292 A | 11/1999 | van Loon |
| 6,036,691 A | 3/2000 | Richardson |
| 6,096,040 A | 8/2000 | Esser |
| 6,113,637 A | 9/2000 | Gill et al. |
| 6,132,468 A | 10/2000 | Mansmann |
| 6,139,550 A | 10/2000 | Michelson |
| 6,143,032 A | 11/2000 | Schafer et al. |
| 6,146,423 A | 11/2000 | Cohen et al. |
| 6,161,080 A | 12/2000 | Aouni-Ateshian et al. |
| 6,162,223 A | 12/2000 | Orsak et al. |
| 6,176,860 B1 | 1/2001 | Howard |
| 6,193,225 B1 | 2/2001 | Watanabe |
| 6,200,347 B1 | 3/2001 | Anderson et al. |
| D443,060 S | 5/2001 | Benirschke et al. |
| 6,245,110 B1 | 6/2001 | Grundei et al. |
| 6,264,696 B1 | 7/2001 | Reigner et al. |
| 6,277,124 B1 | 8/2001 | Haag |
| 6,280,474 B1 | 8/2001 | Cassidy et al. |
| 6,302,915 B1 | 10/2001 | Cooney, III et al. |
| 6,315,798 B1 | 11/2001 | Ashby et al. |
| 6,315,852 B1 | 11/2001 | Magrini et al. |
| 6,355,037 B1 | 3/2002 | Crosslin et al. |
| 6,364,881 B1 | 4/2002 | Apgar et al. |
| 6,368,326 B1 | 4/2002 | Dakin et al. |
| 6,371,985 B1 | 4/2002 | Goldberg |
| 6,409,729 B1 | 6/2002 | Martinelli et al. |
| 6,409,767 B1 | 6/2002 | Perice et al. |
| 6,468,314 B2 | 10/2002 | Schwartz et al. |
| 6,482,232 B1 | 11/2002 | Boucher et al. |
| 6,485,503 B2 | 11/2002 | Jacobs et al. |
| 6,494,914 B2 | 12/2002 | Brown et al. |
| 6,520,964 B2 | 2/2003 | Tallarida et al. |
| 6,527,733 B1 | 3/2003 | Ceriani et al. |
| 6,540,708 B1 | 4/2003 | Manspeizer |
| 6,572,653 B1 | 6/2003 | Simonson |

(56) References Cited

U.S. PATENT DOCUMENTS

| | | |
|---|---|---|
| 6,579,318 B2 | 6/2003 | Varga et al. |
| 6,589,248 B1 | 7/2003 | Hughes |
| 6,592,622 B1 | 7/2003 | Ferguson |
| 6,599,321 B2 | 7/2003 | Hyde, Jr. |
| 6,599,322 B1 | 7/2003 | Amrich et al. |
| 6,616,696 B1 | 9/2003 | Merchant |
| 6,620,332 B2 | 9/2003 | Amrich |
| 6,623,486 B1 | 9/2003 | Weaver et al. |
| 6,626,945 B2 | 9/2003 | Simon et al. |
| 6,632,247 B2 | 10/2003 | Boyer, II et al. |
| 6,652,529 B2 | 11/2003 | Swanson |
| 6,663,631 B2 | 12/2003 | Kuntz |
| 6,679,914 B1 | 1/2004 | Gabbay |
| 6,692,497 B1 | 2/2004 | Tormala et al. |
| 6,692,498 B1 | 2/2004 | Niiranen et al. |
| 6,702,821 B2 | 3/2004 | Bonutti |
| 6,709,460 B2 | 3/2004 | Merchant |
| 6,712,856 B1 | 3/2004 | Carignan et al. |
| 6,719,794 B2 | 4/2004 | Gerber |
| 6,752,831 B2 | 6/2004 | Sybert et al. |
| 6,770,078 B2 | 8/2004 | Bonutti |
| 6,800,094 B2 | 10/2004 | Burkinshaw |
| 6,814,757 B2 | 11/2004 | Kopylov et al. |
| 6,824,567 B2 | 11/2004 | Tornier et al. |
| 6,852,125 B2 | 2/2005 | Simon et al. |
| 6,852,330 B2 | 2/2005 | Bowman et al. |
| 6,854,330 B2 | 2/2005 | Potter |
| 6,855,150 B1 | 2/2005 | Linchan |
| 6,866,684 B2 | 3/2005 | Fell et al. |
| 6,884,242 B2 | 4/2005 | LeHuec et al. |
| 6,890,358 B2 | 5/2005 | Ball et al. |
| 6,893,463 B2 | 5/2005 | Fell et al. |
| 6,896,702 B2 | 5/2005 | Collazo |
| 6,905,513 B1 | 6/2005 | Metzger |
| 6,911,044 B2 | 6/2005 | Fell et al. |
| 6,916,341 B2 | 7/2005 | Rolston |
| 6,926,739 B1 | 8/2005 | O'Connor et al. |
| 6,966,910 B2 | 11/2005 | Ritland |
| 6,966,928 B2 | 11/2005 | Fell et al. |
| 6,972,020 B1 | 12/2005 | Grayson et al. |
| 6,974,480 B2 | 12/2005 | Messerli et al. |
| 6,994,730 B2 | 2/2006 | Posner |
| 6,997,940 B2 | 2/2006 | Bonutti |
| 7,004,971 B2 | 2/2006 | Serhan et al. |
| 7,008,452 B2 | 3/2006 | Hawkins |
| 7,011,687 B2 | 3/2006 | Deffenbaugh et al. |
| 7,018,418 B2 | 3/2006 | Amrich et al. |
| 7,025,790 B2 | 4/2006 | Parks et al. |
| 7,029,475 B2 | 4/2006 | Pajabi |
| 7,060,073 B2 | 6/2006 | Frey et al. |
| 7,105,025 B2 | 9/2006 | Castro et al. |
| 7,105,027 B2 | 9/2006 | Lipman et al. |
| 7,124,762 B2 | 10/2006 | Carter et al. |
| 7,128,744 B2 | 10/2006 | Weaver et al. |
| 7,141,073 B2 | 11/2006 | May et al. |
| 7,160,333 B2 | 1/2007 | Plouhar et al. |
| 7,163,563 B2 | 1/2007 | Schwartz et al. |
| 7,182,787 B2 | 2/2007 | Hassler et al. |
| 7,188,626 B2 | 3/2007 | Foley et al. |
| 7,201,728 B2 | 4/2007 | Sterling |
| 7,223,292 B2 | 5/2007 | Messerli et al. |
| 7,226,482 B2 | 6/2007 | Messerli et al. |
| 7,226,483 B2 | 6/2007 | Gerber et al. |
| 7,235,077 B1 | 6/2007 | Wang et al. |
| 7,235,102 B2 | 6/2007 | Ferree et al. |
| 7,238,203 B2 | 7/2007 | Bagga et al. |
| 7,241,298 B2 | 7/2007 | Nemec et al. |
| 7,247,157 B2 | 7/2007 | Prager et al. |
| 7,252,670 B2 | 8/2007 | Morrison et al. |
| 7,261,739 B2 | 8/2007 | Ralph et al. |
| 7,273,481 B2 | 9/2007 | Lombardo et al. |
| 7,276,070 B2 | 10/2007 | Muckter |
| 7,282,065 B2 | 10/2007 | Kirschman |
| 7,285,134 B2 | 10/2007 | Berry et al. |
| 7,288,094 B2 | 10/2007 | Lindemann et al. |
| 7,288,095 B2 | 10/2007 | Baynham et al. |
| 7,291,150 B2 | 11/2007 | Graf |
| 7,291,169 B2 | 11/2007 | Hodorek |
| 7,297,161 B2 | 11/2007 | Fell |
| 7,306,605 B2 | 12/2007 | Ross |
| 7,322,983 B2 | 1/2008 | Harris |
| 7,322,984 B2 | 1/2008 | Doubler et al. |
| 7,323,012 B1 | 1/2008 | Stone et al. |
| 7,341,589 B2 | 3/2008 | Weaver et al. |
| 7,341,590 B2 | 3/2008 | Ferree |
| 7,341,602 B2 | 3/2008 | Fell et al. |
| 7,361,196 B2 | 4/2008 | Fallin et al. |
| 7,476,225 B2 | 1/2009 | Cole |
| 7,479,160 B2 | 1/2009 | Branch et al. |
| 7,485,147 B2 | 2/2009 | Pappas et al. |
| 7,500,991 B2 | 3/2009 | Bartish, Jr. et al. |
| 7,534,270 B2 | 5/2009 | Ball |
| 7,544,210 B2 | 6/2009 | Schaefer et al. |
| 7,553,331 B2 | 6/2009 | Manspeizer |
| 7,572,291 B2 | 8/2009 | Gil et al. |
| 7,611,540 B2 | 11/2009 | Clifford et al. |
| 7,618,454 B2 | 11/2009 | Bentley et al. |
| 7,632,310 B2 | 12/2009 | Clifford et al. |
| 7,632,311 B2 | 12/2009 | Seedhom et al. |
| 7,637,953 B2 | 12/2009 | Branch et al. |
| 7,641,689 B2 | 1/2010 | Fell et al. |
| 7,655,029 B2 | 2/2010 | Niederberger et al. |
| 7,655,041 B2 | 2/2010 | Clifford et al. |
| 7,678,147 B2 | 3/2010 | Clifford et al. |
| 7,722,676 B2 | 5/2010 | Hanson et al. |
| 7,723,395 B2 | 5/2010 | Ringeisen et al. |
| 7,726,319 B1 | 6/2010 | Boyce |
| 7,744,638 B2 | 6/2010 | Orbay |
| 7,749,276 B2 | 7/2010 | Fitz |
| 7,758,651 B2 | 7/2010 | Chauhan et al. |
| 7,780,670 B2 | 8/2010 | Bonutti |
| 7,806,898 B2 | 10/2010 | Justin et al. |
| 7,819,918 B2 | 10/2010 | Malaviya et al. |
| 7,828,852 B2 | 11/2010 | Bonutti |
| 7,846,211 B2 | 12/2010 | Clifford et al. |
| 7,875,082 B2 | 1/2011 | Naidu |
| 7,879,105 B2 | 2/2011 | Schmieding et al. |
| 7,896,921 B2 | 3/2011 | Smith et al. |
| 7,896,923 B2 | 3/2011 | Blackwell et al. |
| 7,951,176 B2 | 5/2011 | Grady et al. |
| 7,959,675 B2 | 6/2011 | Gately |
| 7,967,863 B2 | 6/2011 | Frey et al. |
| 7,972,383 B2 | 7/2011 | Goldstein et al. |
| 7,993,402 B2 | 8/2011 | Sidler |
| 8,002,833 B2 | 8/2011 | Fabris Monterumici et al. |
| 8,002,837 B2 | 8/2011 | Stream et al. |
| 8,002,841 B2 | 8/2011 | Hasselman |
| 8,034,117 B2 | 10/2011 | Matsuzaki et al. |
| 8,043,375 B2 | 10/2011 | Strzepa et al. |
| 8,043,380 B1 | 10/2011 | Park et al. |
| 8,052,753 B2 | 11/2011 | Melvin |
| 8,052,755 B2 | 11/2011 | Naidu |
| 8,083,746 B2 | 12/2011 | Novak |
| 8,088,166 B2 | 1/2012 | Makower et al. |
| 8,088,168 B2 | 1/2012 | Hassler et al. |
| 8,092,530 B2 | 1/2012 | Strzepa et al. |
| 8,092,544 B2 | 1/2012 | Wright et al. |
| 8,100,967 B2 | 1/2012 | Makower et al. |
| 8,114,156 B2 | 2/2012 | Hatch |
| 8,123,805 B2 | 2/2012 | Makower et al. |
| 8,128,697 B2 | 3/2012 | Fell et al. |
| 8,128,704 B2 | 3/2012 | Brown et al. |
| 8,142,503 B2 | 3/2012 | Malone |
| 8,257,444 B2 | 9/2012 | Linares |
| 8,262,707 B2 | 9/2012 | Huebner et al. |
| 8,267,972 B1 | 9/2012 | Gehlert |
| 8,282,681 B2 | 10/2012 | McLeod |
| 8,292,955 B2 | 10/2012 | Robinson |
| 8,328,805 B2 | 12/2012 | Cole |
| 8,372,078 B2 | 2/2013 | Collazo |
| 8,382,807 B2 | 2/2013 | Austin et al. |
| 8,523,921 B2 | 9/2013 | Horan et al. |
| 8,523,948 B2 | 9/2013 | Slone et al. |
| 8,597,362 B2 | 12/2013 | Shenoy et al. |

(56) References Cited

U.S. PATENT DOCUMENTS

| | | |
|---|---|---|
| 8,771,363 B2 | 7/2014 | Grotz |
| 8,845,724 B2 | 9/2014 | Shenoy et al. |
| 8,986,311 B2 | 3/2015 | Boudreault |
| 9,114,016 B2 | 8/2015 | Shenoy |
| 9,216,091 B2 | 12/2015 | Hardy |
| 9,278,004 B2 | 3/2016 | Shenoy |
| 9,668,868 B2 | 6/2017 | Shenoy |
| 9,795,410 B2 | 10/2017 | Shenoy |
| 9,861,408 B2 | 1/2018 | Shenoy |
| 9,931,136 B2 | 4/2018 | Shenoy |
| 10,299,939 B2 | 5/2019 | Gonzalez-Hernandez |
| 10,349,980 B2 | 7/2019 | Shenoy |
| 2001/0020143 A1 | 9/2001 | Stark et al. |
| 2001/0023371 A1 | 9/2001 | Bonutti |
| 2001/0037155 A1 | 11/2001 | Merchant |
| 2002/0013587 A1 | 1/2002 | Winquist et al. |
| 2002/0029045 A1 | 3/2002 | Bonutti |
| 2002/0029084 A1 | 3/2002 | Paul et al. |
| 2002/0052606 A1 | 5/2002 | Bonutti |
| 2002/0065560 A1 | 5/2002 | Varga et al. |
| 2002/0091447 A1 | 7/2002 | Shimp et al. |
| 2002/0095154 A1 | 7/2002 | Atkinson et al. |
| 2002/0107574 A1 | 8/2002 | Boehm et al. |
| 2002/0133230 A1 | 9/2002 | Repicci |
| 2002/0151978 A1 | 10/2002 | Zacouto et al. |
| 2002/0165550 A1 | 11/2002 | Frey et al. |
| 2003/0055500 A1 | 3/2003 | Fell et al. |
| 2003/0083751 A1 | 5/2003 | Tornier |
| 2003/0088315 A1 | 5/2003 | Supinski |
| 2003/0100950 A1 | 5/2003 | Moret |
| 2003/0109928 A1 | 6/2003 | Pasquet et al. |
| 2003/0120344 A1 | 6/2003 | Michelson |
| 2003/0120346 A1 | 6/2003 | Mercinek et al. |
| 2003/0125807 A1 | 7/2003 | Lambrecht et al. |
| 2003/0139813 A1 | 7/2003 | Messerli et al. |
| 2003/0204265 A1 | 10/2003 | Short et al. |
| 2003/0216809 A1 | 11/2003 | Ferguson |
| 2004/0054409 A1 | 3/2004 | Harris |
| 2004/0117020 A1 | 6/2004 | Frey et al. |
| 2004/0127990 A1 | 7/2004 | Bartish, Jr. et al. |
| 2004/0133278 A1 | 7/2004 | Marino et al. |
| 2004/0143336 A1 | 7/2004 | Burkinshaw |
| 2004/0143338 A1 | 7/2004 | Burkinshaw |
| 2004/0148026 A1 | 7/2004 | Bonutti |
| 2004/0167630 A1 | 8/2004 | Rolston |
| 2004/0172133 A1 | 9/2004 | Gerber et al. |
| 2004/0186585 A1 | 9/2004 | Feiwell |
| 2004/0215195 A1 | 10/2004 | Shipp et al. |
| 2004/0230303 A1 | 11/2004 | Gomes et al. |
| 2004/0230315 A1 | 11/2004 | Ek |
| 2004/0236428 A1 | 11/2004 | Burkinshaw et al. |
| 2004/0243240 A1 | 12/2004 | Beaurain et al. |
| 2004/0260302 A1 | 12/2004 | Manspeizer |
| 2004/0267179 A1 | 12/2004 | Leman |
| 2004/0267375 A1 | 12/2004 | Friedrichs |
| 2005/0004671 A1 | 1/2005 | Ross et al. |
| 2005/0027360 A1 | 2/2005 | Webb et al. |
| 2005/0033424 A1 | 2/2005 | Fell |
| 2005/0033426 A1 | 2/2005 | Ogilvie et al. |
| 2005/0043808 A1 | 2/2005 | Felt et al. |
| 2005/0049708 A1 | 3/2005 | Atkinson et al. |
| 2005/0049711 A1 | 3/2005 | Ball |
| 2005/0085815 A1 | 4/2005 | Harms et al. |
| 2005/0119664 A1 | 6/2005 | Carignan et al. |
| 2005/0119744 A1 | 6/2005 | Buskirk et al. |
| 2005/0137708 A1 | 6/2005 | Clark |
| 2005/0143822 A1 | 6/2005 | Paul |
| 2005/0143830 A1 | 6/2005 | Marcinek et al. |
| 2005/0154390 A1 | 7/2005 | Biedermann et al. |
| 2005/0192674 A1 | 9/2005 | Ferree |
| 2005/0222685 A1 | 10/2005 | Hayden et al. |
| 2005/0251080 A1 | 11/2005 | Hyde, Jr. |
| 2005/0261680 A1 | 11/2005 | Draper |
| 2005/0261767 A1 | 11/2005 | Anderson et al. |
| 2005/0267584 A1 | 12/2005 | Burdulis, Jr. et al. |
| 2005/0273114 A1 | 12/2005 | Novak |
| 2005/0288788 A1 | 12/2005 | Dougherty-Shah |
| 2006/0036321 A1 | 2/2006 | Henninger et al. |
| 2006/0064169 A1 | 3/2006 | Ferree |
| 2006/0074492 A1 | 4/2006 | Frey |
| 2006/0085069 A1 | 4/2006 | Kim |
| 2006/0100715 A1 | 5/2006 | De Villiers |
| 2006/0106460 A1 | 5/2006 | Messerli et al. |
| 2006/0122620 A1 | 6/2006 | Kim |
| 2006/0129243 A1 | 6/2006 | Wong et al. |
| 2006/0142858 A1 | 6/2006 | Colleran et al. |
| 2006/0149274 A1 | 7/2006 | Justin et al. |
| 2006/0161260 A1 | 7/2006 | Thomas et al. |
| 2006/0074423 A1 | 8/2006 | Alleyne |
| 2006/0178744 A1 | 8/2006 | de Villiers et al. |
| 2006/0235387 A1 | 10/2006 | Peterman |
| 2006/0276907 A1 | 12/2006 | Boyer, II et al. |
| 2007/0027547 A1 | 2/2007 | Rydell et al. |
| 2007/0043356 A1 | 2/2007 | Timm et al. |
| 2007/0106299 A1 | 5/2007 | Manspeizer |
| 2007/0129804 A1 | 6/2007 | Bentley et al. |
| 2007/0129809 A1 | 6/2007 | Meridew et al. |
| 2007/0173946 A1 | 6/2007 | Bonutti |
| 2007/0161993 A1 | 7/2007 | Lowery et al. |
| 2007/0168033 A1 | 7/2007 | Kim et al. |
| 2007/0168036 A1 | 7/2007 | Ainsworth et al. |
| 2007/0198088 A1 | 8/2007 | Biedermann et al. |
| 2007/0198091 A1 | 8/2007 | Boyer et al. |
| 2007/0203581 A1 | 8/2007 | Vanaclocha |
| 2007/0208343 A1 | 9/2007 | Magerl et al. |
| 2007/0225820 A1 | 9/2007 | Thomas et al. |
| 2007/0233141 A1 | 10/2007 | Park et al. |
| 2007/0244483 A9 | 10/2007 | Winslow et al. |
| 2007/0244488 A1 | 10/2007 | Metzger et al. |
| 2007/0265708 A1 | 11/2007 | Brown et al. |
| 2007/0276491 A1 | 11/2007 | Ahrens |
| 2007/0288014 A1 | 12/2007 | Shadduck et al. |
| 2007/0293947 A1 | 12/2007 | Mansmann |
| 2007/0299528 A9 | 12/2007 | Lotke |
| 2008/0015591 A1 | 1/2008 | Castaneda et al. |
| 2008/0015592 A1 | 1/2008 | Long et al. |
| 2008/0015593 A1 | 1/2008 | Pfefferie et al. |
| 2008/0015603 A1 | 1/2008 | Collazo |
| 2008/0015604 A1 | 1/2008 | Collazo |
| 2008/0021566 A1 | 1/2008 | Peters et al. |
| 2008/0033552 A1 | 2/2008 | Lee et al. |
| 2008/0044449 A1 | 2/2008 | McKay |
| 2008/0071373 A1 | 3/2008 | Molz et al. |
| 2008/0071375 A1 | 3/2008 | Carver et al. |
| 2008/0091270 A1 | 4/2008 | Millet et al. |
| 2008/0097434 A1 | 4/2008 | Moumene et al. |
| 2008/0097441 A1 | 4/2008 | Hayes et al. |
| 2008/0097617 A1 | 4/2008 | Fellinger et al. |
| 2008/0132954 A1 | 6/2008 | Sekhon et al. |
| 2008/0140094 A1 | 6/2008 | Schwartz et al. |
| 2008/0140213 A1 | 6/2008 | Ammann et al. |
| 2008/0154311 A1 | 6/2008 | Staeubli |
| 2008/0154371 A1 | 6/2008 | Fell et al. |
| 2008/0154378 A1 | 6/2008 | Pelo |
| 2008/0161815 A1 | 7/2008 | Schoenefeld et al. |
| 2008/0161933 A1 | 7/2008 | Grotz et al. |
| 2008/0195099 A1 | 8/2008 | Minas |
| 2008/0200995 A1 | 8/2008 | Sidebotham |
| 2008/0208341 A1 | 8/2008 | McCormack |
| 2008/0208346 A1 | 8/2008 | Schwartz |
| 2008/0234686 A1 | 9/2008 | Beaurain et al. |
| 2008/0262549 A1 | 10/2008 | Bennett et al. |
| 2008/0262618 A1 | 10/2008 | Hermsen et al. |
| 2008/0275509 A1 | 11/2008 | Clifford et al. |
| 2008/0275552 A1 | 11/2008 | Makower et al. |
| 2008/0275555 A1 | 11/2008 | Makower et al. |
| 2008/0275556 A1 | 11/2008 | Makower et al. |
| 2008/0275557 A1 | 11/2008 | Makower et al. |
| 2008/0275558 A1 | 11/2008 | Clifford et al. |
| 2008/0275559 A1 | 11/2008 | Makower et al. |
| 2008/0275560 A1 | 11/2008 | Clifford et al. |
| 2008/0275561 A1 | 11/2008 | Clifford et al. |
| 2008/0275562 A1 | 11/2008 | Clifford et al. |
| 2008/0275563 A1 | 11/2008 | Makower et al. |

(56) References Cited

U.S. PATENT DOCUMENTS

| | | |
|---|---|---|
| 2008/0275564 A1 | 11/2008 | Makower et al. |
| 2008/0275565 A1 | 11/2008 | Makower et al. |
| 2008/0275567 A1 | 11/2008 | Makower et al. |
| 2008/0275571 A1 | 11/2008 | Clifford et al. |
| 2008/0281422 A1 | 11/2008 | Schmieding |
| 2008/0281425 A1 | 11/2008 | Thalgott et al. |
| 2009/0012615 A1 | 1/2009 | Fell |
| 2009/0014016 A1 | 1/2009 | Clifford et al. |
| 2009/0018656 A1 | 1/2009 | Clifford et al. |
| 2009/0018665 A1 | 1/2009 | Clifford et al. |
| 2009/0036893 A1 | 2/2009 | Kartalian et al. |
| 2009/0048683 A1 | 2/2009 | Morris et al. |
| 2009/0076605 A1 | 3/2009 | Linares |
| 2009/0082808 A1 | 3/2009 | Butler |
| 2009/0088763 A1 | 4/2009 | Aram et al. |
| 2009/0088846 A1 | 4/2009 | Myung et al. |
| 2009/0112268 A1 | 4/2009 | Cole |
| 2009/0118830 A1 | 5/2009 | Fell |
| 2009/0132047 A1 | 5/2009 | Mansmann |
| 2009/0164014 A1 | 6/2009 | Liljensten et al. |
| 2009/0182433 A1 | 7/2009 | Reiley et al. |
| 2009/0187252 A1 | 7/2009 | Howald |
| 2009/0198341 A1 | 8/2009 | Choi et al. |
| 2009/0210063 A1 | 8/2009 | Barrett |
| 2009/0226068 A1 | 9/2009 | Fitz et al. |
| 2009/0248026 A1 | 10/2009 | Draper |
| 2009/0259311 A1 | 10/2009 | Shterling et al. |
| 2009/0259312 A1 | 10/2009 | Shterling et al. |
| 2009/0275945 A1 | 11/2009 | Makower |
| 2009/0306783 A1 | 12/2009 | Blum |
| 2009/0312807 A1 | 12/2009 | Boudreault et al. |
| 2009/0318924 A1 | 12/2009 | Helenbolt et al. |
| 2009/0318976 A1 | 12/2009 | Gabriel et al. |
| 2010/0023126 A1 | 1/2010 | Grotz |
| 2010/0023127 A1 | 1/2010 | Shohat |
| 2010/0049322 A1 | 2/2010 | McKay |
| 2010/0049325 A1 | 2/2010 | Biedermann et al. |
| 2010/0057216 A1 | 3/2010 | Gannoe et al. |
| 2010/0076564 A1 | 3/2010 | Schilling et al. |
| 2010/0106247 A1 | 4/2010 | Makower et al. |
| 2010/0106248 A1 | 4/2010 | Makower et al. |
| 2010/0114322 A1 | 5/2010 | Clifford et al. |
| 2010/0121355 A1 | 5/2010 | Gittings et al. |
| 2010/0121457 A1 | 5/2010 | Clifford et al. |
| 2010/0125266 A1 | 5/2010 | Deem et al. |
| 2010/0131068 A1 | 5/2010 | Brown et al. |
| 2010/0131069 A1 | 5/2010 | Halbrecht |
| 2010/0137996 A1 | 6/2010 | Clifford et al. |
| 2010/0145449 A1 | 6/2010 | Makower et al. |
| 2010/0161057 A1 | 6/2010 | Berry et al. |
| 2010/0168857 A1 | 7/2010 | Hatch |
| 2010/0198354 A1 | 8/2010 | Halbrecht |
| 2010/0204798 A1 | 8/2010 | Gerbec et al. |
| 2010/0262246 A1 | 10/2010 | Attia |
| 2010/0292731 A1 | 11/2010 | Gittings et al. |
| 2010/0292733 A1 | 11/2010 | Hendricksen et al. |
| 2010/0305698 A1 | 12/2010 | Metzger et al. |
| 2010/0305708 A1 | 12/2010 | Lang et al. |
| 2011/0004305 A1 | 1/2011 | Jansson et al. |
| 2011/0054627 A1 | 3/2011 | Bear |
| 2011/0060422 A1 | 3/2011 | Makower et al. |
| 2011/0093073 A1 | 4/2011 | Gatt et al. |
| 2011/0093079 A1 | 4/2011 | Slone et al. |
| 2011/0093080 A1 | 4/2011 | Slone et al. |
| 2011/0121457 A1 | 5/2011 | Clevenger et al. |
| 2011/0137415 A1 | 6/2011 | Clifford et al. |
| 2011/0172768 A1 | 7/2011 | Cragg et al. |
| 2011/0178603 A1 | 7/2011 | Long |
| 2011/0202138 A1 | 8/2011 | Shenoy et al. |
| 2011/0213466 A1 | 9/2011 | Shenoy et al. |
| 2011/0224734 A1 | 9/2011 | Schelling |
| 2011/0230919 A1 | 9/2011 | Alleyne |
| 2011/0230972 A1 | 9/2011 | Katrana |
| 2011/0238180 A1 | 9/2011 | Fritz et al. |
| 2011/0245928 A1 | 10/2011 | Landry et al. |
| 2011/0264216 A1 | 10/2011 | Makower et al. |
| 2011/0270393 A1 | 11/2011 | Marvel |
| 2011/0276097 A1 | 11/2011 | Raven, III |
| 2011/0288643 A1 | 11/2011 | Linder-Ganz et al. |
| 2012/0022649 A1 | 1/2012 | Robinson et al. |
| 2012/0022655 A1 | 1/2012 | Clifford |
| 2012/0046754 A1 | 2/2012 | Clifford et al. |
| 2012/0053644 A1 | 3/2012 | Landry et al. |
| 2012/0065640 A1 | 3/2012 | Metzger et al. |
| 2012/0116522 A1 | 5/2012 | Makower et al. |
| 2012/0136449 A1 | 5/2012 | Makower et al. |
| 2012/0179273 A1 | 7/2012 | Clifford et al. |
| 2012/0197410 A1 | 8/2012 | Horan et al. |
| 2012/0221106 A1 | 8/2012 | Makower et al. |
| 2012/0271366 A1 | 10/2012 | Katrana et al. |
| 2012/0290088 A1 | 11/2012 | Amirouche et al. |
| 2013/0013066 A1 | 1/2013 | Landry et al. |
| 2013/0013067 A1 | 1/2013 | Landry et al. |
| 2013/0018479 A1 | 1/2013 | Grotz |
| 2013/0041416 A1 | 2/2013 | Regala et al. |
| 2013/0096629 A1 | 4/2013 | Rollinghoff et al. |
| 2013/0150977 A1 | 6/2013 | Gabriel et al. |
| 2013/0166036 A1 | 6/2013 | De Cortanze et al. |
| 2013/0190886 A1 | 7/2013 | Tepic et al. |
| 2013/0204378 A1 | 8/2013 | Slone et al. |
| 2013/0211521 A1 | 8/2013 | Shenoy et al. |
| 2013/0289728 A1 | 10/2013 | Makower et al. |
| 2013/0304208 A1 | 11/2013 | Clifford et al. |
| 2013/0325123 A1 | 12/2013 | Clifford et al. |
| 2013/0338783 A1 | 12/2013 | Slone et al. |
| 2014/0052266 A1 | 2/2014 | Slone et al. |
| 2014/0128974 A1 | 5/2014 | Bromer |
| 2014/0156004 A1 | 6/2014 | Shenoy et al. |
| 2014/0156005 A1 | 6/2014 | Shenoy et al. |
| 2014/0257292 A1 | 9/2014 | Embleton et al. |
| 2014/0343675 A1 | 11/2014 | Valeeuwen |
| 2014/0371864 A1 | 12/2014 | Shohat |
| 2016/0213402 A1 | 7/2016 | Shenoy |
| 2016/0256286 A1 | 9/2016 | Morris |
| 2017/0027708 A1 | 2/2017 | Shenoy |
| 2018/0206887 A1 | 7/2018 | Shenoy |

FOREIGN PATENT DOCUMENTS

| | | |
|---|---|---|
| DE | 19855254 A1 | 6/2000 |
| EP | 0383419 A1 | 8/1990 |
| EP | 0953317 B1 | 4/2004 |
| EP | 1410769 A2 | 4/2004 |
| EP | 1770302 A1 | 4/2007 |
| EP | 1429675 B1 | 10/2007 |
| EP | 1682020 B1 | 10/2007 |
| EP | 1847228 A1 | 10/2007 |
| EP | 1847229 A2 | 10/2007 |
| EP | 1005290 B1 | 2/2008 |
| EP | 1468655 B1 | 5/2008 |
| EP | 2452641 A1 | 5/2012 |
| FR | 2926456 A1 | 7/2009 |
| GB | 1507953 | 4/1978 |
| GB | 2223406 | 4/1990 |
| GB | 2250919 | 10/1993 |
| JP | 59131348 | 7/1984 |
| JP | 7100159 | 4/1995 |
| JP | 2532346 B2 | 11/1996 |
| JP | 2000503865 | 4/2000 |
| JP | 2001145647 | 5/2001 |
| JP | 2003102744 | 4/2003 |
| JP | 2006280951 | 10/2006 |
| JP | 2007167318 | 7/2007 |
| JP | 2007167319 | 7/2007 |
| JP | 2007170969 | 7/2007 |
| JP | 2011519303 T | 7/2011 |
| NZ | 533300 | 2/2005 |
| RU | 1769868 A1 | 10/1992 |
| RU | 2085148 | 7/1997 |
| RU | 2217105 C2 | 11/2003 |
| RU | 2241400 C2 | 12/2004 |
| SU | 578063 A1 | 10/1977 |
| SU | 578957 A1 | 11/1977 |
| SU | 624613 A1 | 9/1978 |

(56) References Cited

FOREIGN PATENT DOCUMENTS

| | | | |
|---|---|---|---|
| SU | 640740 | A1 | 1/1979 |
| SU | 704605 | A1 | 12/1979 |
| SU | 719612 | A1 | 3/1980 |
| SU | 741872 | A1 | 6/1980 |
| SU | 1186204 | | 10/1985 |
| SU | 1251889 | | 8/1986 |
| SU | 1316666 | A1 | 6/1987 |
| SU | 1588404 | | 8/1990 |
| SU | 1699441 | A1 | 12/1991 |
| WO | WO-8910730 | A1 * | 11/1989 ............... A61F 2/36 |
| WO | 91/07137 | | 5/1991 |
| WO | 94/06364 | A1 | 3/1994 |
| WO | 96/19944 | A1 | 7/1996 |
| WO | 2004019831 | A2 | 3/2004 |
| WO | 2004024037 | A2 | 3/2004 |
| WO | 2006045091 | A2 | 4/2006 |
| WO | 2006049993 | | 5/2006 |
| WO | 2006110578 | A3 | 10/2006 |
| WO | 2007056645 | A2 | 5/2007 |
| WO | 2007090009 | A1 | 8/2007 |
| WO | 2007090015 | A1 | 8/2007 |
| WO | 2007090017 | A1 | 8/2007 |
| WO | 2007106962 | A1 | 9/2007 |
| WO | 2007109132 | A2 | 9/2007 |
| WO | 2007109140 | A2 | 9/2007 |
| WO | 2007109417 | A2 | 9/2007 |
| WO | 2007109436 | A2 | 9/2007 |
| WO | 2007114769 | A1 | 10/2007 |
| WO | 2007117571 | A2 | 10/2007 |
| WO | 2008006098 | A2 | 1/2008 |
| WO | 2009009618 | A1 | 1/2009 |
| WO | 2009018365 | A1 | 2/2009 |
| WO | 2011025959 | A1 | 3/2011 |
| WO | 2012062908 | A1 | 5/2012 |

OTHER PUBLICATIONS

Office Action dated May 17, 2012, in connection with related U.S. Appl. No. 13/002,829, filed Jan. 6, 2011, Shenoy.
Office Action dated Jul. 24, 2012, in connection with related U.S. Appl. No. 12/870,462, filed Aug. 27, 2010, Shenoy.
Final (Rejection) Office Action dated Mar. 18, 2013, in connection with related U.S. Appl. No. 12/870,462, filed Aug. 27, 2010.
Final (Rejection) Office Action dated Jan. 31, 2013, in connection with related U.S. Appl. No. 13/002,829, filed Jan. 6, 2011.
Non-Final Office Action dated Apr. 11, 2014, in connection with related U.S. Appl. No. 14/175,829, filed Feb. 2, 2014, Vivek Shenoy.
Final Office Action dated Feb. 26, 2015, in connection with related U.S. Appl. No. 13/002,829, filed Jan. 6, 2011.
Response to Non-Final Office Action dated May 26, 2015, in connection with related U.S. Appl. No. 13/002,829, filed Jan. 6, 2011.
Response to Non-Final Office Action dated Apr. 20, 2015, in connection with related U.S. Appl. No. 13/843,128, filed Mar. 15, 2013.
Final Office Action dated Jun. 10, 2015, in connection with related U.S. Appl. No. 13/843,128, filed Mar. 15, 2013.
Partial International Search dated May 11, 2015, in connection with related PCT/US2015/019938, filed Mar. 11, 2015.
International Search Report and Written Opinion dated Jul. 3, 2015, in connection with related PCT/US2015/019938, filed Mar. 11, 2015.
Office Action dated Jul. 1, 2015, in connection with related U.S. Appl. No. 13/974,930, filed Aug. 23, 2013.
Restriction Requirement dated Jul. 23, 2015, in connection with related U.S. Appl. No. 14/642,121, filed Mar. 9, 2015.
Response to Final Office Action dated Aug. 10, 2015, in connection with related U.S. Appl. No. 13/843,128, filed Mar. 15, 2013.
Response to Restriction Requirement dated Sep. 23, 2015, in connection with related U.S. Appl. No. 14/642,121, filed Mar. 9, 2015.
Supplemental Response to Final Office Action dated Sep. 3, 2015, in connection with related U.S. Appl. No. 13/843,128, filed Mar. 15, 2013.
Final Office Action dated Sep. 15, 2015, in connection with related U.S. Appl. No. 13/002,829, filed Jan. 6, 2011.
Chow, S. P. et al., Fracture of the Tibial Tubercle in the Adolescent; British Editorial Society of Bone and Joint Surgery, vol. 72-B. No. 2, Mar. 1990.
Response to First Non-Final Office Action dated Nov. 2, 2015, in connection with U.S. Appl. No. 13/974,930, filed Aug. 23, 2013.
Non-Final Office Action dated Oct. 7, 2015, in connection with U.S. Appl. No. 14/642,121, filed Mar. 9, 2015.
Gumpel et al., An Objective Assessment of Synovitis of the Knee: Measurement of the Size of the Suprapatellar Pouch on Xeroradiography. Annals of the Rheumatic Diseases. 1980, (39): 359-366.
Response to First Non-Final Office Action dated Jan. 25, 2016, in connection with related U.S. Appl. No. 14/642,121, filed Mar. 9, 2015.
Office Action dated Feb. 26, 2016, in connection with related U.S. Appl. No. 13/974,930, filed Aug. 23, 2013.
Appellant's Brief dated Mar. 15, 2016, in connection with related U.S. Appl. No. 13/002,829, filed Jan. 6, 2011.
Lafaver, et al., "Tibial Tuberosity Advancement for Stabilization of the Canine Cranial Cruciate Ligament-Deficient Stifle Joint: Surgical Technique, Early Results, and Complications in 101 Dogs", Veterinary Surgery, 36:573-586, 2007.
Office Action dated May 5, 2016, in connection with U.S. Appl. No. 14/642,121, filed Mar. 9, 2015, Shenoy.
Examination Search Report dated Sep. 6, 2016, in connection with Canadian Application No. 2,771,332.
Response to Second Non-Final Office Action dated Oct. 5, 2016, in connection with U.S. Appl. No. 14/642,121, filed Mar. 9, 2015, Shenoy.
Notice of Allowance dated Jun. 21, 2016, in connection with U.S. Appl. No. 13/974,930, filed Aug. 23, 2013, Shenoy.
Restriction Requirement dated Jul. 22, 2015, in connection with related U.S. Appl. No. 14/644,792, filed Mar. 11, 2015.
Response to Restriction Requirement dated Sep. 11, 2015, in connection with related U.S. Appl. No. 14/644,792, filed Mar. 11, 2015.
Non-final Office Action dated Sep. 25, 2015, in connection with related U.S. Appl. No. 14/644,792, filed Mar. 11, 2015.
Office Action dated May 18, 2016, in connection with U.S. Appl. No. 14/644,792, filed Mar. 11, 2015, Shenoy.
Amendment and Response to Second Non-Final Office Action dated Sep. 19, 2016, in connection with U.S. Appl. No. 14/644,792, filed Mar. 11, 2015, Shenoy.
Office Action dated Oct. 6, 2016, in connection with U.S. Appl. No. 13/002,829, filed Jan. 6, 2011, Shenoy.
Response to Final Office Action dated Apr. 26, 2016, in connection with U.S. Appl. No. 13/974,930, filed Aug. 23, 2013.
Amendment and Response to First Non-Final Office Action dated Feb. 3, 2016, in connection with U.S. Appl. No. 14/644,792, filed Mar. 11, 2015, Shenoy.
Response to Final Office Action dated Apr. 26, 2016, in connection with U.S. Appl. No. 13/974,930, filed Aug. 23, 2013, Shenoy.
Office Action dated Oct. 2, 2017, in connection with U.S. Appl. No. 15/295,560, filed Oct. 17, 2016.
Response to Office Action dated Mar. 2, 2018, in connection with U.S. Appl. No. 15/295,560, filed Oct. 17, 2016.
Final Office Action dated Jun. 14, 2018, in connection with U.S. Appl. No. 15/295,560, filed Oct. 17, 2016.
Synthes, Inc., LCP Proximal Tibial Plate 3.5; Technique Guide; pp. 1-20; Jun. 2011.
Synthes TomoFix Osteotomy System Technique Guide. A comprehensive plating system for stable fixation of osteotomies around the knee. 38 pages.
Loqteq Anatomical Plating System Design Rationale. Locking Compression Technology by aap. aap Implantate AG. 11 pages.
Response to Election/Restriction dated Jul. 1, 2014 in connection with related U.S. Appl. No. 14/175,813, filed Feb. 7, 2014.
Notice of Allowance dated Feb. 3, 2015, in connection with related U.S. Appl. No. 14/175,813, filed Feb. 7, 2014.

(56) References Cited

OTHER PUBLICATIONS

Lapinskaya, Valentina Spiridonovna, "Treatment of Diseases and Injuries of Hip Joint Using a Method of Distraction", Kuibyshev Medical Institute, 1990.
Larionov D. Yu, et al., "Medical Devices," Scientific and Technical Bimonthly Journal, May-Jun. 2008.
Lapinskaya, V.S., et al., "An Endoapparatus for Restoration of the Hip Joint," Writers Collective, 2008, UDK 615.472.03:616.728.2-089.28; pp. 8-12.
Tomita, Naohide, "Development of Treatment Devices for Cartilage Regeneration", BME vol. 16, No. 2.
Lentsner, A.A., et al., "Device For Functional Relief of Hip Joint in Cotyloid Cavity Fracture Cases", Ortop Travmatol Protez. Apr. 1990 (4) 44-6.
Aldegheri, Roberto, M.C., et al.; "Articulated Distraction of the Hip Conservative Surgery for Arthritis in Young Patients," Clinical Orthopaedics and Related Research, No. 301, pp. 94-101.
Andriacchi, Thomas P., Ph.D. et al.; "Methods for Evaluating the Progression of Osteoarthritis"; Journal of Rehabilitation Research and Development, vol. 37, No. 2., Mar./Apr. 2000, pp. 163-170.
Arendt, Elizabeth, M.D.; "Anatomy and Malalignment of the Patellofemoral Joint—Its Relation to Patellofemoral Arthrosis"; Clinical Orthopaedics and Related Research; 2005, No. 436, pp. 71-75.
Benzel, Edward; "Qualitative Attributes of Spinal Implants"; in: Biomechanics of Spine Stabilization, 1995, pp. 137-150.
Buckwalter, Joseph A.; "Joint Distraction for Osteoarthritis"; The Lancet, Department of Orthopaedic Surgery, University of Iowa Hospitals and Clinics, vol. 347, Feb. 3, 1996, pp. 279-280.
Coathup, M.J. et al.; "Osseo-mechanical induction of extra-cortical plates with reference to their surface properties and gemoetric designs", Elsevier, Biomaterials 20 (1999) pp. 793-800.
Deie, Masataka, M.D. et al.; "A New Articulated Distraction Arthroplasty Device for Treatment of the Osteoarthritic Knee Joint: A Preliminary Report"; Arthroscopy: The Journal of Arthroscopic and Related Surgery; vol. 23, No. 8 Aug. 2007: pp. 833-838.
Dienst, M. et al.; "Dynamic External Fixation for Distal Radius Fractures"; Clinical Orthopaedics and Related Research, 1997, vol. 338, pp. 160-171.
Gunther, Klaus-Peter, M.D.; "Surgical Approaches for Osteoarthritis"; Best Practice & Research Clinical Rheumatology, vol. 15, No. 4, 2001, pp. 627-643.
Hall, J. et al.; "Use of a Hinged External Fixator for Elbow instability after Severe Distal Humeral Fracture"; Journal of Orthopaedic Trauma, 2000, vol. 14, No. 6, pp. 442-448.
Klein, D. et al.; "Percutaneous Treatment of Carpal, Metacarpal, and Phalangeal Injuries"; Clinical Orthopaedics and Related Research, 2000, vol. 375, pp. 116-125.
Krakauer J. et al.; "Hinged Device for Fractures involving the Proximal Interphalangeal Joint"; Clinical Orthopaedics and Related Research, 1996, vol. 327, pp. 29-37.
Leon, Heriberto Ojeda, M.D. et al.; "Minimally Invasive Selective Osteotomy of the Knee: A New Surgical Technique"; Arthroscopy: The Journal of Arthroscopic and Related Surgery, vol. 17, No. 5 May-Jun. 2001: pp. 510-516.
Madey, S. et al.; "Hinged External Fixation of the elbow: optimal axis alignment to minimize motion resistance" Journal of Orthopaedic Trauma, 2000, vol. 14, No. 1, pp. 41-47.
Neel, Michael D., M.D. et al.; "Early Multicenter Experience With a Noninvasive Expandable Prosthesis"; Clinical Orthopaedics and Related Research, 2003, No. 415, pp. 72-81.
Neel, Michael D., M.D.; "Repiphysis—Limb Salvage System for the Skeletally Immature"; Wright Medical Technology, Reipiphysis Limb Salvage System, 2004, pp. 1-8.
Nockels, Russ P.; "Dynamic Stabilization in the Surgical Management of Painful Lumbar Spinal Disorders"; Spine, 2005, vol. 30, No. 16S, pp. S68-S72.
Orthofix; "Xcaliber Articulated Ankle"; advertising brochure, May 2004.
Orthofix; "Gentle Limb Deformity Correction"; website pages, http://www.eight-plate.com/, 2008.
Perry, Clayton R. et al.; "Patellar Fixation Protected with a Load-Sharing Cable: A Mechanical and Clinical Study"; Journal of Orthopaedic Trauma, 1988, vol. 2, No. 3, pp. 234-240.
Pilliar et al., "Bone Ingrowth and Stress Shielding with a Porous Surface Coated Fracture Fixation Plate," Journal of Biomedical Materials Research, vol. 13, (1979), pp. 799-810.
Repicci, John A., M.D. et al. "Minimally Invasive Unicondylar Knee Arthroplasty for the Treatment of Unicompartmental Osteoarthritis: an outpatient arthritic bypass procedure"; Orthopedic Clinics of North America, 35 (2004), pp. 201-216.
Sharma, Leena et al. "The Mechanism of the Effect of Obesity in Knee Osteoarthritis—The Mediating Role of Malalignment"; Arthritis & Rheumatism, vol. 43, No. 3, Mar. 2000, pp. 568-575.
Sommerkamp, G. et al.; "Dynamic External Fixation of Unstable Fractures of the Distal Part of the Radius"; The Journal of Bone and Joint Surgery; Aug. 1994, vol. 76-A, No. 8, pp. 1149-1161.
Tencer, Allan F. et al. "Fixation of the Patella (Chap. 9.3)"; in: Biomechanics in Orthopedic Trauma Bone Fracture and Fixation, 1994.
Thakur, A.J.; "Tension Band Wiring"; in; The Elements of Fracture Fixation, 1997, pp. 126-146.
Uchikura, C. et al.; "Comparative Study of Nonbridging and Bridging External Fixators from Unstable Distal Radius fractures"; Journal of Orthopaedic Science, 2004, vol. 9, No. 6, pp. 560-565.
Van Der Esch, M. et al.; "Structural Joint Changes, Malalignment, and Laxity in Osteoarthritis of the knee"; Scand J Rheumatol 2005; 34: pp. 298-301.
Weisstein, Jason S., M.D. et al.; "Oncologic Approaches to Pediatric Limb Preservation"; Journal of the American Academy of Orthopaedic Surgeons; vol. 13, No. 8, Dec. 2005, pp. 544-554.
Wilke, Hans-Joachim et al.; "Biomechanical Evaluation of a New Total Posterior-Element Replacement System" Spine, 2006, vol. 31, No. 24, pp. 2790-2796.
Wilkins, Ross M., M.D. et al. " I he Phenix Expandable Prosthesis"; Clinical Orthopaedics and Related Research, No. 382, pp. 51-58.
Yamamoto, Ei et al.; "Effects of Stress Shielding on the Transverse Mechanical Properties of Rabbit Patellar Tendons"; Journal of Biomechanical Engineering, 2000, vol. 122, pp. 608-614.
Nagai, et al., "B109 Mobility Evaluation of Hip-Joint Nonweight-Bearing Device," The Japan Society of Mechanical Engineers No. 02-26.
European Search Report dated Aug. 7, 2014, issued in connection with related EP14164658.
Extended Search Report dated Aug. 26, 2014, issued in connection with related EP14164658.
Non-Final Rejection Office Action dated Aug. 27, 2014, in connection with related U.S. Appl. No. 14/175,813, filed Feb. 7, 2014.
Notice of Allowance dated Aug. 4, 2014 in connection with related U.S. Appl. No. 14/175,829, filed Feb. 7, 2014, Vivek Shenoy.
Office Action dated Dec. 19, 2014, in connection with U.S. Appl. No. 13/843,128, filed Mar. 15, 2013.
Response to Final Office Action dated Apr. 1, 2013, in connection with related U.S. Appl. No. 13/002,829, filed Aug. 27, 2009.
Response to First Non-Final Office Action dated May 5, 2014, in connection with related U.S. Appl. No. 14/175,829, filed Feb. 7, 2014.
Response to Restriction Requirement dated Oct. 27, 2014, issued in connection with related U.S. Appl. No. 13/843,128, filed Mar. 15, 2013.
Restriction Requirement dated Aug. 25, 2014, issued in connection with related U.S. Appl. No. 13/843,128, filed Mar. 15, 2013.
Office Action dated Jul. 9, 2012, in connection with related European Application No. 10812664, entitled Method and Apparatus for Force Redistributon in Articular Joints, filed Aug. 27, 2010, Cotera, Inc.
Maquet, P., Biomechanical Treatment of Patellofemoral Osteoarthritis. Advancement of the Patellar Tendon; Review of Rheumatism and Osteoarticular Diseases, National Library of Medicine, Dec. 1963, vol. 30, Issue 12, pp. 780-785.
Maquet, Paul G.J., Biomechanics of the Knee With Application to the Pathogenesis and the Surgical Treatment of Osteoarthritis; Springer-Verlag Berlin Heidelberg New York, 1976, pp. 134-204.

(56) References Cited

OTHER PUBLICATIONS

Sridhar et al., Obesity and symptomatic osteoarthritis of the knee, The Journal of Bone & Joint Surgery, Instructional Review, vol. 94-B, No. 4, Apr. 2012, pp. 433-441.
Lasmar, et al., Importance of the Different Posterolateral Knee Static Stabilizers: Biomechanical Study; Clinics 2010; 65(4) pp. 433-440.
Hunter, David et al., Alignment and Osteoarthritis of the Knee, Journal of Bone and Joint Surgery, 2009: 91 Suppl. 1:85-9, pp. 85-89.
Halbrecht, Jeffrey L., Arthroscopic Patella Realignment: An All-Inside Technique, Arthroscopy: The Journal of Arthroscopic and Related Surgery, vol. 17, No. 9 Nov.-Dec. 2001; pp. 940-945.
Arnold, Allison S., et al., Do the hamstrings operate at increased muscle-tendon lengths and velocities after surgical lengthening? Journal of Biomechanics, Mar. 2005; pp. 1-9.
Unnanuntana, Aasis et al., Management of chronic lateral instability due to lateral collateral ligament deficiency after total knee arthroplasty: a case report; Journal of Medical Case Reports, 2010, 4:144; pp. 1-5.
Maquet, P., Biomechanical Aspects of the Relationship between Femur and Patella, Z. Orthop. 112 (1974); pp. 620-623.
Kwak, et al., Hamstrings and Iliotibial Band Forces Affect Knee Kinematics and Contact Pattern, Journal of Orthopaedic Research, 18: 101-108; The Journal of Bone and Joint Surgery, Inc. 1999.
Maquet P., Reduction of the articular pressure of the hip by surgical lateralization of the greater trochanter, PMID: 1015273, Clin Orthop Relat Res. Mar.-Apr. 1977; (123): 138 (Abstract only).
Maquet P., Importance of the position of the greater trochanter, PMID: 2382566, Acta Orthop Belg. 1990; 56 (1 Pt. B): 307 (Abstract only).
Maquet, Paul, "Advancement of the Tibial Tubersosity," Clinical Orthopaedics and Related Research, No. 15, 1976, pp. 225-230.
Townsend et al., "The Biomechanics of the Human Patella and its Implications for Chodromalacia," Journal of Biomechanics, 1977, vol. 10, pp. 403-407.
Supplementary European Search Report dated May 23, 2012 for related application EP10812664 filed Aug. 27, 2010, entitled "Method and Apparatus for Force Redistribution in Articular," Cotera, Inc.
Arnoczky et al., Biomechanical Analysis of Forces Acting About the Canine Hip, American Journal Veterinary Research, vol. 42, Issue: 9, Sep. 1981, pp. 1581-1585.
Becker et al., Surgical Treatment of Isolated Patellofemoral Osteoarthritis, Clinical Orthopaedics and Related Research vol. 466, No. 2, Feb. 2008, pp. 443-449.
Cerejo et al., The Influence of Alignment on Risk of Knee Osteoarthritis Progression According to Baseline Stage of Disease, Arthritis & Rheumatism, vol. 46, No. 10, Oct. 2002, pp. 2632-2636.
Clifford et al., The KineSpring load absorber implant: Rationale, Design and Biomechanical Characterization, Journal of Medical Engineering & Technology, vol. 35, No. 1, Jan. 2011, pp. 65-71.
Delp et al., An Interactive Graphics-Based Model of the Lower Extremity to Study Orthopaedic Surgical Procedures, IEEE Transactions on Biomedical Engineering, vol. 37, No. 8, Aug. 1990, pp. 757-767.
Delp et al., Biomechanical Analysis of the Chiari Pelvic Osteotomy Preserving Hip Abductor Strength, Reprinted from Clinical Orthopaedics, vol. 25, May 1990, pp. 189-198.
Free et al., Trochanteric Transfer in Total Hip Replacement: Effects on the Moment Arms and Force-Generating Capacities of the Hip Abductors, Journal of Orthopaedic Research, vol. 14, No. 2, 1996, pp. 245-250.
Jack Farr, M.D., Tibial Tubercle Osteotomy, Techniques in Knee Surgery, vol. 2, Issue 1, 2003, pp. 28-42.
Goetz et al., Hip Joint Contact Force in the Emu (*Dromaius novaehollandiae*) during Normal Level Walking, Journal of Biomechanics, 41(4), 2008, pp. 770-778.
Jacobsen et al., Hip dysplasia: a significant risk factor for the development of hip osteoarthritis. A cross-sectional survey, Rheumatology vol. 44 No. 2, 2005, pp. 211-218.

Jingushi et al., Transtrochanteric Valgus Osteotomy for the Treatment of Osteoarthritis of the Hip Secondary to Acetabular Dysplasia, The Journal of Bone & Joint Surgery [Br], vol. 84-B, No. 4, May 2002, pp. 535-539.
Kirkley et al., The Effect of Bracing on Varus Gonarthrosis, The Journal of Bone and Joint Surgery, vol. 81-A, No. 4, Apr. 1999, pp. 539-548.
Lafeber et al., Unloading Joints to Treat Osteoarthritis, including Joint Distraction, Current Opinion in Rheumatology 2006, 18, pp. 519-525.
Lloyd et al., An EMG-driven Musculoskeletal Model to Estimate Muscle Forces and Knee Joint Moments in Vivo, Journal of Biomechanics 36, 2003, pp. 765-776.
Lloyd et al., Strategies of Muscular Support of Varus Andvalgus Isometric Loads at the Human Knee, Journal of Biomechanics 34, 2001, pp. 1257-1267.
Maquet, P, Biomechanics of Hip Dysplasia, Acta Ortopaedica Belgica, vol. 65—3, 1999, pp. 302-314.
McWilliams et al., Mild Acetabular Dysplasia and Risk of Osteoarthritis of the hip: a case-control study, Annals of the Rheumatic Diseases, 2010; 69, pp. 1774-1778.
Merritt et al., Influence of Muscle-Tendon Wrapping on Calculations of Joint Reaction Forces in the Equine Distal Forelimb, Journal of Biomedicine and Biotechnology, vol. 2008, Article ID 165730, 9 pages.
Pedersen et al., A Model to Predict Canine Pelvic Limb Musuloskeletal Geometry, Acta Anat 1991; 140, pp. 139-145.
Pollo et al., Knee Bracing for Unicompartmental Osteoarthritis, Journal of the American Academy of Orthopaedic Surgeons, vol. 14, No. 1, Jan. 2006, pp. 5-11.
Pollo et al., Reduction of Medial Compartment Loads with Valgus Bracing of the Osteoarthritic Knee, The American Journal of Sports Medicine, vol. 30, No. 3, 2002, pp. 414-421.
Saleh et al., Operative Treatment of Patellofemoral Arthritis, The Journal of Bone & Joint Surgery, vol. 87-A, No. 3, Mar. 2005, pp. 659-671.
Sharma et al., The Role of Knee Alignment in Disease Progression and Functional Decline in Knee Osteoarthritis, JAMA, vol. 286, No. 2, Jul. 11, 2001, pp. 188-195.
Sims et al., Investigation of Hip Abductor Activation in Subjects with Clinical Unilateral Hip Osteoarthritis, Annals of the Rheumatic Diseases, 2002; 61: pp. 687-692.
Thorp et al., The biomechanical effects of focused muscle training on medial knee loads in OA of the knee: a pilot, proof of concept study, Journal of Musculoskeletal and Neuronal Interactions, 10(2): 2010, pp. 166-173.
Wenger et al., Early Surgical Correction of Residual Hip Dysplasia: The San Diego Children's Hospital Approach, Acta Orthopaedica Belgica, vol. 65, 1999, pp. 277-287.
Winby et al., Muscle and External Load Contribution to Knee Joint Contact Loads during Normal Gait, Journal of Biomechanics 42, 2009, pp. 2294-2300.
Response to Final Office Action dated Apr. 1, 2013, in connection with related U.S. Appl. No. 13/002,829, filed Aug. 27, 2010.
Amendment and Response to Final Office Action dated May 20, 2013, in connection with related U.S. Appl. No. 12/870,462, filed Aug. 27, 2010.
Advisory Action dated Apr. 23, 2013 in connection with related U.S. Appl. No. 13/002,829, filed Jan. 6, 2011.
Advisory Action dated Jun. 20, 2013 in connection with related U.S. Appl. No. 13/002,829, filed Jan. 6, 2011.
Tew, M et al.; Anteriorization of the quadriceps tendon. A biomechanical study on a new technique for unloading the patellofemoral joint. University of Tennessee College of Medicine; Poster No. 0848 • ORS 2012 Annual Meeting.
Miller, R.K., Goodfellow, J.W., Murray, D.W. and O'Connor, J.J., In vitro measurement of patellofemoral force after three types of knee replacement; The Journal of Bone & Joint Surgery (Br), vol. 80-B, No. 5, Sep. 1998; pp. 900-906.
Ganesh, V.K., et al., Biomechanics of bone-fracture fixation by stiffness-graded plates in comparison with stainless-steel plates, Biomedical Engineering Online, 2005, 4:46, 15 pgs.

(56) References Cited

OTHER PUBLICATIONS

Benli, Semih et al., Evaluation of bone plate with low-stiffness material in terms of stress distribution, Journal of Biomechanics, 41 (2008) 3229-3235.
Haase, Kristina et al., A Discussion on Plating Factors that Affect Stress Shielding Using Finite Element Analysis, Journal of Biomechanical Science and Engineering, vol. 5, No. 2, 2010, pp. 129-141.
Anatomic Locked Plating System Brochure, Biomet® Orthopedics, Form BMET0002.0, Rev 053112, pp. 1-16, Copyright 2012.
SPS Periarticular Plates Brochure, Stryker® Trauma AG, Literature No. 982274, Lot B46404, pp. 1-8; Copyright 2004.
Zimmer® Periarticular Distal Femoral Locking Plate Surgical Technique, the Science of the Landscape, Zimmer, 97-2347-044-00 Rev. 1 7.5 ML; pp. 1-20; Copyright 2005.
Hessmann et al., Compression Plate With or Without Lag Screw; AO Surgery Reference—Online reference in clinical life; Distal Tibia—Reduction & Fixation—Compression Plate; https://www2.aofoundation.org/wps/portal; pp. 1-9; Dec. 3, 2008.
LCP Locking Compression Plate—Ordering Information; Synthes®, 036.000.017, SE_042064 AD, 31080015; pp. 1-68; Copyright 2008.
Plates for 4.5 mm and 6.5 mm Screws; Raj Surgical Works; http://www.orthoindustries.com/plates-for-4-5-mm-and-6-5-mm-screws.html; pp. 1-8; printed Nov. 19, 2012.
Final Office Action dated Jan. 31, 2013, in connection with related U.S. Appl. No. 13/002,829, filed Jan. 6, 2011.
PCT International Search Report and Written Opinion dated Jan. 9, 2014, for related application PCT/US2013/058877 filed Sep. 10, 2013 entitled "Method and Apparatus for Treating Canine Cruciate Ligament Disease," Vivek Shenoy.
Bruce et al., "Patellar Contact Pressure Changes with Anteromedialization of Tibial Tubercle, Lateral Release, and New Technique for Elevating Quadriceps Tendon: A Biomechanical Study," Journal of Surgical Orthopaedic Advances 22(4), pp. 270-276, 2013.

\* cited by examiner

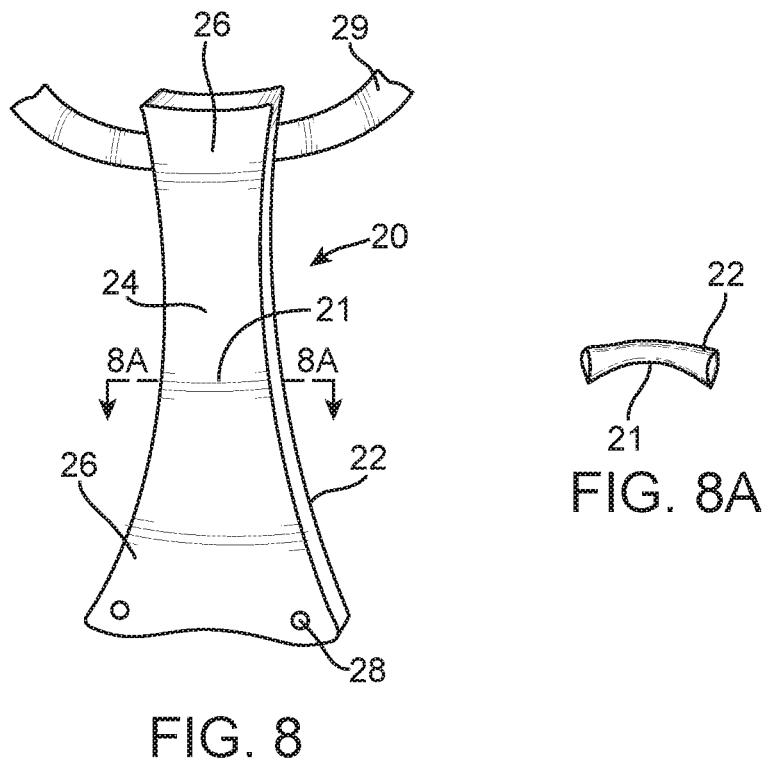
FIG. 8
FIG. 8A
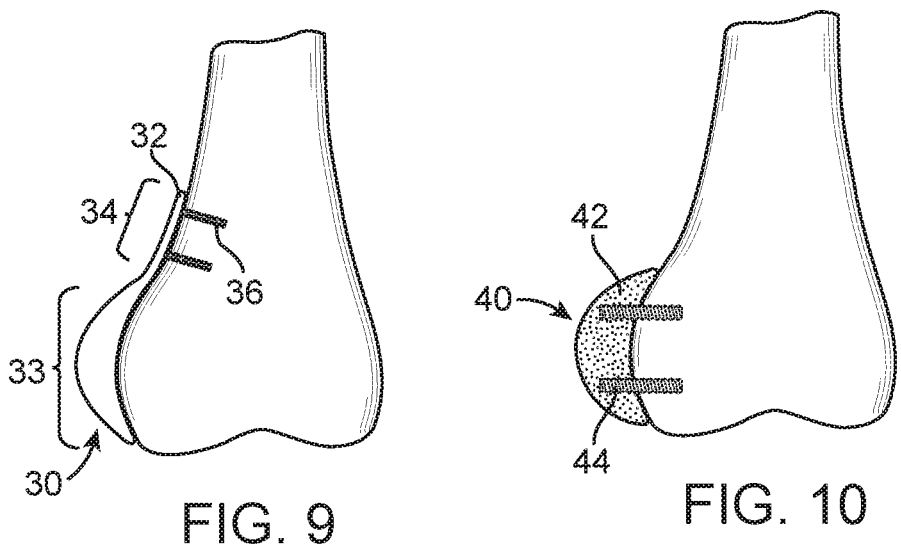
FIG. 9
FIG. 10

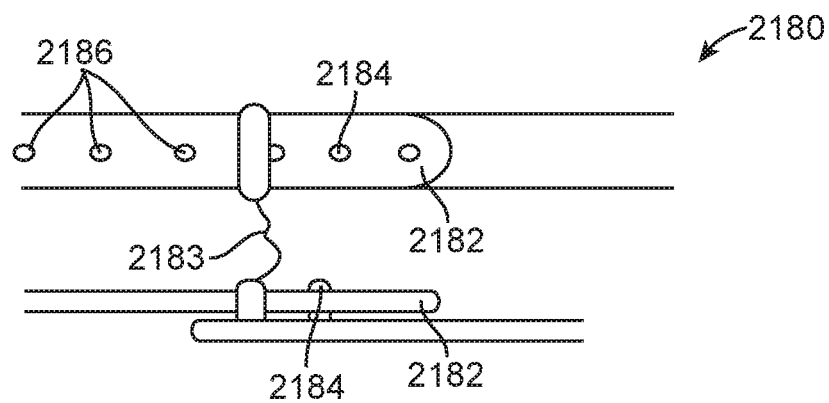
FIG. 53
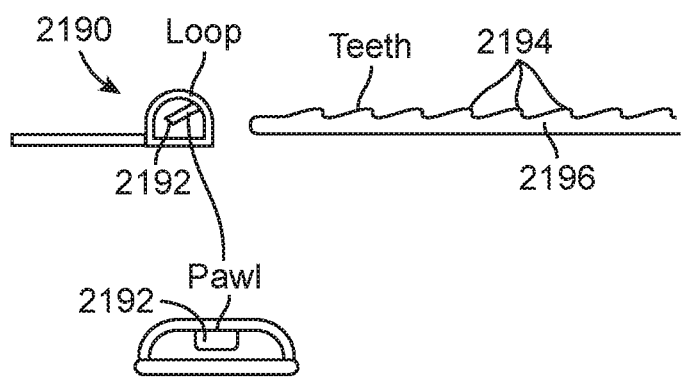
FIG. 54
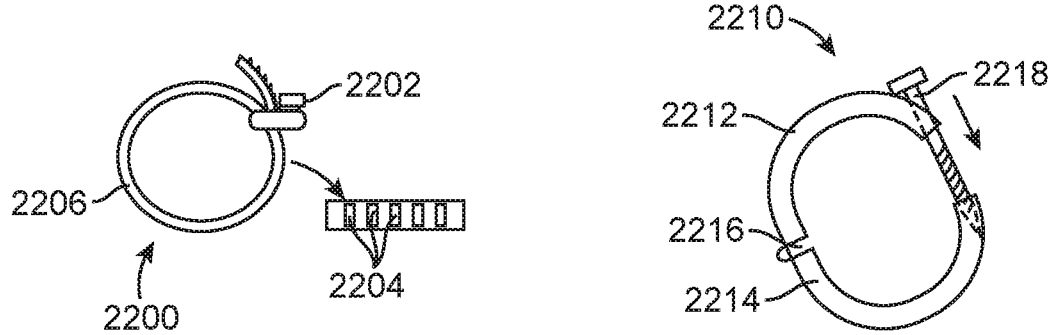
FIG. 55
FIG. 56

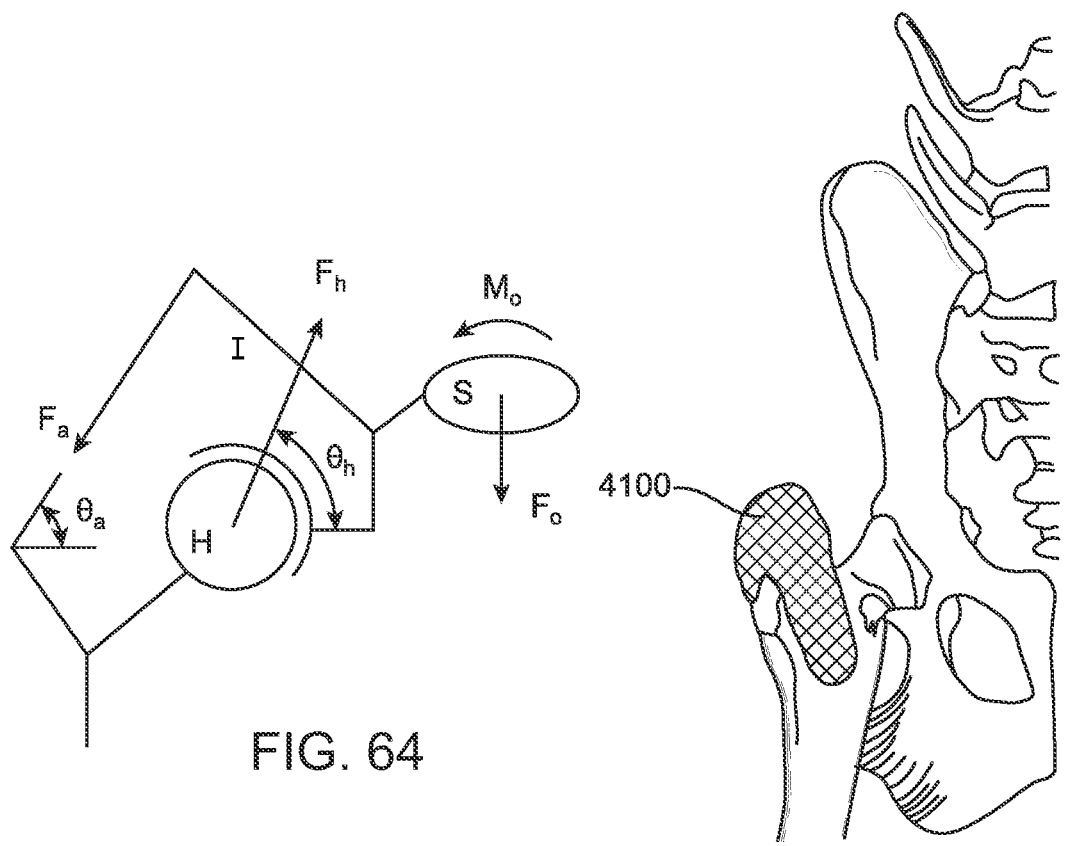
FIG. 64
FIG. 65
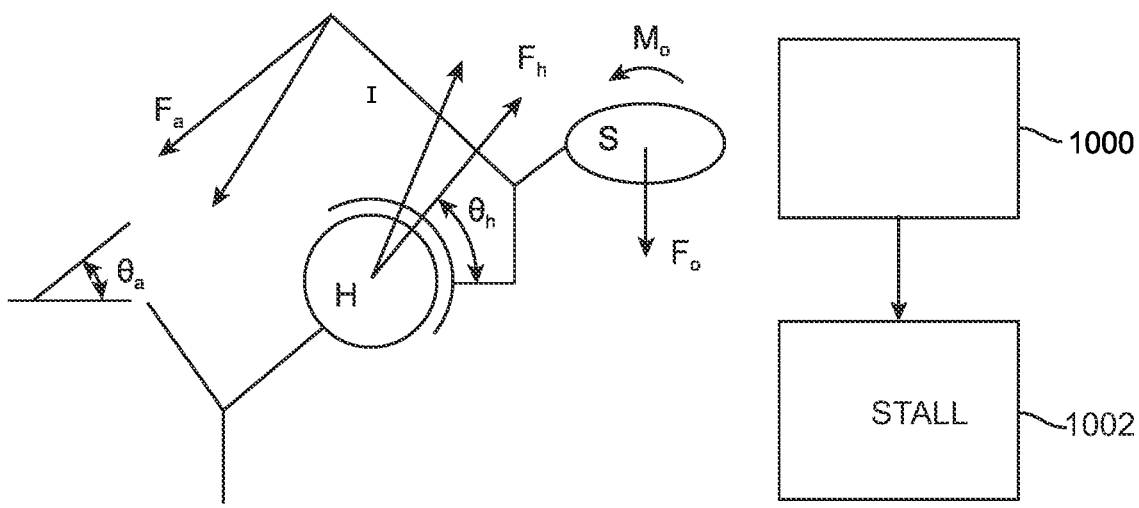
FIG. 66
FIG. 67

METHOD AND APPARATUS FOR FORCE REDISTRIBUTION IN ARTICULAR JOINTS

RELATED APPLICATIONS

The present application is a continuation of U.S. patent application Ser. No. 13/002,829, filed Jan. 6, 2011, which is a U.S. national phase of PCT/US10/46996, filed Aug. 27, 2010; which claims the benefit of priority of U.S. provisional application No. 61/237,518, filed Aug. 27, 2009, and of U.S. provisional application No. 61/288,692, filed Dec. 21, 2009. Each of these applications are incorporated by reference herein.

FIELD OF THE INVENTION

The present invention generally relates to the field of orthopedics. In particular, the present invention is directed to an interventional technique and an implant for redistributing forces within articular joints to provide a therapeutic effect.

BACKGROUND

The human body contains many joints that permit articulation of varying degrees between bones. Those that permit free articulation are referred to as diathroses. Examples include the hip, knee, elbow and shoulder. A variety of connective tissues are associated with the diathroses joints, including intra-articular cartilages that provide cushioning and smooth sliding surfaces, ligaments that provide flexible connections between bones and tendons that slide over joints and connect the muscles to provide motion. When connective tissues are compromised, joint pain and loss of function can result.

One example of compromised connective tissue is osteoarthritis of the knee or knee OA. Knee OA is one of the most common causes of disability in the United States. OA is sometimes referred to as degenerative, or wear and tear, arthritis. The knee joint is formed by the articulation of the femur, patella, and tibia (see FIG. 3). Like other freely articulating joints, the knee joint is enclosed by a fibrous joint capsule, lined by a synovial membrane. The inferior surface of the patella articulates with the femoral surface forming the patellofemoral joint. The distal end of the femur has two curved articular surfaces called the medial and lateral condyles. These surfaces articulate with the medial and lateral tibial condyles, forming the tibiofemoral joint, which flexes and extends the knee. Two fibrocartilagenous discs (i.e., menisci) lie between the tibial and femoral condyles to compensate for the incongruence of the articulating bones. Because the distal end of the femur is curved and asymmetric in shape, the knee joint not only flexes and extends like a hinge, but it also slides and rotates during flexion, resulting in a complex motion for the joint.

Knee OA is characterized by the breakdown of the articular cartilage within the joint. Over time, the cartilage may wear away entirely, resulting in bone-on-bone contact. Since bones, unlike cartilage, have many nerve cells, direct bone contact can be very painful to the OA sufferer. In addition to the pain and swelling, the OA sufferer can experience a progressive loss of mobility at the knee joint. This is due to loss of the joint space, where the articular cartilage has completely worn away. OA usually affects the side of the knee closest to the other knee (called the medial compartment) more often than the outside part (the lateral compartment). A bowlegged posture also places more pressure than normal on the medial compartment. The added pressure leads to more pain and faster degeneration where the cartilage is being squeezed together.

Various medications are often recommended to reduce the swelling and pain of OA. Other treatments such as weight loss, braces, orthotics, steroid injections, and physical therapy may also help alleviate pain and restore function. However, since articular cartilage is avascular, or lacks a blood supply, repair and growth of adult cartilage is minimal. If the pain or immobility becomes too severe and other therapies do not alleviate the symptoms, surgical interventions become necessary. In some cases, surgical treatment of OA may be appropriate. Surgeries can range from arthroscopic procedures to clean the joint by removing loose fragments of cartilage and by smoothening the rough spots on the cartilage to total knee replacement with an artificial knee.

Another surgical treatment for knee OA is proximal tibial osteotomy, a procedure intended to realign the angles in the lower leg to help shift pressure from the medial to the lateral side of the knee. The goal is to reduce the pain and delay further degeneration of the medial compartment.

In proximal tibial osteotomy, the upper (proximal) part of the tibia is cut, and the angle of the joint is changed. This converts the extremity from being bowlegged to straight or slightly knock-kneed. By correcting the joint deformity, pressure is taken off the cartilage. However, a proximal tibial osteotomy is only temporary before a total knee replacement becomes necessary. The benefits of the operation usually last for five to seven years if successful. The advantage to this approach is that very active people still have their own knee joint, and once the bone heals there are no restrictions on activities.

Another connective tissue disorder that occurs in the knee is excessive patellar compressive force (PCF). In patients suffering from patellofemoral arthritis, excessive compressive forces on the patella cause pain and lead to cartilage degeneration between the patella and femur.

Current treatments to relieve the excessive PCF in such patients involve highly invasive osteotomies to reposition the attachment point of the patellar tendon on the tibia. One such procedure is the Maquet procedure, which displaces the tibial tuberosity anteriorly by cutting away a portion of the bone and repositioning it with a bone graft inserted thereunder. Moving the attachment point of the patellar tendon anteriorly decreases the overall PCF by changing the moment arm and effective angle of the force. However, the procedure is highly invasive, involving high surgical morbidity and significant rehabilitation, which can be challenging for some patients. Lack of compliance with rehabilitation can also decrease positive outcomes even in initially successful procedures.

In addition to the Maquet osteotomy, there are other tibial tubercle procedures like the Fulkerson osteotomy and Elmslie-Trillat osteotomy that also displace the patellar tendon to reduce the compressive forces on the patella. The osteotomies also redistribute the load on the patella by transferring the load to other regions of the patella. These alternative procedures similarly involve relatively high surgical morbidity and require significant rehabilitation.

Another example of compromised connective tissue leading to joint pain and loss of function is hip dysplasia. The hip joint is the deepest and largest joint in the body, and is formed between the head of the femur and the acetabulum of the pelvis (see FIG. 27). The primary purpose of the hip joint is to support the weight of the body in both static (e.g., standing) and dynamic (e.g., running and walking) postures.

Hip dysplasia is a congenital or acquired deformation or a misalignment of the hip joint. The condition can range from barely detectable to severely malformed or dislocated. Early-age hip dysplasia can often be treated using a Pavlik harness or a Frejka pillow or splint. In older children, the hip abductor and iliopsoas muscles have to be treated surgically because they adapt to the dislocated joint position. Hip dysplasia is often cited as causing osteoarthritis (OA) of the hip at a comparatively young age. Dislocated load bearing surfaces lead to increased and unusual wear. Subsequent treatment with total hip arthroplasty (hip replacement) is complicated by a need for revision surgery due to skeletal changes as the body matures.

The current treatment for dysplasia-related pain is femoral neck osteotomy or peri-acetabular osteotomy. For more advanced cases, a total hip replacement is the only surgical option. In either case, the treatment involves extensive surgery with long rehabilitation protocols. There is thus a need for a less invasive, yet effective approach to treatment.

Compromise of connective tissues leading to joint pain and loss of function are not limited to humans. For example, the high frequency of canine hip dysplasia has made the canine hip a focus of attention among veterinary orthopedists. Canine hip dysplasia usually begins to manifest itself through decreased activity with varying degrees of joint pain. Often these signs are first observed between the ages of four months and one year.

In a normal canine hip joint, the head of the femur fits congruently into the acetabulum (see FIGS. 61A-B). In a dysplastic joint, the femoral head conforms poorly to the acetabulum. More space is evident between the bones. Displacement of the femoral head is the hallmark of the disease. As with human joint misalignment conditions, various surgical procedures—femoral head ostectomy, intertrochanteric osteotomy (ITO), triple pelvic osteotomy (TPO) and total hip replacement, have been devised to treat hip dysplasia. There is thus also a need for less invasive solutions to joint misalignment conditions and disease for canine and other veterinary applications.

Given the long-term ineffectiveness of current non-surgical treatments and the significant trauma of current surgical treatments, alternatives with significantly lower surgical morbidity and rehabilitation requirements could be beneficial to patients showing early as well as advanced symptoms of compromised connective tissue-related disorders of articular joints, such as hip dysplasia, and lateral knee and patellar femoral osteoarthritis.

SUMMARY OF THE DISCLOSURE

Selectively placed implants are used to address pathologies of joints arising from improper force distribution. By using appropriately sized and positioned implants as described herein, displacement of targeted connective and muscle tissues surrounding the joint is accomplished in order to realign force vectors and/or alter moment arms loading the joint to achieve therapeutic effects without cutting bone and with minimal cutting of the connective tissues.

Embodiments of the present invention may be applied to virtually any articular joint, including but not limited to the knee and hip. In addition to the implants and related prosthesis and apparatus described, embodiments of the present invention include methods of treating joint disorders and methods of installing implants and prostheses for less invasive joint treatments.

In one exemplary embodiment of the invention, an apparatus for treating an articular joint to effect force distribution in the joint is disclosed. The exemplary apparatus is for treating articular joints including at least first and second bones with facing articular surfaces, wherein the bones are positioned with respect to one another by associated muscle and connective tissues. These tissues comprise target tissues for therapy with the apparatus. Such an exemplary apparatus may comprise a bearing member with a bearing surface disposed on the bearing member. The bearing member is configured and dimensioned for placement in a therapeutic location proximate at least one said target tissue and has a thickness sufficient to displace the target tissue from its natural path to a therapeutic path when placed in the therapeutic location. The bearing surface disposed on the bearing member is configured to atraumatically engage the target tissue and to permit movement of the target tissue there along. Specific structures, configurations, dimensions and fixation modalities are described in more detail herein below.

In another exemplary embodiment of the present invention, a method of treating an articular joint to effect force distribution in the joint is disclosed. The exemplary method is suited for treating articular joints including at least first and second bones with facing articular surfaces, wherein the bones being positioned with respect to one another by associated muscle and connective tissues. The exemplary method comprises selecting at least one of the associated muscle and connective tissues as target tissue for treatment, displacing the target tissue without severing the bones or target tissue, and redistributing loading in the joint to achieve a therapeutic effect by the displacement. Alternative and more specific methodologies are described in more detail herein below.

BRIEF DESCRIPTION OF THE DRAWINGS

For the purpose of illustrating the invention, the drawings show aspects of one or more exemplary embodiments of the invention. However, it should be understood that the present invention is not limited to the precise arrangements and instrumentalities shown in the drawings, wherein:

FIGS. 8 and 8A are a perspective view and a cross-sectional view, respectively, of a soft compliant prosthesis according to an exemplary embodiment of the present invention.

FIG. 9 is a schematic anterior view of the distal end of a femur with a prosthesis implanted according to an exemplary embodiment of the present invention.

FIG. 10 is a schematic anterior view of the distal end of a femur with a prosthesis implanted according to an alternative exemplary embodiment of the present invention.

FIGS. 53, 54, 55 and 56 show examples of cinching mechanisms that may be used for the strap of FIG. 52 in accordance with exemplary embodiments of the present invention.

FIG. 64 is a free body diagram illustrating static forces and moments applied in canine hind hip joint in a three-legged stance.

FIG. 65 is an anterior view of a canine hip including an implant according to an exemplary embodiment of the present invention.

FIG. 66 is a free body diagram illustrating the modification of the biomechanics of the canine hip joint including an implant according to embodiments of the present invention.

FIG. 67 is a simplified flow chart showing a treatment regimen in accordance with an exemplary embodiment of the present invention.

DETAILED DESCRIPTION

Joint conditions that result from or exacerbate unbalanced force distribution through the joint may be addressed in embodiments of the present invention by interventional techniques involving a redistribution of forces exerted on the joint without the need for highly invasive surgeries requiring significant trauma to the joint and associated muscle and connective tissues. In some embodiments of the invention, increased forces can be selectively applied to one side of a joint by forcing select muscle and/or connective tissues (target tissues) around a longer or more angled path, thus increasing the magnitude, altering the effective direction, and/or changing the moment arm of forces exerted by such muscles or tissues on the joint. This may be accomplished, for example, by appropriately shaped implants that may be placed under selected target tissues relatively non-invasively compared to current surgical techniques for addressing such conditions.

Figure 1:
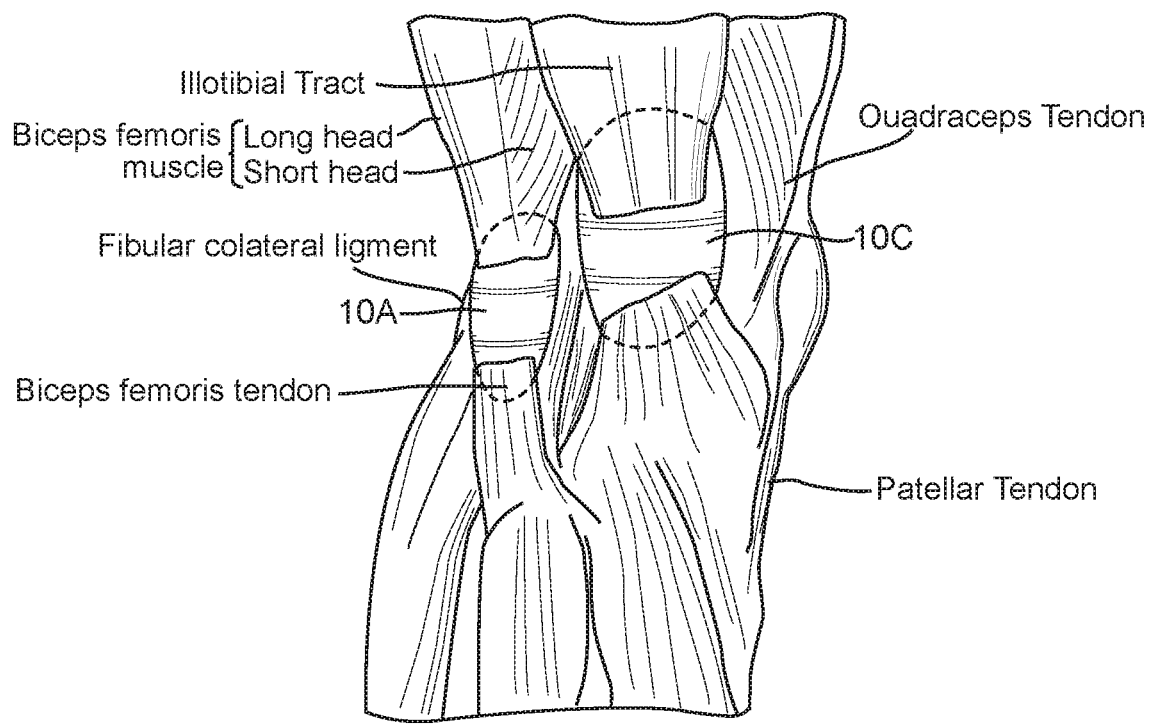
FIG. 1 is a partially cut away, lateral view of a knee, illustrating connective tissues and muscles associated with the knee and schematic examples of implants according to embodiments of the present invention.
Figure 2:
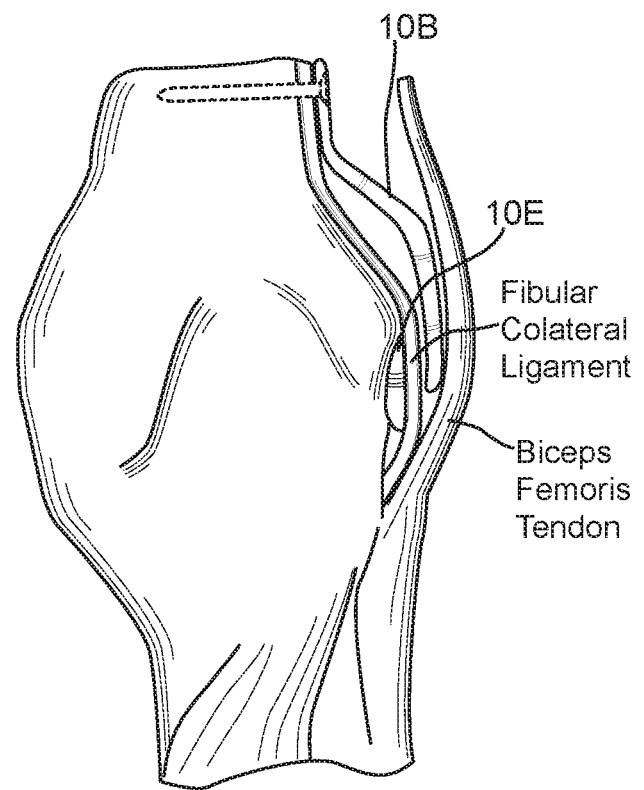
FIG. 2 is a partially cut away, posterior view of the right knee, illustrating connective tissues and muscles associated with the knee and schematic examples of implants according to further embodiments of the present invention.

In one more specific example of an embodiment of the invention, with particular application to the knee joint, it is proposed that by placing one or more implants under select target tissues, the lever through which muscle forces act on the joint can be altered to positively affect the joint loading. With respect to osteoarthritis of the knee, such target tissues may include the muscles, tendons or ligaments of the lateral side of the joint that counter medial forces and alleviate excessive medial side joint surface contact. As schematically illustrated in FIGS. 1 and 2, such a prosthesis could be placed below target tissues including but not limited to the biceps femoris tendon (implants 10A and 10B), the iliotibial band or Tensor Fascia latae (implant 10C), lateral quadriceps-patellar tendon (implant not shown), the lateral gastrocnemius (implant not shown), popliteus, or the fibular collateral ligament (implant 10E) to laterally displace the relevant muscle/tendon/ligament. Other target tissues may be readily identified by treating physicians based on a patient's particular anatomical structure and indications to be addressed.

In other exemplary embodiments particularly applicable to the hip, a prosthesis is arranged superficial to the hip capsule but under at least a portion of the hip abductor muscle complex to alter the force vector provided by the hip abductors. As illustrated for example in FIGS. 33A-B, such a prosthesis (implant 220) may be placed or arranged under anyone of, or a combination of multiple, abductor muscles to achieve the desired resultant force vector. Any of the muscles involved in hip abduction may be targeted, including the gluteus medius GMed, gluteus minimus GMin, the psoas, the piriformis PIR, the tensor fascia latae, the quadratus lumborum, and the rectus femoris. In embodiments, the prosthesis would be placed in the tissue between the gluteus muscles and the ligaments L, but the prosthesis may be positioned in other locations.

Advantageously, the implants according to embodiments of the invention may be placed outside the joint capsule so as to minimize interference with the function of the joint and the risk of infection and other problems associated with the placement of foreign bodies within the joint capsule. In addition to alleviating the pain and potentially altering the progression of the articular degeneration, placing the prosthesis under the lateral target tissues could also reduce the lateral laxity of the joint. Bursa associated with the target tissues are likely candidates as locations for such implants and may be displaced or removed and replaced by the implants. However precise placement at the bursa location is not required and depending on the clinical situation implants according to embodiments of the present invention may be placed at sites displaced from associated bursa as well.

Figure 3:
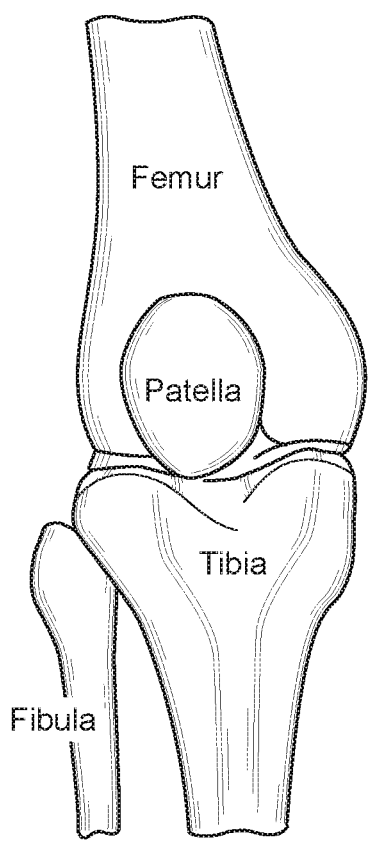
FIG. 3 is a front or anterior view of the bones of the right knee joint.

Before addressing more details of exemplary embodiments of the present invention, it is helpful to have a basic understanding of the joint biomechanics, in a first example, the knee. As illustrated in FIG. 3, the knee joint involves four bones, the femur at the top, the fibula and tibia below and patella centrally located at the front. Varus and valgus orientation of the lower extremity (defined as looking at the tibia from the knee towards the ankle) are commonly referred to, respectively, as bow-legged (varus) and knock-kneed (valgus).

Because the gait cycle has a critical effect on joint loading, the normal gait cycle of a human will now be explained with reference to FIG. 4. The gait cycle begins when one foot contacts the ground (A) and ends when that foot contacts the ground again (G). Thus, each cycle begins at initial contact with a stance phase and proceeds through a swing phase until the cycle ends with the limb's next initial contact. (Note that the description of the gait cycle is made with reference to motion of the black shaded leg in FIG. 4).

Stance phase accounts for approximately 60 percent, and swing phase for approximately 40 percent, of a single gait cycle. Each gait cycle includes two periods when both feet are on the ground. The first period of double limb support begins at initial contact, and lasts for the first 10 to 12 percent of the cycle. The second period of double limb support occurs in the final 10 to 12 percent of stance phase. As the stance limb prepares to leave the ground, the opposite limb contacts the ground and accepts the body's weight. The two periods of double limb support account for 20 to 24 percent of the gait cycle's total duration.

When the body weight is borne equally on both feet at rest or in the double stance phase of gait (A-B and D-E in FIG. 4), the force that passes through the knee is only a fraction of body weight and there is no bending moment around either knee. However, the knee is maximally stressed when body weight passes onto the single leg (B-D).

Figure 5:
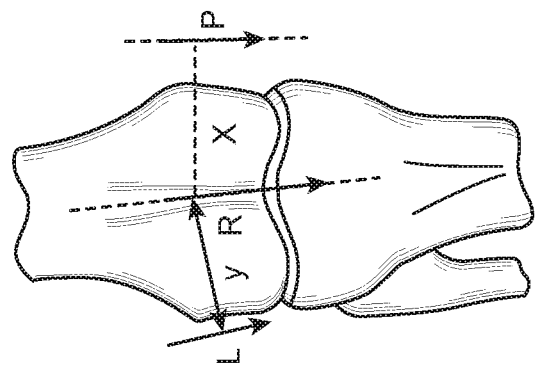
FIG. 5 is a free body diagram illustrating the forces acting on a normal knee joint during a portion of the gait cycle.
Figure 11:
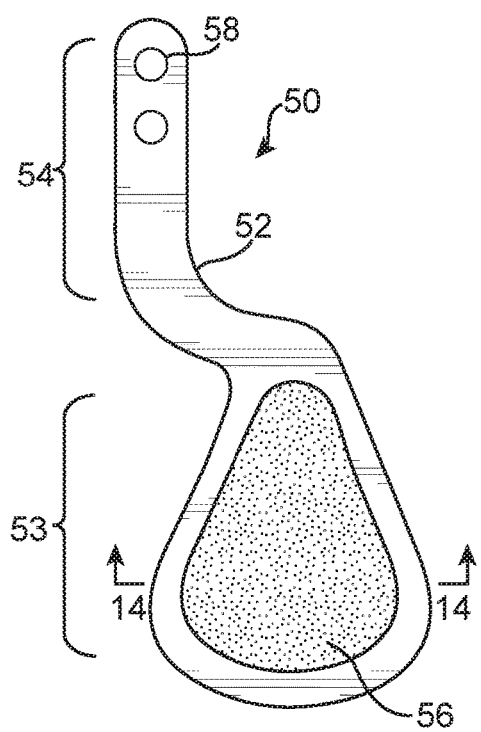
FIGS. 11, 12, 13, 13A and 13B are plan views of prostheses according to alternative exemplary embodiments of the present invention.

The resultant forces for a healthy knee in single leg stance are shown in the free body diagram of FIG. 5, wherein x represents the medial (varus) lever arm; y represents the lateral lever arm through which the lateral structures of the knee operate, P represents the weight supported by the knee, and R represents the resultant joint reaction force. As a result, the leg has a normal, slightly valgus orientation to the vertical and the plumb line from the center of gravity falls medial to the center of the knee.

The arrangement of forces exerts a bending moment on the knee acting through a medial lever that would tend to open the knee into varus, in other words opening the lateral side of the joint. In standing on one leg at rest with the knee fully extended, the lateral muscles, tendons, ligaments and capsule are tight. These structures resist the medially levered, varus bending moment. In the dynamic situation during gait, multiple muscles which cross the joint in the center or to the lateral side of center combine to provide a lateral resistance to opening of the lateral side of the joint due to the medial lever. These include target tissues such as the quadriceps-patellar tendon, the lateral gastrocnemius, popliteus, biceps and iliotibial tract (see FIGS. 1 and 2). The sum of the forces exerted by the target tissue can be represented as L in FIG. 5, operating through lever arm y. This combination determines the magnitude and direction of the resultant vector R of the tibial femoral joint load. In a healthy knee, this resultant is approximately centered between the lateral and medial condyles.

With increasing knee varus angle, the medial lever arm increases, requiring an increased lateral reaction L to prevent the joint from becoming excessively loaded on the medial side. If the forces urging the knee into a varus state reach a threshold level, as diagrammatically illustrated in FIG. 6, the ability of the associated connective tissues to compensate in their natural state is overcome so that the joint load R is borne on the medial compartment, leading to excessive wear, and eventually potentially significant joint pain. This situation is a condition that gives rise to osteoarthritis of the knee.

Figure 6:
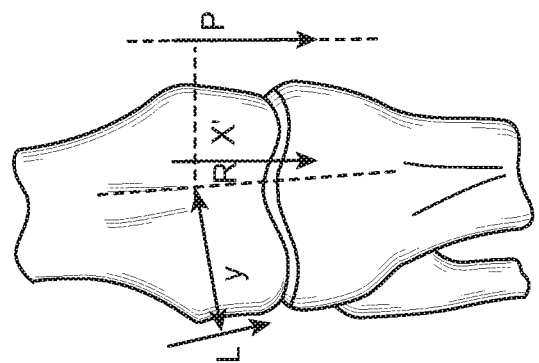
FIG. 6 is a free body diagram illustrating forces acting on a knee joint with excessive medial loading.

The situation illustrated in FIG. 6 can be addressed according to embodiments of the invention by altering the position of target tissues acting on the joint in order to adjust one or more of the force magnitude, angle and/or moment arm. Thus, as mentioned above, in exemplary embodiments, one or more implants are placed under selected target tissue in order to beneficially alter the force distribution by increasing the lateral moment (counterclockwise in the figure).

Figure 7:
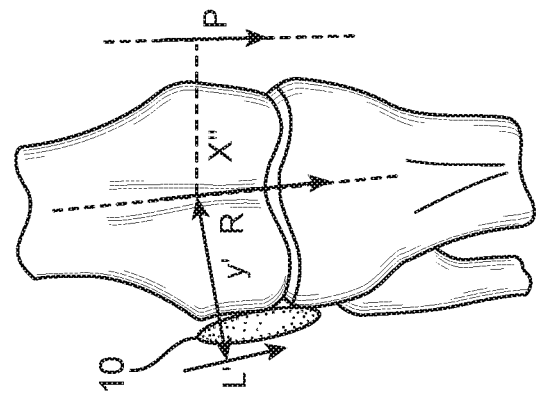
FIG. 7 is a free body diagram illustrating forces acting on a knee joint with an implant according to an exemplary embodiment of the present invention.

FIG. 7 illustrates an exemplary embodiment of the present invention with a generic implant 10 according to one embodiment positioned along the joint to assist in redistributing the forces acting on the joint to provide a therapeutic effect. As shown therein, implant 10 creates a space adjacent to the joint that forces the target tissues (not shown) that run there along to assume a longer path over the implant surface. That longer path may have a number of beneficial effects, including increasing the lateral moment arm y', moving the line of action for the target tissue to a more effective angle and/or tensioning the target tissue to increase amplitude of force vector L'. As a result, the effective lateral moment is increased to more effectively counter the medial moment created by supported weight P. This moves the joint load R laterally out of the medial compartment and back to a more normal, central location. Implant 10 may take many forms as discussed in more detail below with respect to various exemplary embodiments of the present invention.

The amount of displacement of the target tissue need not be large in order to potentially have a substantial effect on increasing lateral torque to assist in unloading the medial compartment. For example, an average person has a normal lateral lever arm (y) of about 50 mm. Thus, a lateral displacement increasing the lever arm (y') by only about 10-15 mm may increase the lateral torque by about 20%-30%. Dependent upon the geometry of a particular patient's joint, lateral displacements of between about 5 mm to about 30 mm may be possible, with displacements in the range of about 10 mm to about 30 mm, or more specifically about 10-20 mm, most typical.

EXAMPLE

Figure 68:
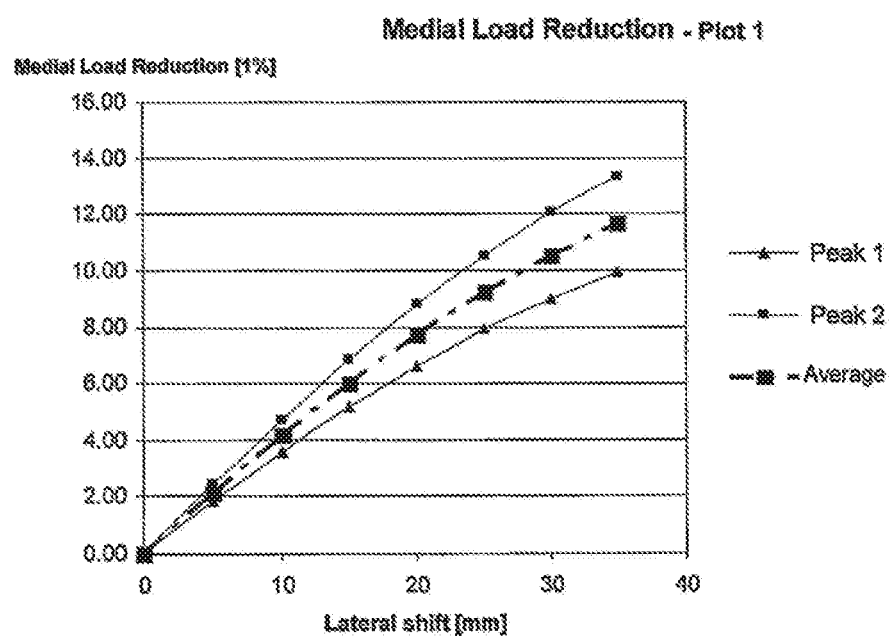
FIG. 68 is a plot of medial load reduction as determined through a computer simulation of one embodiment of the present invention.

To evaluate the change in loading in the medial compartment of the knee due to lateral displacement of the target tissue, simulations were performed using a computational model of the knee to determine an approximate percentage reduction in medial contact force. (For details of the computational model, see Lin, Y.-C., Walter, J. P., Banks, S. A., Pandy, M. G., and Fregly, B. J., *Simultaneous Prediction of Muscle and Contact Forces in the Knee During Gait*, p. 945-952, Journal of Biomechanics 2010, which is incorporated herein by reference). Medial contact forces were calculated at the two points of the gait cycle with peak medial contact forces (approximately 15% and 50% of the gait cycle at peaks 1 and 2, respectively) as a function of lateral displacement of lateral knee muscles. Lateral muscles were displaced 0 to 35 mm in increments of 5 mm as described in connection with embodiments of the invention. In this simulation, the origins of the three lateral knee muscles (tensor fascia latae, biceps femoris long head, and biceps femoris short head) were displaced laterally from the femur while there was no change to the insertion sites of the muscles. The results of these simulations, presented graphically in FIG. 68, showed that average medial load could be reduced by as much as about 12% at displacement of about 35 mm according to embodiments of the invention.

Figure 69:
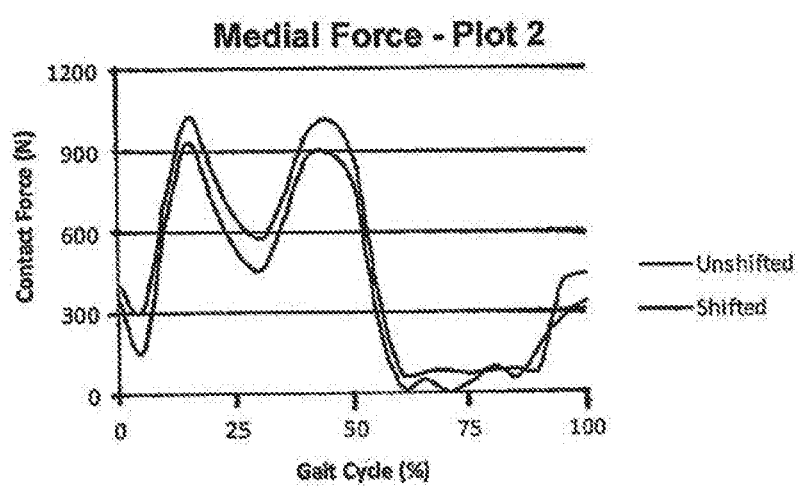
FIG. 69 is a plot of medial force as determined through a computer simulation of an embodiment of the present invention.

Simulations were also performed for absolute medial contact force as a function of percent of stance phase with the origin of the lateral muscles displaced by 30 mm. In this simulation, the origins of the three lateral knee muscles (tensor fascia latae, biceps femoris long head, and biceps femoris short head) were displaced laterally from the femur while there was no change to the insertion sites of the muscles. Results of this simulation, represented graphically in FIG. 69, show that medial contact force is generally reduced over the range of motion by embodiments of the invention simulated. Under the simulated conditions, force reductions in the range of about 100N were achievable at points within the gait cycle. FIG. 69 also plots the medial contact forces without the implant. The unshifted, generally upper line represents the simulation run without the implant and the shifted, generally lower line represents the simulation run with the implant.

Implants according to embodiments of the present invention may be configured and secured in a variety of ways as described below in more detail with respect to exemplary embodiments. In general, such implants may be rigid, semi-rigid or soft compliant prostheses secured to adjacent bone or the surrounding tissues. Implants also may be held in place by the surrounding tissues without using a fixation element. Soft compliant prostheses could be filled with water, saline, silicone, hydrogels, etc., sufficient to move the tissue laterally as described above. Such a soft compliant prosthesis could be placed in a deflated state and then inflated to the appropriate thickness. Alternatively, implants may be filled with other flowable materials including beads or other particles made of metal, polymer, or foam material, optionally in a liquid medium, which conform to the adjacent bone or tissue surfaces. Thixotropic materials, such as hydrogels derived from hyaluronic acid, change their mechanical properties as shear stress is applied to them. An implant filled with such materials could be made to change the amount of lateral displacement that it provides based on the shear stress that it sees from overlying target tissues at various points in the gait cycle. Implants may be coated with materials to reduce friction such as hydrophilic coatings or polytetrafluoroethylene (PTFE) coatings. Additionally or alternatively, the prosthesis may be adjustable to allow the dimensions such as thickness of the prosthesis to be adjusted during surgery or anytime after surgery. Rigid or substantially rigid prostheses could be made of known bone-compatible implant materials such as titanium or stainless steel. Whether rigid or compliant the surface of the prosthesis should be designed to minimize negative effects of movement of the connective tissues thereacross. Such prosthesis could be implanted arthroscopically or using a mini-open or open surgical approach.

An exemplary embodiment of a soft compliant implant is illustrated in FIG. 8. In this embodiment, implant 20 includes a body member 22 made wholly or partially of a soft compliant material such as described above. Body member 22 has an upper (laterally-facing) bearing surface 21 configured to slidingly engage the target tissue to be displaced. Bearing surface 21 thus forms a displacement portion of the implant. The bearing surface is preferably made or coated with a lubricious material such as PTFE or a hydrophilic material to reduce friction with the target tissue. Body member 22 is further shaped to enhance its ability to stay in the desired position with respect to the target tissue. In this regard, body member 22 has a generally hour glass-like shape with a thinner and narrower central section 24 and wider and thicker end sections 26 to follow the contours of the target tissues. Preferably, body member 22 is shaped such that upper bearing surface 21 forms a longitudinal trough or channel which guides and retains the target tissue on the bearing surface as it slides relative thereto. Accordingly, body member 22 may have greater thickness along its lateral edges than along its middle, or the lateral edges may be curved or bent upward to inhibit the target tissue from sliding off the edges of body member 22. Body member 22 is preferably shaped so as to slip under the target tissue and be self-retained in position due to compression between and friction with the adjacent tissues, without need for separate fasteners. Optionally, the lower side (opposite the upper bearing surface) may have friction-enhancing features such as bumps, scales, or projections which engage the underlying tissue to enhance retention, thus forming a fixation portion. As a further option, in order to further secure the implant in the desired location, attachment means such as holes 28 for fasteners such as sutures or straps may be provided on either or both ends of body member 22, or a flexible strap or band 29 configured to be wrapped around the target tissue may be coupled to or integrally formed with either the superior or inferior ends of body member 22. In one exemplary embodiment, an implant generally configured in the manner of implant 20 may be well suited for insertion under the iliotibial tract.

In another exemplary embodiment of the invention, as shown in FIG. 9, prosthesis 30 provides lateral displacement by inserting a passive, space-occupying implant under the target tissue as described above. Prosthesis 30 comprises a body member 32 that defines displacement portion 33 and fixation portion 34. Displacement portion 33 is the portion responsible for displacing the target tissues as required to accomplish the force redistribution. The medial surface of displacement portion 33 is preferably shaped to conform to the external shape of the lateral femoral condyle and may have a hook- or spoon-like shape on its distal end to wrap partially around the distal facet of the lateral femoral condyle. Displacement portion 33 is preferably rounded and smooth on its lateral side to provide a smooth surface over which the displaced soft tissues may slide. Fixation portion 34 is shaped so that it lies more flat under the muscles and tendons higher up the femur, away from the complexity of the areas adjacent to the femoral condyles, where many different tissues crossover and attachments to bone can occur. This more cranial segment of the femur would allow easier access to the underlying bone and potentially better fixation. Fixation could be achieved by any known means for bone-secured implants, such as bone screws 36, tacks, anchors or adhesives, to name a few possibilities. The implant could be made from any suitable material, either hard or soft materials. In this case, silicones of varying grades and durometers, titanium, stainless steel or pyrolytic carbon are examples of materials which would be appropriate choices.

In one alternative embodiment, depending on specific patient conditions, it may be desirable to directly secure the prosthesis to the femur in the condyle region. Prosthesis 40, shown in FIG. 10, illustrates an example of such a prosthesis. In this embodiment, the fixation and displacement portions are collocated within body member 42 closer to the condyles of the femur. The configuration of the body member with respect to its displacement function would be essentially the same as described above. Fixation would also be substantially as previously described, for examples screws 44 are illustrated, except that it is adapted to allow fixation and displacement functions to be collocated.

In various alternative embodiments, the displacement portion and the fixation portion of prostheses according to the invention may be of unibody construction, or may be formed of two or more parts depending on desired function. For example, the fixation portion may be stainless steel or titanium textured to enhance bony ingrowth and solid screw fixation, while the bearing/displacement portion could be made of a different material, for example, pyrolytic carbon to enhance the ability of overlying tissues to slide across the implant, or PTFE, silicone or other low-friction polymer with suitable wear characteristics to provide a softer bearing surface. In further alternatives, the displacement portion could be comprised of a substrate of one material with an overlying layer forming the bearing material. The substrate could be either attached to or contiguous with the fixation portion.

The fixation and displacement portions may be in-line with one another, or they may be offset from one another, or a combination of both with multiple displacement portions. Alternative exemplary embodiments in this regard are illustrated in FIGS. 11-13B. For example, prosthesis 50 in FIG. 11 includes a base member 52 that is configured to position displacement portion 53 anteriorly with respect to fixation portion 54. Base member 52 thus has a generally straight section configured to be mounted to the femur and a curved section that extends anteriorly from the straight section when implanted. Displacement portion 53 is attached to the curved section and extends inferiorly so as to be positioned beneath the target tissues adjacent the lateral femoral condyle. In this embodiment, displacement portion 53 may have on either or both the medial and lateral surfaces thereof a bearing surface 56 of a different lower friction material than that of the remainder of the bearing portion 53. Alternatively, base member 52, the displacement portion 53, and/or the bearing surface 56 may be the same material, and may be of unibody construction. Fixation holes 58 are provided in the fixation portion to receive screws for attachment to the bone.

Figure 12:
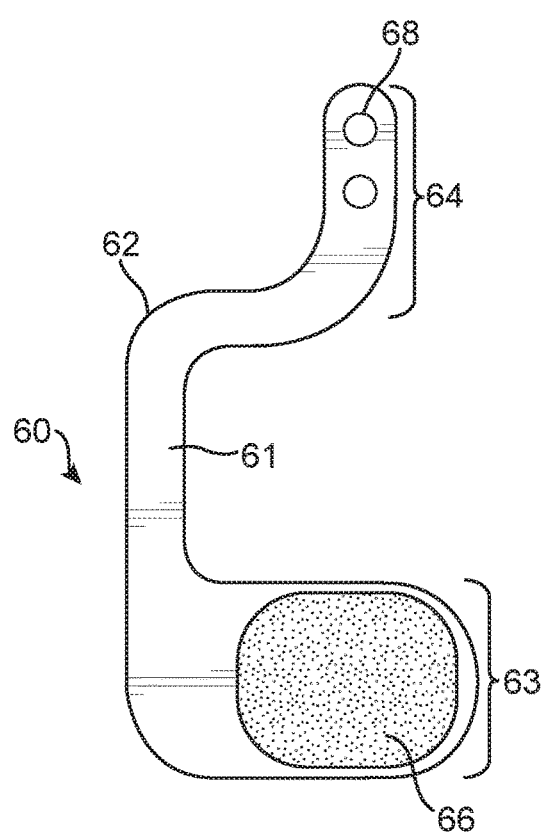

Prosthesis 60 provides another exemplary embodiment, shown in FIG. 12, which includes base member 62 having a spanning section 61 between displacement portion 63 and fixation portion 64. Once again, fixation holes 68 are provided as one alternative fixation means, and a separate bearing surface 66 may be provided. Alternatively, base member 62 and the displacement portion 63 may be the same material, and may be of unibody construction. In this embodiment, spanning section 61 extends generally vertically between the fixation portion 64 and displacement portion 63 and is offset posteriorly with respect to both the fixation portion 64 and displacement portion 63 in order to avoid critical anatomical features adjacent the joint. Depending on specific joint anatomy and patient conditions, the spanning section may be designed to permit secure fixation at a suitable site while still placing the displacement portion under the target tissue while minimizing trauma to important intervening tissues.

Figure 13:
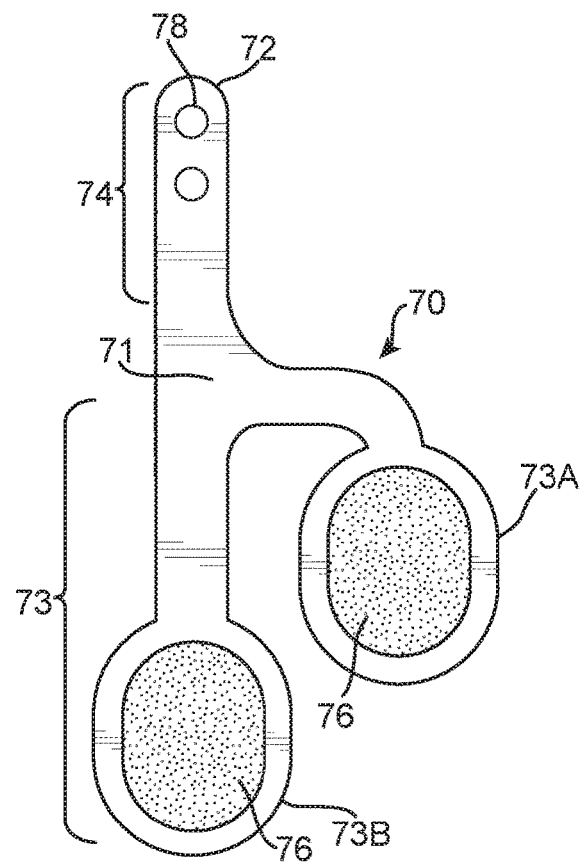
Figure 13A:
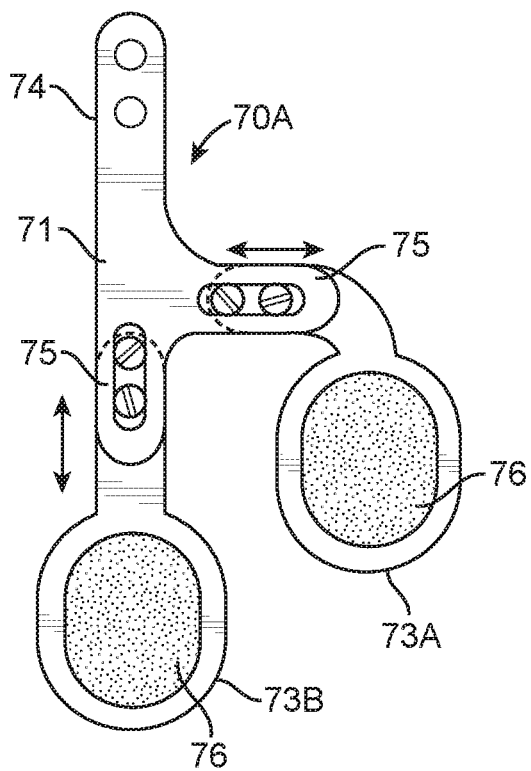
Figure 13B:
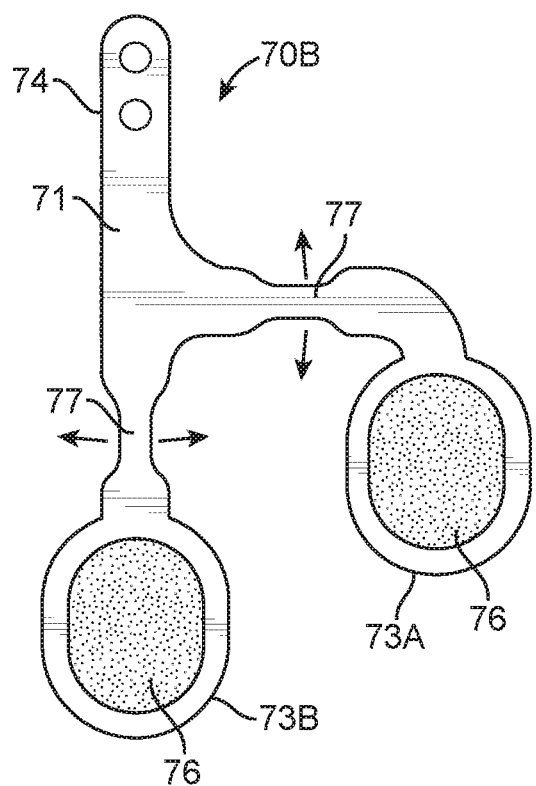

In yet another exemplary embodiment, multiple displacement portions may be provided as shown in FIG. 13. For example, prosthesis 70 includes base member 72 that defines anterior displacement portion 73A and posterior displacement portion 73B. These are joined by spanning section 71 to fixation zone 74 where fixation holes 78 are located. In this embodiment, each of displacement portions 73A and 73B includes a bearing surface 76. Again, the bearing surface may be integral, or attached to the base members. Further, in this or any other embodiment herein, the displacement portions 73A, 73B may be movably coupled to the spanning section 71 or fixation zone 74 by means of a rotatable or slidable coupling 75, for example as shown in FIG. 13A, thereby being movable with joint motion. Alternatively, spanning section 71 or the joints between it and the displacement portions may include flexible portions 77 so as to deflect in response to joint movement, as shown in FIG. 13B. In a further alternative, the flexible portion 77 may be malleable to allow the surgeon to deform and/or reposition displacement portions 73A, 73B to a desired configuration before or after the prosthesis has been fastened in place. As yet another alternative, the couplings between the displacement portions and the spanning section 71, or between the spanning section and the base member 72, may be movably adjustable to allow the surgeon to position the components in various locations relative to one another and fix them in any such position.

As illustrated above, the displacement portion of prostheses according to embodiments of the present invention may have any number of different shapes as desired to cooperate with specific target tissues as needed for the pathology of a given patient. In further examples, more complex geometries may be provided in order to vary the target tissue displacement in coordination with the patient gait cycle and loading conditions created throughout the cycle. For example, the bearing surface may be configured to provide relatively little tissue displacement and force realignment as the knee is flexed through the gait cycle, but to deflect the target tissues more as the knee is extended fully during the gait cycle, providing the necessary correction appropriate for that pathology. This feature can be achieved by optimizing implant static geometry, by enabling dynamic changes in implant position or geometry depending upon joint position or loading, or as previously mentioned, by selection of certain implant materials. For instance, the outer shell of an implant could be a resilient material such as silicon, filled with a thixotropic fluid. During the gait cycle, the shear stress exerted on the implant causes the viscosity of the thixotropic filler to drop, allowing the fluid to flow to the sides of the implant, and causing less displacement. As the knee is extended fully in the stance phase of the gait cycle, the resilient shell of the implant urges the thixotropic fluid back into its original position, whereupon the viscosity increases again to provide greater displacement.

Figure 4:
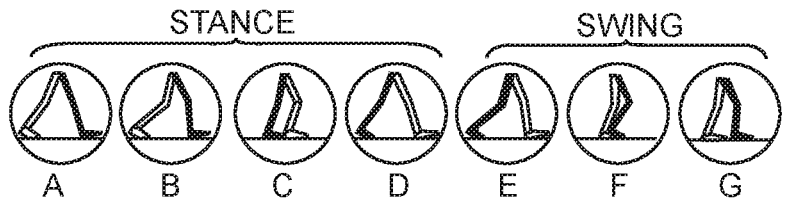
FIG. 4 is a schematic diagram illustrating the human gait cycle, knee joint moment and flexion angles within the gait cycle, and including a sequence diagram illustrating the position of connective tissue through the gait cycle with respect to an exemplary embodiment of the present invention.
Figure 4:
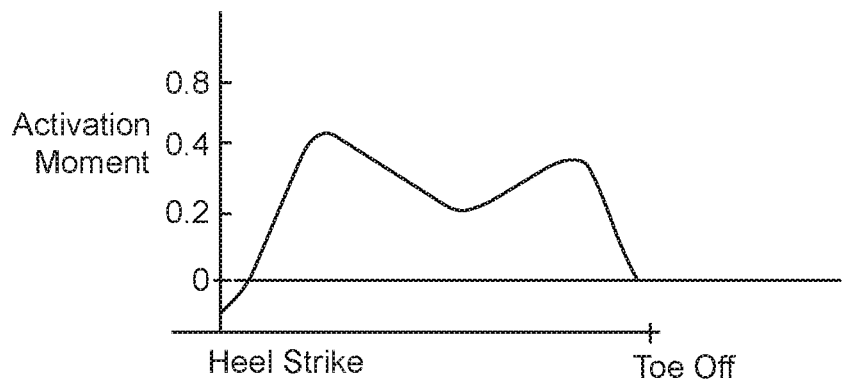
Figure 4:
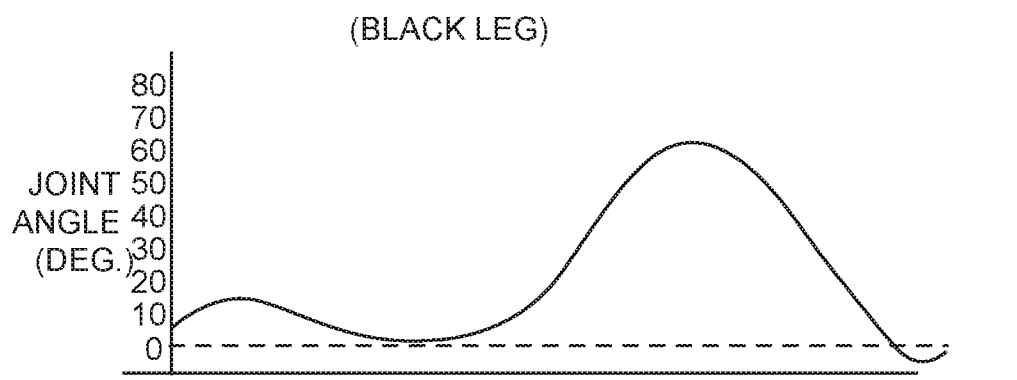
Figure 4:
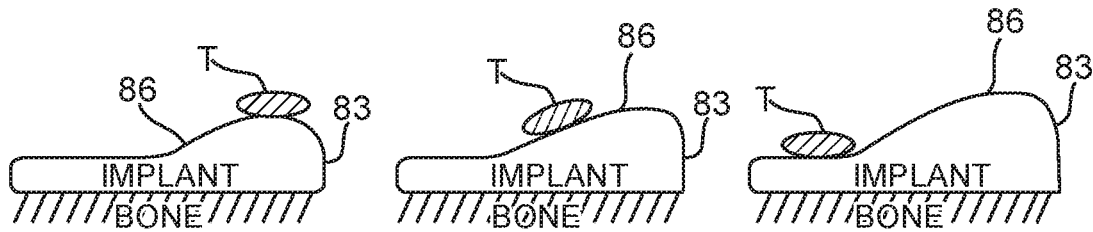

One exemplary embodiment showing the more complex geometry referred to above is shown in FIG. 4, which was referred to previously in the explanation of the gait cycle. Shown at the bottom of FIG. 4 is a transverse cross-section through the displacement portion 83 of an exemplary prosthesis, which may have an overall configuration such as, for example, the configuration of prosthesis 60 in FIG. 12. In other words, displacement portion 83 in FIG. 4 is viewed from a cranial aspect towards the caudal aspect. Bearing surface 86 provides a ramped surface with lesser thickness dorsally, increasing in the ventral direction. The bearing surface is thus configured such that during the gait cycle the displaced target tissues T slide ventrally and dorsally there along. As shown in the first graph of FIG. 4, the adduction moment acting medially on the knee occurs during the stance phase when leg is loaded. During this phase, the joint angle is generally in the range of about 0° to about 20°, with the greatest forces being applied when the knee is straight or close to straight. Thus, to provide maximum effect, bearing surface 86 is configured so that target tissue (T) is at an area of maximum displacement when the joint angle is in the range of about 0°-10°, lesser displacement at an area where the target tissue (T) resides at joint angles in the range of about 10°-20° and minimal displacement when the joint angle exceeds about 20°.

The geometry shown for displacement portion 83 in FIG. 4 is idealized for the gait cycle when walking on a flat surface. In reality, walking occurs on uneven ground and up and down stairs, which can cause substantial loading on the knee at joint angles greater than about 20°, such angles usually being less than about 60°, but in most cases not at angles greater than about 90°. Thus specific geometries for the bearing portion may need to be designed with particular patient needs in mind.

Figure 14:
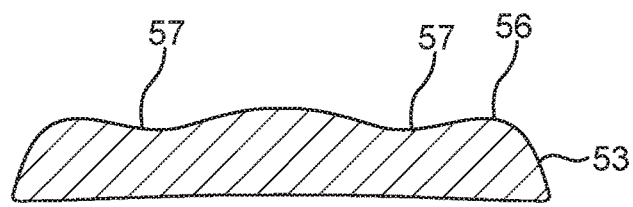
FIG. 14 is a cross-sectional view through line 14-14 of FIG. 11 showing a bearing/displacement portion of a prosthesis according to another exemplary embodiment of the present invention.

Another complex geometry is shown in FIG. 14. In this alternative embodiment, displacement portion 53 of prosthesis 50 (FIG. 11) is provided with bearing surface 56 having grooves 57, or other variations of the bearing surface geometry to fit the anatomical track and motion of the target tissue as the joint moves through the gait cycle, thus optimizing the force distribution created by the prosthesis at each joint position.

Figure 15:
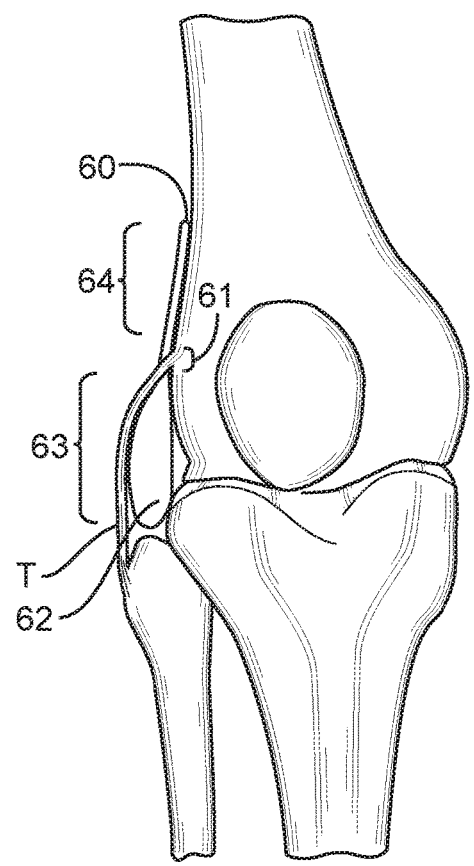
FIG. 15 is an anterior view of a right knee joint with a prosthesis according to an exemplary embodiment of the invention implanted thereon.
Figure 16:
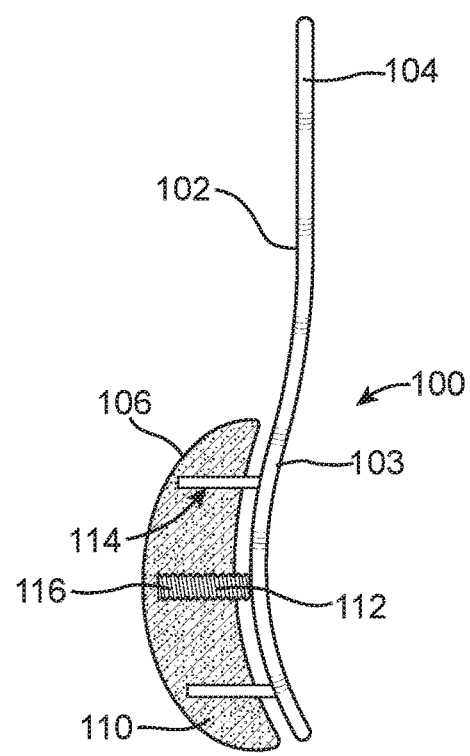
FIGS. 16, 17, 17A, 18 and 19 are schematic side views and a detailed view of further alternative embodiments of the present invention incorporating adjustable bearing members.

FIG. 15 illustrates an exemplary implantation of a prosthesis according to the present invention, in this case implant 60 shown above in FIG. 12. In this example, implant 60 is used to displace the fibular collateral ligament. A similar implant and positioning is depicted as implant 10E in FIG. 2. In other instances, the implant may be configured to displace other muscles or tendons such as the biceps femoris tendon (as positioned by implant 10B in FIG. 2) or the iliotibial band. With reference again to FIG. 15, fixation portion 64 of implant 60 is attached to the femur so that base member 62, including displacement portion 63, extends caudally beyond the end of the femur to at least partway across the joint space. With spanning section 61 posteriorly positioned, the device is shaped to jog around the attachment point(s) of surrounding tissues (including potentially the target tissues) and allow fixation portion 64 to be situated above the attachment area on the femur. More specifically, spanning section 61 circumvents the attachment sites of the plantaris muscle and the lateral head of the gastrocnemius muscle. Both the plantaris muscle and the lateral head of the gastrocnemius muscle attach to the posterior of the lateral femur. By having a posteriorly offset spanning section 61, the implant avoids these attachment sites and allows the bearing surface 66 (see FIG. 12) to laterally displace the collateral ligament. Once again, displacement portion 63 may be shaped so that target tissue (T) track is displaced at a position such that contraction forces of the target tissue (T) are predominantly in the direction normal to the bearing surface of the joint, such that minimal or no moment arm and torsion is created. This will help to reduce or prevent any undesired forces onto or micromotion of the device, which could result in loosening of the fixation of the device over time.

In other exemplary embodiments of the invention, shown in FIGS. 16-19, prostheses according to the invention are adjustable to increase or decrease the amount of displacement exerted on the target tissues either during implantation or post surgery via a simple percutaneous access. For example, prosthesis 100, shown in FIG. 16, includes a base member 102 with a moveable bearing member 110 mounted within the displacement portion 103. Fixation portion 104 extends superiorly from the displacement portion for fixation to the femur substantially as previously described. Bearing member 110 has an outer bearing surface 106 also substantially as previously described. Bearing member 110 may be secured to base member 102 by adjustment means such as screw 112 and alignment posts 114. Other suitable adjustment means, such as ratcheting posts, sliding posts with separate locking means or other means for providing the adjustment, may be applied by persons of ordinary skill in the art. Access port 116 through bearing surface 106 allows access of a tool to rotate screw 112 to adjust the bearing member in (medially) or out (laterally) with respect to the base member, thus adjusting the magnitude of displacement of the target tissue. Persons of ordinary skill in the art will also appreciate that any of the adjustability features described herein may be incorporated with any of the geometries described above.

Figure 17:
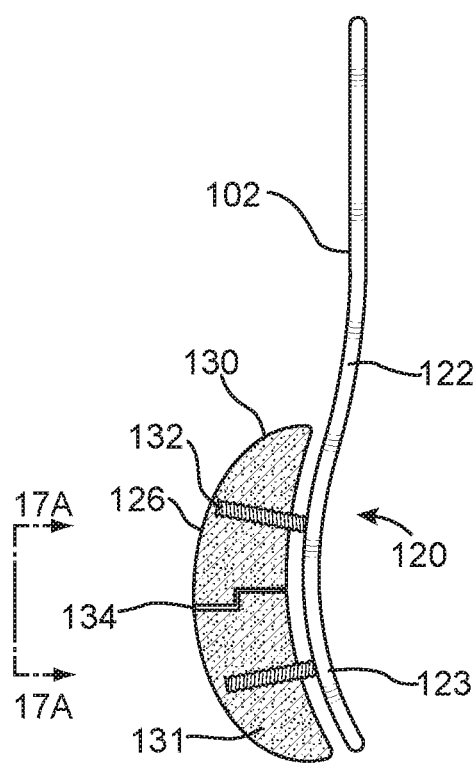

Prosthesis 120 in FIG. 17 illustrates another exemplary embodiment, including a base member 122 with bearing members 130, 131 adjustably attached in displacement portion 123. While this exemplary embodiment includes two adjustable bearing members, persons of ordinary skill in the art will appreciate that more parts of the displacement portion may be provided to accommodate the desired adjustability for the desired geometry. In this embodiment, screws 132 are once again used as the adjustment means. However, it will again be appreciated that other means of adjustment could be provided.

Figure 17A:
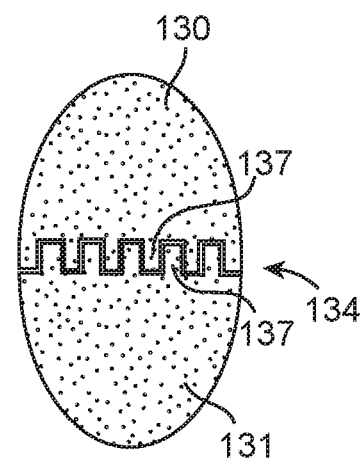

Given the curved shape of the bearing surface 126 and the separate adjustment points, prosthesis 120 includes an expansion joint 134 between the two bearing members 130, 131 to accommodate the separation of the bearing members in view of the adjustability feature. While the two or more bearing members could simply separate to leave a small gap between them as they are adjusted outward from their minimum displacement position, it may be desirable to provide a relatively smooth, relatively contiguous bearing surface 126 as the adjustment and displacement is increased. As shown in FIG. 17A, interlaced fingers 137 of expansion joint 134 help prevent the formation of large gaps that could pinch or grab the target tissue as it moves across the bearing surface. Alternatively, the bearing surfaces of bearing members 130, 131 could be covered with a single membrane of suitably elastic low-friction material extending across the gap between the members which could resiliently expand or contract with adjustments in position of the bearing members.

Figure 18:
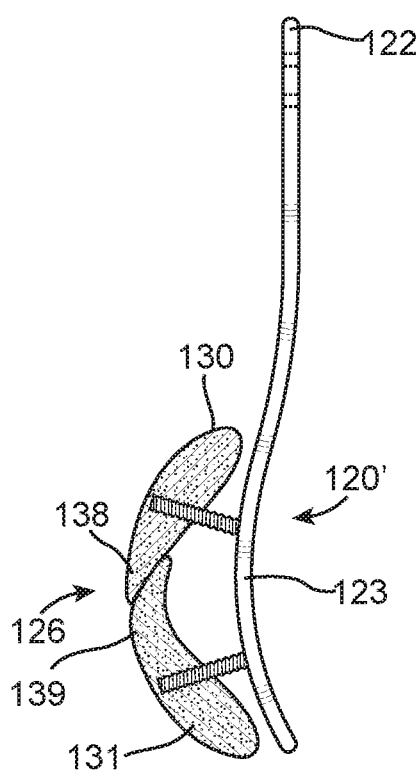

In a further exemplary embodiment, prosthesis 120' in FIG. 18 is substantially the same as prosthesis 120 described above except for the configuration of expansion joint 134. In this exemplary embodiment, rather than interlaced fingers, expansion joint 134 utilizes bearing members 130, 131 with overlapping tapered ends 138, 139, respectively, which slide relative to one another to form a smooth bearing surface 126 free of gaps providing a smooth overlapped expansion zone.

Figure 19:
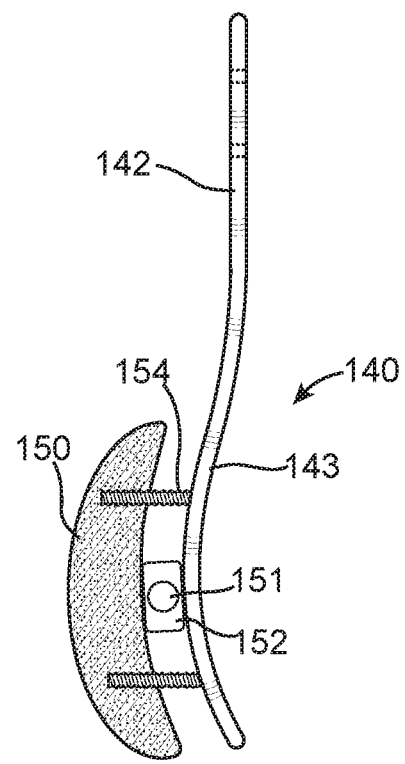

In a further alternative embodiment, prosthesis 140 provides an adjustment mechanism that is accessed from the anterior and/or posterior (A/P) aspect of the knee, as shown in FIG. 19. In this embodiment, base member 142 has two alignment posts 154 that extend from the displacement portion 143. Bearing member 150 receives the alignment posts. One or more slideable wedge members 152 are disposed between the bearing member 150 and base member 142 between posts 154 and are movable posteriorly and anteriorly relative to base member 142 and bearing member 150. Actuating screws 151 or other adjustment devices move the wedges in and out underneath the bearing surface, which slides the bearing surface more or less laterally relative to the base member, thereby adjusting the displacement of the target tissues.

In various adjustable embodiments described above, the adjustment screws themselves may be radiopaque and/or otherwise discernable from the rest of the implant under x-ray in order to enable post-surgical percutaneous adjustment of the device. Alternatively, target features can be built into the device to locate the adjustment points without having the screws or adjustment means themselves radiopaque, such as radiopaque rings or markers built into the nearing surface of the device itself.

In still further alternative embodiments, the bearing members of embodiments described herein may be movable by means of an inflatable bladder disposed between the bearing member and the base member. The bladder may be filled with a liquid or gas under suitable pressure to allow adjustment of the bearing member position and associated displacement of the target tissue. The bladder will have an inflation port for introduction of inflation fluid by means of an inflation device, which may be similar to the inflation devices used for inflation of angioplasty balloons.

Devices described above generally disclose placement of a device on the femoral side of the femoral patellar joint. Devices in accordance with embodiments of the invention may also be placed on the tibial side to laterally displace the target tissues by being fixed on the tibia or the fibula. An exemplary tibially-fixed implant is shown in FIG. 20.

Figure 20:
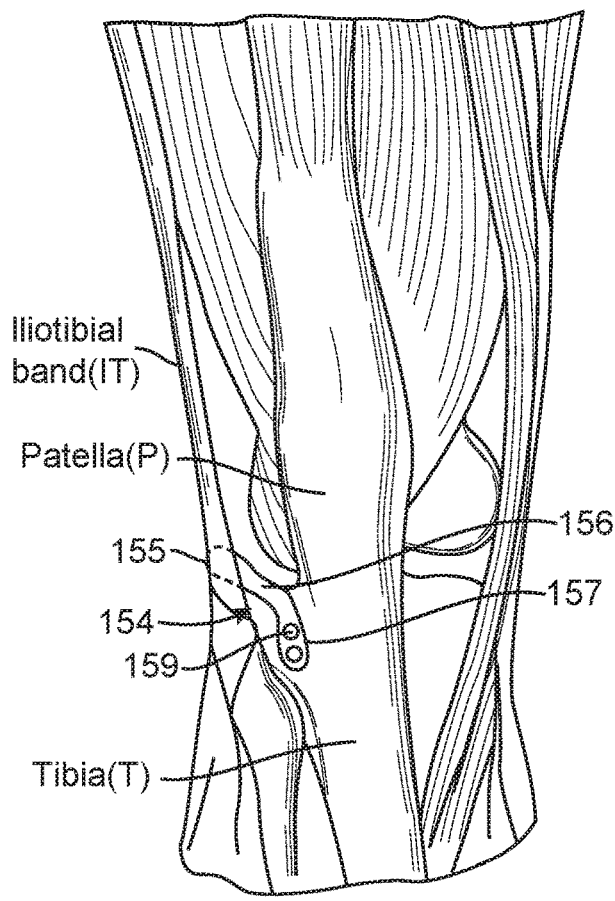
FIG. 20 is an anterior view of a human knee illustrating positioning of another exemplary embodiment of the present invention for addressing lateral force distribution in the knee.

Referring to FIG. 20, implant 154 is inserted underneath the iliotibial band (IT) just superior to Gerdy's tubercle, to move the iliotibial band laterally and/or anteriorly, implant 154 includes a displacement portion 155, spanning section 156 and fixation portion 157 as previously described. Bone screws 159 may be placed through holes in the fixation portion to secure the implant to the tibia. Other fixation means as described herein may be alternatively employed. Implant 154 may be positioned as shown to rebalance dynamic loading on the knee joint in a lateral and/or anterior direction. It may reduce symptoms and progression of medial osteoarthritis in the knee. It may also improve the strength and stability of the knee, by giving the muscles which act on the iliotibial band greater leverage. It will be understood that implant 154 may also be configured to displace muscles, tendons, or tissues other than the iliotibial band, including the biceps femoris short head, biceps femoris or fibular collateral ligament, among others.

A further advantage of implant 154, positioned as shown, may be to reduce the incidence and/or severity of Iliotibial Band. Syndrome. Iliotibial Band Syndrome, or Iliotibial Band Friction Syndrome, typically occurs because the iliotibial band is rubbing against the lateral femoral epicondyle, the femur or other tissues on the lateral side. Thus, embodiments of the invention also may be used for treatment of conditions involving excessive friction or pressure between tissues in the knee or other joints, alone, or in combination with osteoarthritis treatment. By moving the iliotibial band laterally and/or anteriorly, the pressure of the iliotibial band against these tissues may be relieved.

For placement of implant 154, surgical dissection of the iliotibial band could be made from the posterolateral edge or the anteromedial edge of the iliotibial band. However, it may be preferable to make this dissection from the anterolateral edge, between Gerdy's tubercle and the tibial tuberosity. Fixation portion 157 could then be attached to the tibia underneath the muscle which runs between these two tuberosities.

Figure 21:
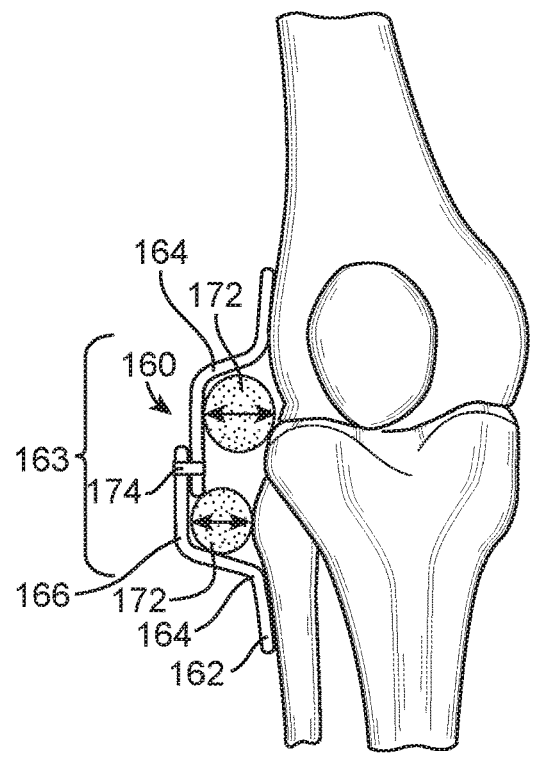
FIG. 21 is a view of a knee joint with a joint spanning prosthesis according to another exemplary embodiment of the present invention.

It will be understood that while many embodiments described herein are described as being secured to only one of the two bones associated with a joint, embodiments also may be secured to both of the bones. For example, in the case of the knee, to both femur and tibia or femur and fibula. In another exemplary embodiment, shown in FIG. 21, prosthesis 160 spans the entire joint and is fixed to both the femur and either the tibia or fibula, depending on geometry. Prosthesis 160 is provided with a sliding hinge 174 or other suitable articulated joint to allow freedom of movement of the joint. More specifically, in this exemplary embodiment, base member 162 includes upper and lower fixation portions 164 with displacement portion 163 disposed between and including sliding hinge 174. Displacement of the target tissues is once again provided by bearing surface 166 across which the target tissue tracks. The bearing surface may be made adjustable by providing a separate bearing member and adjustment mechanism as described above. Displacement may also be controlled by an additional or alternative displacement means as shown in FIG. 21. In this embodiment, one or more expansion members 172 are deployed under base member 162. Expansion member 172 may comprise an inflatable device such as a balloon or a mechanical adjustment such as a screw mechanism. The expandable member(s) 172 may be positioned so as to exert force on only the femur or only on the tibia or fibula, or positioned more centrally along the joint to exert force on both femur and tibia. The sliding members making up the displacement portion 163, or the regions where these members join to the upper and lower fixation portions 164, may be flexible so that the bearing displacement portion 163 is deflectable laterally with expansion of expansion members 172, thereby increasing the displacement of target tissues.

In other embodiments of the invention, joint disorders related to forces in other planes such as the lateral plane may be addressed. The biomechanics of the knee in the coronal or frontal plane have been described above, with a variety of embodiments generally in a medial/lateral direction to address imbalanced loads at the interface of the femoral and tibial articular surfaces. Looking at the knee in the lateral plane, there is a different set of force components that act anteriorly and posteriorly, resulting in loading between the patella and femur.

Figure 22:
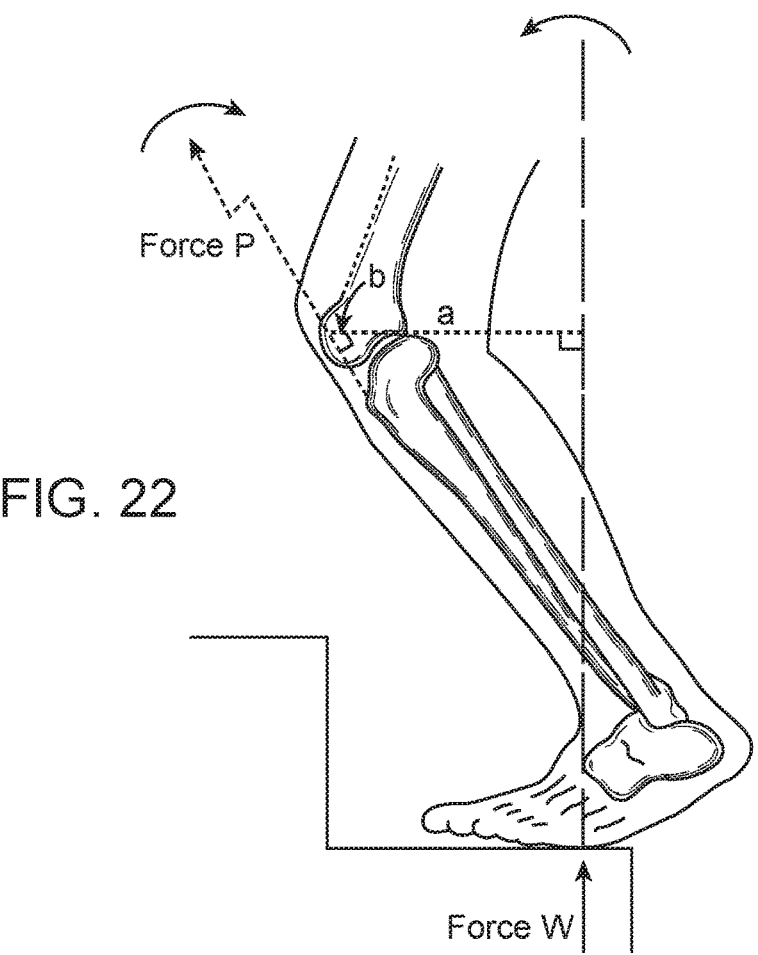
FIG. 22 is a free body diagram of a human knee joint during stair climbing.

With reference to the free body diagram in FIG. 22, the two main moments acting around the knee joint are due to the ground reaction force W and the patellar tendon force $F_p$. The flexing moment on the lower leg is the product of the ground reaction force (W) and the perpendicular distance of the force from the center of motion of the knee joint, (a). The counterbalancing extending moment is the product of the quadriceps muscle force acting through the patellar tendon and its lever arm, (b). Hence, for a given individual, the magnitude of the patellar tendon force $F_p$, can be calculated as $F_p = Wa/b$.

Figures 23A, 23B:
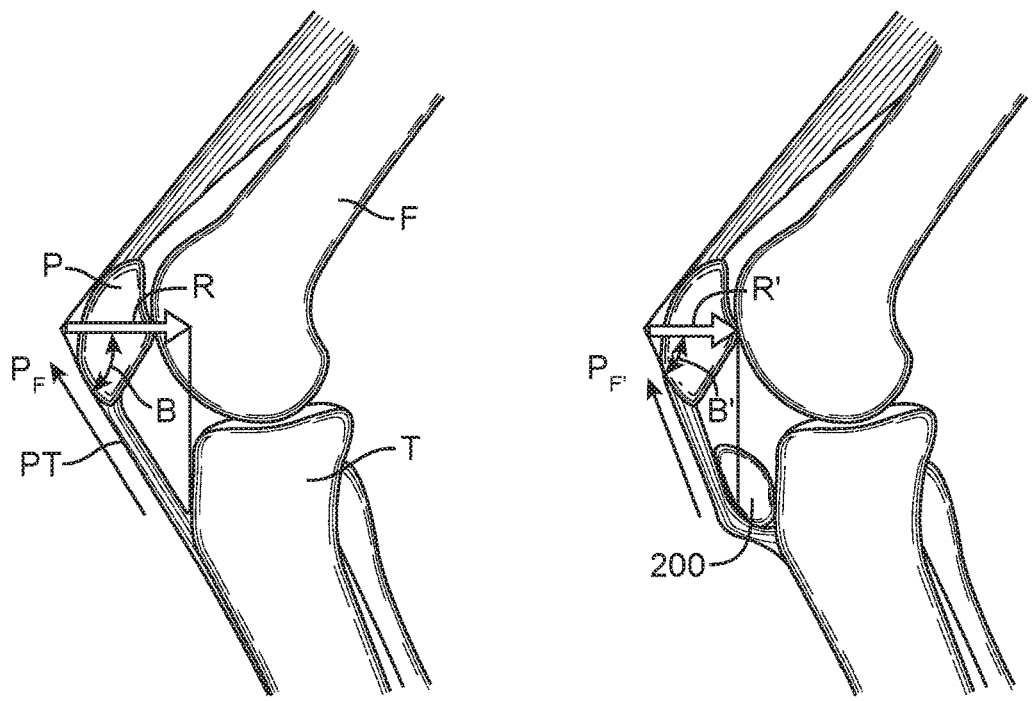
FIG. 23A is a free body diagram of a human knee showing the resultant patellar compression force in a normal knee.
FIG. 23B is a free body diagram of a human knee showing the modified resultant compression force with an exemplary embodiment of the present invention.

The action of the quadriceps muscle and the patellar tendon on the patella during flexion/extension results in a patellar compression force (PCF), as shown in FIG. 23A. The resultant (R) PCF is dependent on the magnitude of P and its effective angle of action ($\beta$).

Referring to FIG. 23B, resultant force R' is decreased by positioning implant 200 under the patellar tendon, thus displacing it anteriorly to increase the lever arm b (FIG. 22), thereby reducing the patellar tendon force $F_p$, and increasing the effective angle of action $\beta'$, thereby reducing the horizontal component of the patellar tendon force corresponding to the PCF. The resultant PCF (R') is thus reduced, lessening the force with which the patella is pressed against the femur.

Anticipated advantages of this embodiment of the present invention include a reduction in the rate of cartilage degeneration and/or pain in this area. An implant such as implant 200 may be configured to redistribute the point of highest load between the patella and femur superiorly, caudally, laterally or medially so as to reduce the stress on any specific area of that interface. It should also increase the moment arm of the muscles acting on the patellar tendon, thereby providing greater effective strength and stability to the knee, and lowering the total load on the knee joint.

Figure 24:
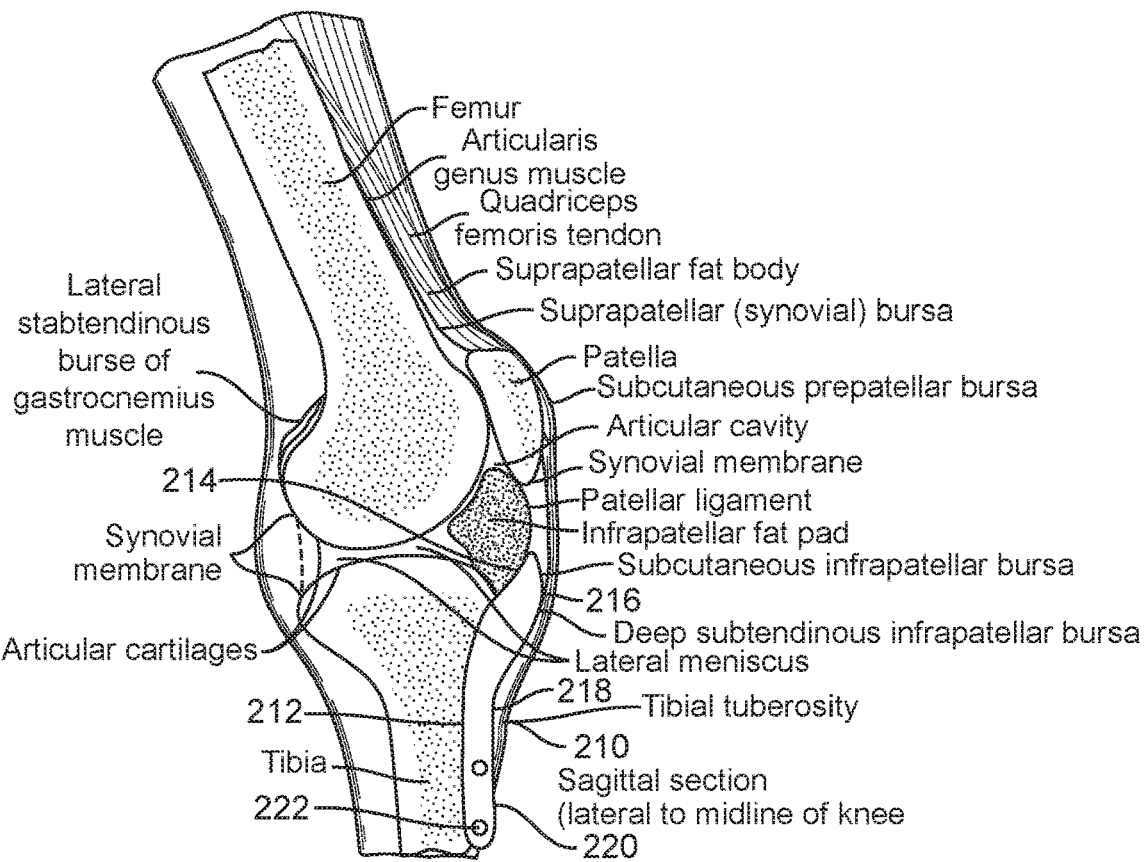
FIG. 24 is a sagittal section of a human knee with an exemplary embodiment of the present invention implanted thereon to reduce patellar compression force.
Figure 25:
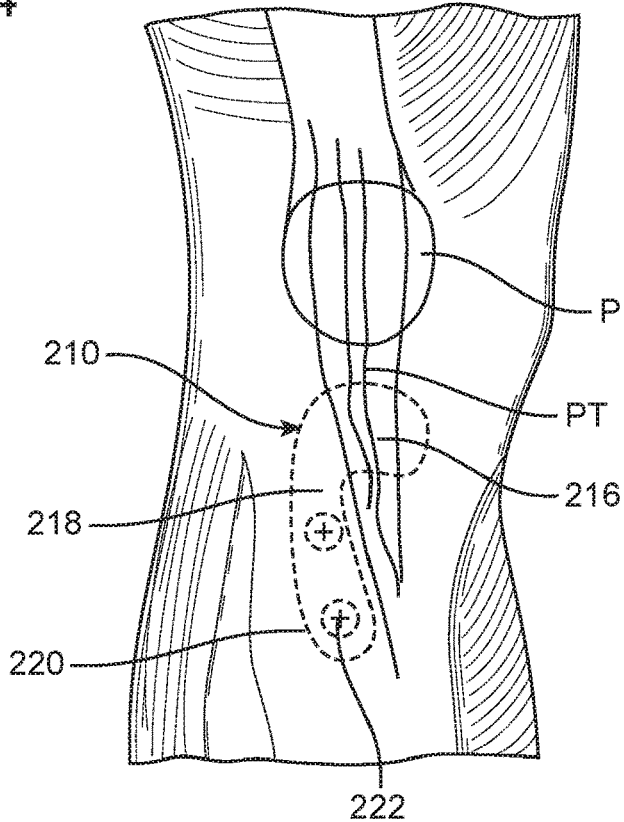
FIG. 25 is an anterior view of a human knee illustrating the exemplary embodiment of FIG. 24 as disposed under connective tissues.

One exemplary embodiment is illustrated in FIGS. 24 and 25, which show implant 210 placed on the tibia to displace the patellar tendon without cutting the tibial tubercle or severing any of the connective tissues as described above. As with other embodiments described herein, implant 210 comprises support member 212 and bearing member 214, which in this case are integrally formed but may be separate components as elsewhere described herein. The support and bearing members are functionally divided into displacement portion 216, which engages and displaces the patellar tendon, spanning section 218 and fixation portion 220. Fixation portion 220 includes means for securing the implant as described herein. In this exemplary embodiment, holes are provided for bone screws 222 in order to fix the implant against the tibia.

As illustrated in FIG. 25, implant 210 may be inserted from the lateral side of the patellar tendon. It could also be inserted from the medial side. Implant 210 is configured such that fixation portion 220 lies in an area that does not have tendon insertions or other connective tissue attachment points. The configuration also may permit displacement portion 216 to rest against the tibia just cranial to the tibial tubercle and just caudal to the knee capsule. Such positioning will transfer any load directly to the tibia below the implant, thereby minimizing the stresses on the rest of the implant and the tibia itself.

The inner surface of fixation portion 220 that rests against the tibia, as with other embodiments described herein, may be designed and manufactured with the appropriate materials and textures to encourage ingrowth of bone into the implant, to provide more support and prevent motion of the implant relative to the bone surface to which it is secured; in this case the tibia. Spanning section 218 should be designed to experience relatively low stresses, and may therefore be fairly thin, to avoid creating an initiating or unsightly bump. Round, channeled, box-shaped, curved or other cross-sectional geometries may be selected to enhance bending stiffness or torsional rigidity as needed for spanning section 218. Again, spanning section 218 should not interfere with any of the muscle insertion points in the area of the tibial tubercle.

Displacement portion 216 is configured and dimensioned to avoid the knee capsule and to avoid interfering with the patella, even when the leg is extended. It should also be designed to minimize any additional stress on the patellar tendon itself. Therefore the bearing surface of displacement portion 216, against which the patellar tendon rests, may have a curved ramped shape as best seen in FIG. 24. This bearing surface may be hard and smooth, made from materials such as polished pyrolytic carbon, steel, or titanium, or coated or covered with a lubricious material, such as PTFE. It might alternatively be designed to encourage adhesion and ingrowth of the patellar tendon onto this surface, so that the implant acts even more as an extension of the tibial tubercle. For example the surface may be porous, roughened, or configured with openings into which bone or scar tissue may grow to enhance adhesion.

The precise positioning of the patellar tendon accomplished with implant 210 will depend upon the particular clinical situation. As will be appreciated by persons of ordinary skill in the art, such implants may be designed to move the patellar tendon anteriorly or medially or anterior-medially. This may be accomplished by making one side (lateral or medial) of the displacement surface higher than the other, and/or by forming a track with ridges on one or both sides of the bearing surface to urge the patellar tendon in a lateral or medial direction.

Implants such as implant 210 may be inserted in a relatively quick procedure with low morbidity. A relatively short incision could be made to one side of the tibia tubercle. From this incision a probe could be used to tunnel under the patellar tendon and expose the surface of the tibia underneath. The implant could then be inserted into this tunnel, fitted against the tibia, attached to the tibia with the appropriate screws or other fixation elements as appropriate, and then the incision could be closed. Since there is little or no cutting of bone, muscle, or tendon, morbidity should be minimal, and the recovery and rehabilitation after this procedure should be rapid and involve much less pain when compared with the existing surgical options.

An implant similar to implant 210 may also be applied in other anatomical locations. For example, on the anterolateral aspect of the tibia is Gerdy's tubercle, the insertion site of the iliotibial band. An implant such as implant 154 described above may be positioned in this location. Additionally, it may be preferable in some patients to displace both the patellar tendon and the iliotibial band. This could be done with two separate implants, such as implants 154 and 210 as described above, or a single implant could be provided.

Figure 26:
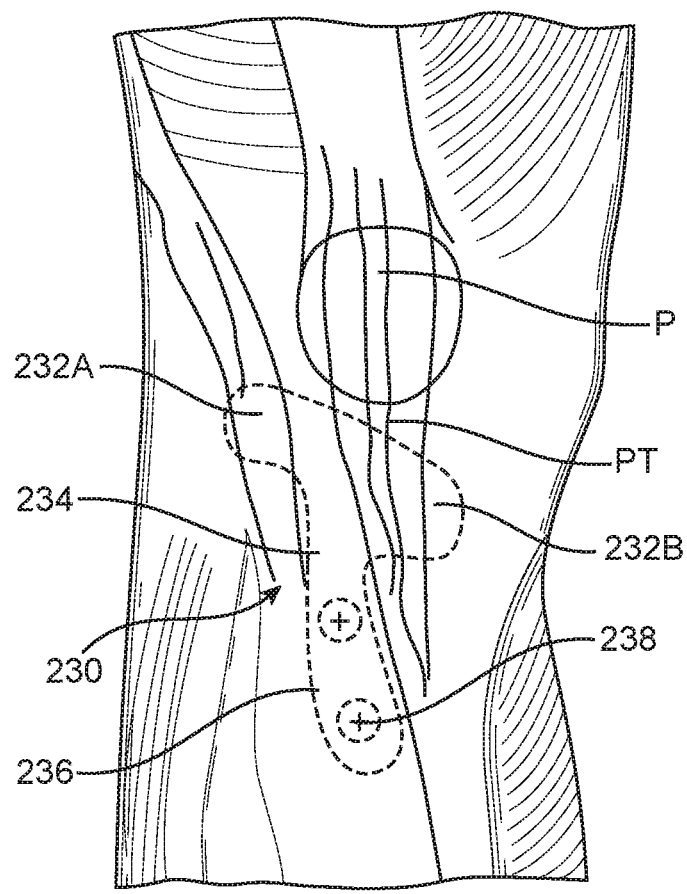
FIG. 26 is an anterior view of a human knee illustrating positioning of a further exemplary embodiment of the present invention for addressing both lateral force distribution and patellar compressive force as disposed under connective tissues.

An example of a single implant for displacing both the patellar tendon and iliotibial band is shown in FIG. 26. In this exemplary embodiment, implant 230 again includes a displacement portion 232 divided into two parts, iliotibial band displacement portion 232A and patellar tendon displacement portion 23213. Spanning section 234, formed as described above, joint displacement portion 232 to fixation portion 236. Again, a variety of fixation means as described herein may be employed by persons skilled in the art, with bone screws 238 being illustrated in the exemplary embodiment. A single implant such as implant 230 may provide greater strength and stability as compared to the use of two separate implants such as implants 154 and 210.

In general, materials, alternative configurations and methods related to implants 210 and 230 may be as described elsewhere herein for other exemplary embodiments.

Figure 27:
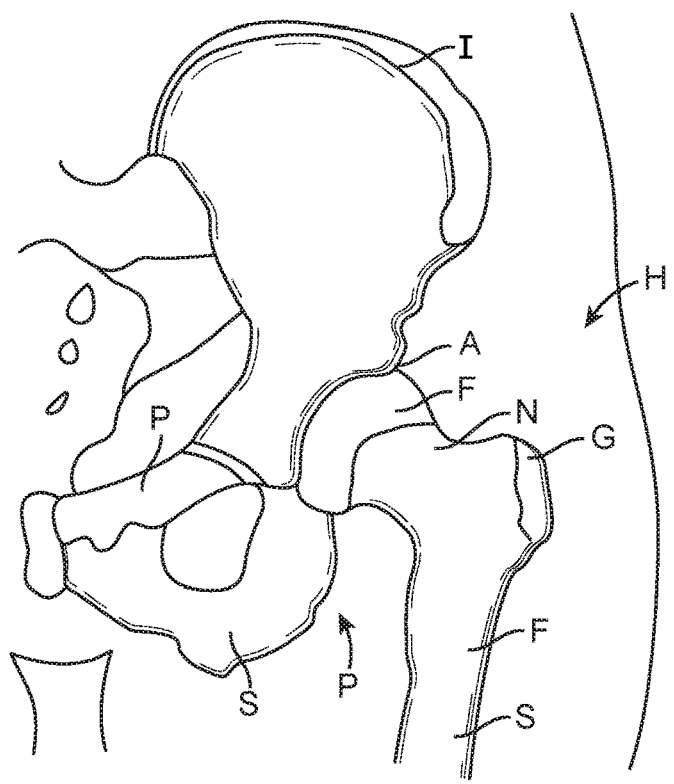
FIG. 27 is a front view of a right side of a hip, showing connection of the hip to the femur, and with ligaments removed to show detail.
Figure 28:
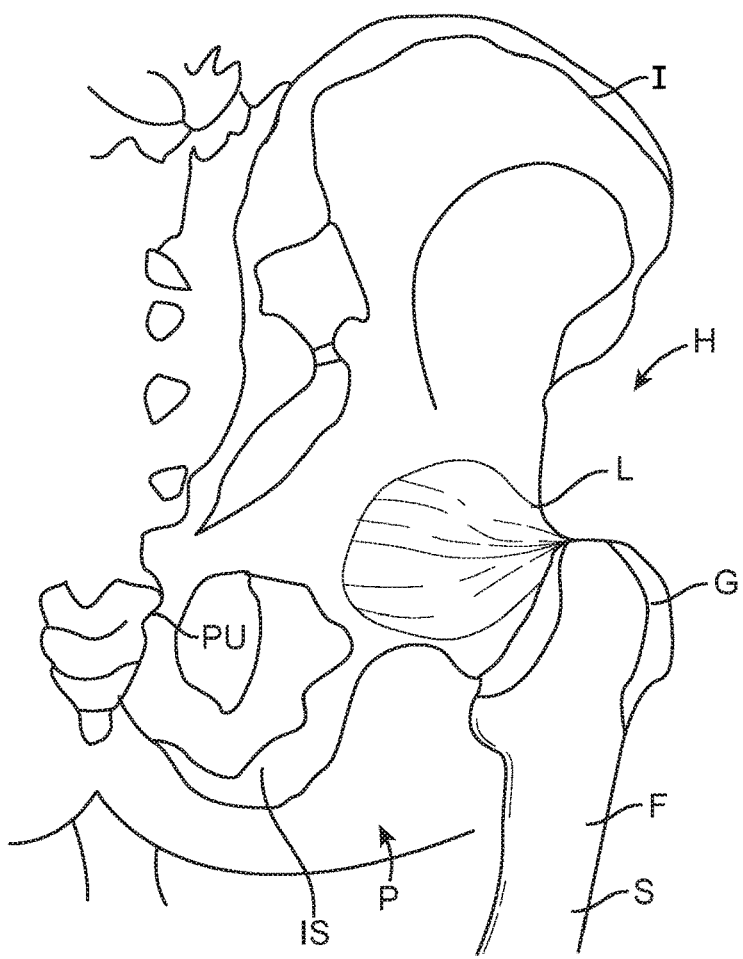
FIG. 28 is a posterior view of the hip of FIG. 27, with ligaments in place.

As mentioned above, further alternative embodiments of the present invention have application in the treatment of disorders of the hip. FIG. 27 illustrates the basic anatomy of a hip joint H. As shown, the hip joint H is the joint between the femur F and the concave cavity of the pelvis P, called the "acetabulum" A. The femur F extends upward from a knee of a body, and includes a greater trochanter G at an outer top edge at the juncture of the shaft S of the femur and the femoral neck N. A lower trochanter is located opposite the greater trochanter G, and a femoral head FH is located at the distal end of the femoral neck N. The concave-shaped acetabulum A forms at the union of three pelvic bones: the ilium I, the pubis PU and the ischium IS. A blanket of ligaments L (removed in FIG. 27 to show detail; shown in FIG. 28) covers the hip joint H, forming a capsule and helping to maintain the femoral head FH in the acetabulum A.

Figure 29:
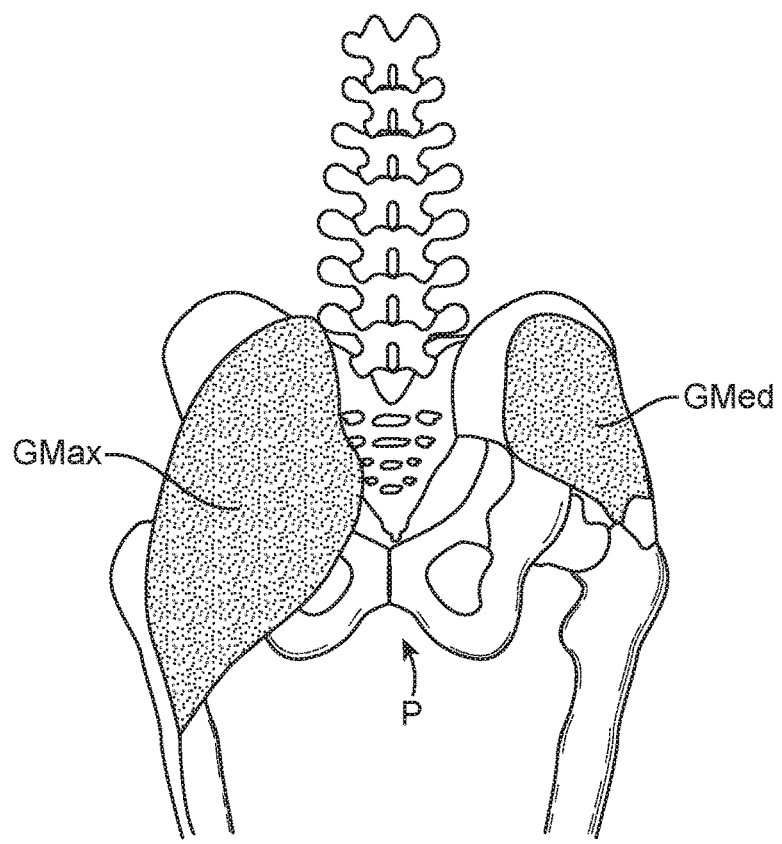
FIG. 29 is a posterior view of a hip showing gluteal muscles, and specifically the gluteus maximus and the gluteus medius.
Figure 30:
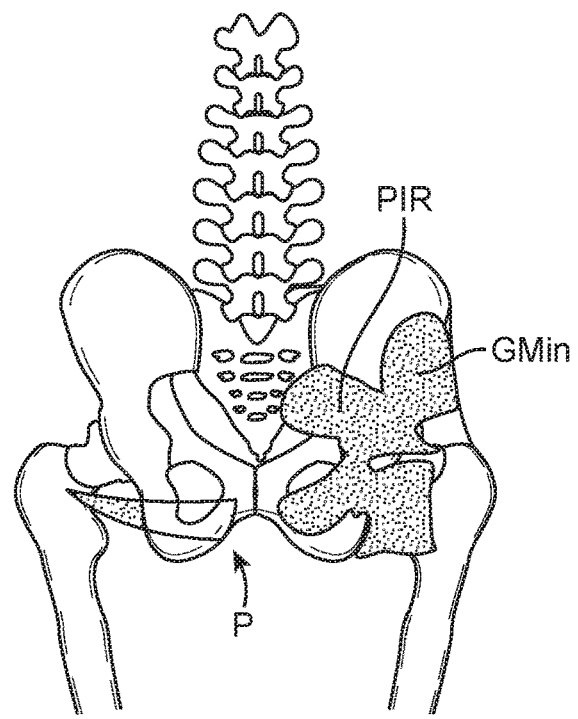
FIG. 30 is a posterior view of the hip of FIG. 29, showing lower muscles of the right hip joint.

A series of muscles extend over the ligaments L and attach between the femur F and the pelvis P. Included among these muscles are the gluteus maximus GMax (FIG. 29), the gluteus medius GMed, and the gluteus minim us GMin (FIG. 30). The gluteus maximus GMax is the uppermost of these three muscles. It is the largest of the gluteal muscles and one of the strongest muscles in the human body. Its action is to extend and outwardly rotate the hip, and extend the trunk.

The gluteus medius GMed is a broad, thick, radiating muscle, situated on the outer surface of the Pelvis P. The gluteus medius GMed starts, or originates, on the outer surface of the ilium I. The fibers of the muscle converge into a strong flattened tendon that inserts on the lateral surface of the greater trochanter G.

The gluteus minimus GMin is situated immediately beneath the gluteus medius GMed. It is fan-shaped, arising from the outer surface of the ilium I. The fibers of the muscle end in a tendon which is inserted into an impression on the anterior border of the greater trochanter G, and give an expansion to the capsule of the hip joint H.

The gluteus medius GMed is the primary muscle responsible for hip abduction, with the gluteus minimus GMin assisting. Acting synergistically with these are the psoas, piriformis PIR (FIG. 30), Tensor Fascia Latae (TFL), quadratus lumborum, and rectus femoris. The main function of the hip abductor muscles is to provide frontal-plane stability to the hip in the single-limb support phase of the gait cycle. This is achieved when the hip abductor muscles produce a frontal-plane torque that equals the frontal-plane torque produced by the body weight.

Figure 31:
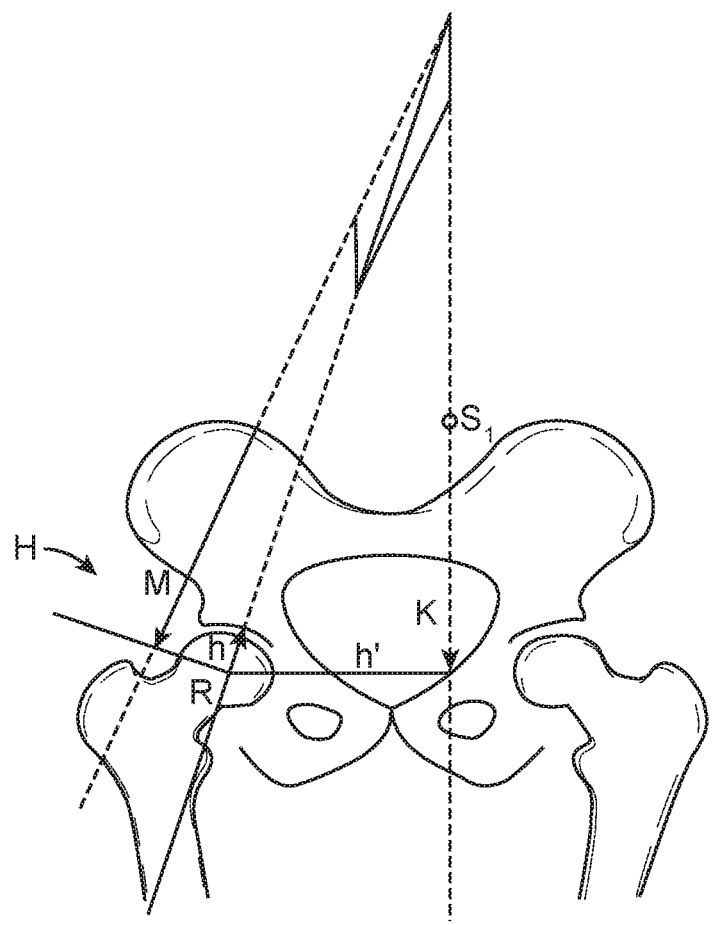
FIG. 31 is a diagram representing forces exerted on a hip joint.

Due to the difference in moment arms of the hip abductor force and body weight force, the hip abductor muscles must produce a force twice the body weight, resulting in compressive joint load of three to four times body weight during normal walking. For example, FIG. 31 is a diagram representing forces exerted on a hip joint H. S is the center of gravity, K is the mass of the body, h' is the moment arm of the body weight K, M is the force exerted by the abductor muscles, h is the moment arm of the abductor muscle force M, and R is the resultant compressive force transmitted through the hip joint (R is the resultant force of K and M). As can be seen, the h' is significantly longer than h, requiring that the hip abductor force M be substantially more than the body weight force K for stability at the hip joint H.

Figure 32C:
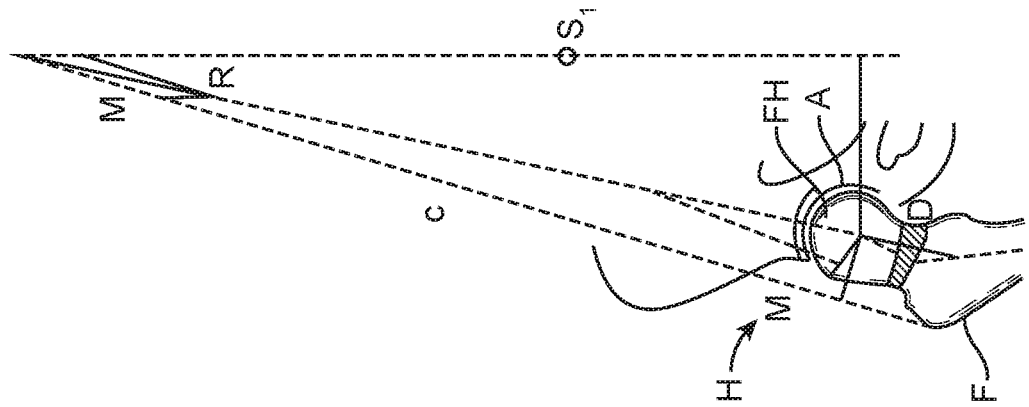
FIGS. 32A, 32B and 32C are diagrams showing the effect of femoral angle on forces exerted on a hip joint.
Figure 32B:
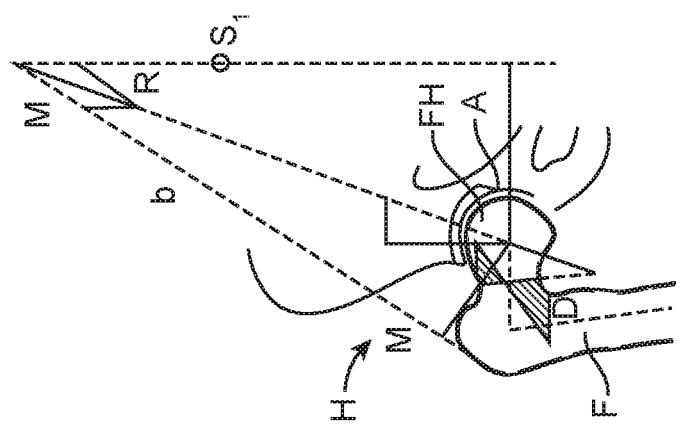
Figure 32A:
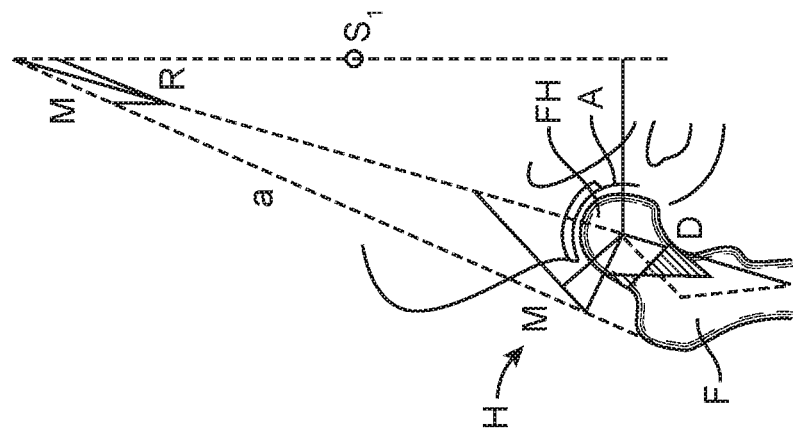

The compressive force vector R transmitted through the hip joint H is affected by the femoral neck angle since it affects the angle and the moment arm of the abductor muscle force. The angle between the longitudinal axis of the femoral neck FN and shaft S is called the caput-collum-diaphyseal angle or CCD angle. Such angle normally measures approximately 150° in a newborn and 125-126° in adults ("coxa norma"; FIG. 32A). An abnormally small angle is known as "coxa vara" (FIG. 32B) and an abnormally large angle is known as "coxa valga" (FIG. 32C).

In coxa valga (FIG. 32C), the moment arm h' of the hip abductor muscles is shorter than the normal hip, resulting in the need for a much higher hip abductor muscle force M. Additionally, the line of action of the abductor muscle force M is closer to vertical, requiring a higher force to offset the moment arm h of the body. The resultant compressive force R therefore is larger and is closer to the edge of the acetabulum A, thereby decreasing the weight bearing surface of the acetabulum. This abnormal loading of the acetabulum leads to degenerative changes along the rim of the acetabulum A, resulting in pain and eventual loss of articular cartilage.

In the case of a shallow acetabulum, the resultant force acts closer to the edge of the acetabulum A similar to a coxa valga deformity, resulting in similar degeneration of the articular surface along the rim of the acetabulum. Radiographically, an abnormal acetabulum is identified by measuring the Center-Edge angle of Wiberg, Acetabular Depth ratio, Femoral head extrusion ratio, the Lequense anterior center-edge angle etc.

In coxa vara (FIG. 32B), the line of action of the hip abductor muscles is steeper, leading to a more medial resultant force R, thereby increasing the chance of hip dislocation.

Figure 33A:
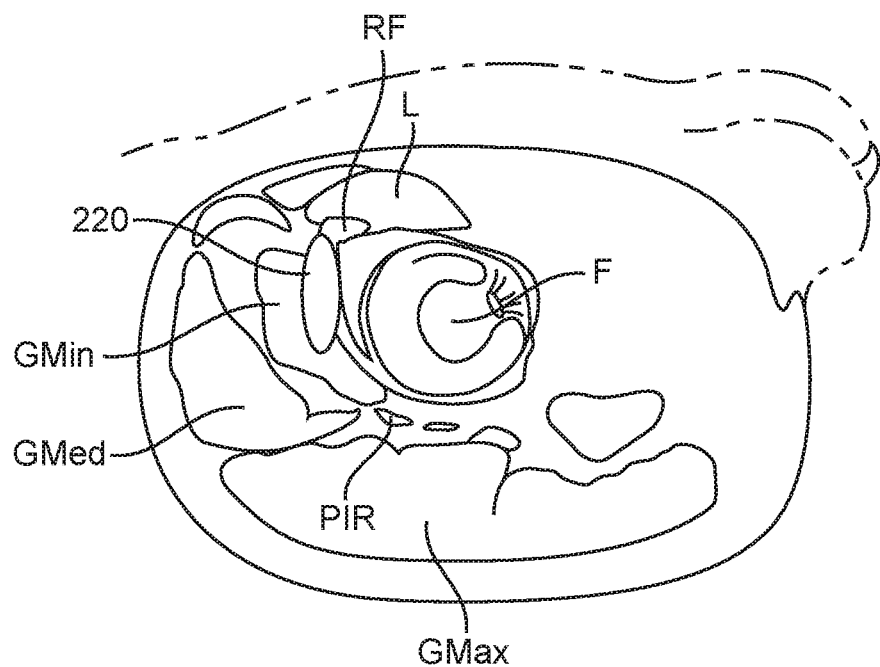
FIGS. 33A and 33B are diagrams representing a cross-section of a hip joint with a prosthesis installed therein in accordance with an exemplary embodiment of the present invention.
Figure 33B:
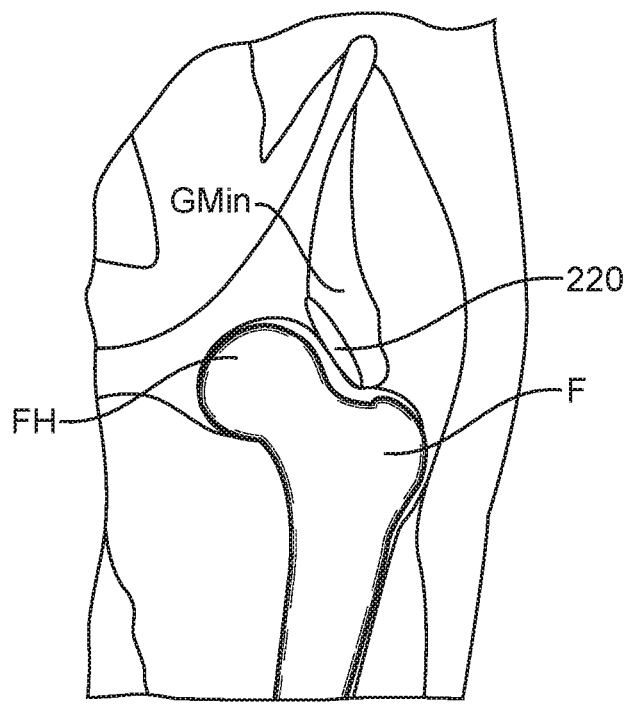

Referring now to FIGS. 33A-B, an exemplary embodiment of the present invention as applicable to correction of hip dysplasia is schematically illustrated. In the illustrated exemplary embodiment, implant 220 is installed between the gluteus minimus GMin and the rectus femoris RF. However, implant 220 may be installed in any desired location between the hip capsule and at least a portion of the hip abductor muscles so as to achieve a desired resulting force vector M. In some embodiments, implant 220 would be placed in the tissue between the gluteus muscles and the ligaments L. The implant 220 is installed in a desired location, and may be implanted arthroscopically or using a mini-open or open approach, using surgery, a balloon catheter, or another suitable procedure. As described in connection with other embodiments, implant 220 generally includes a support portion that is configured to be secured by or to surrounding tissue and a bearing portion configured to atraumatically engage and displace target tissues. A variety of alternatives for both the support and bearing portions are described herein.

The implant 220 may be formed of various materials. In some exemplary embodiments, implant 220 is constructed of a material with sufficient rigidity to displace the target tissue with a smooth outer surface to minimize friction, allowing the target tissue to slide along the implant without injury as the joint is moved. Metals such as stainless steel or titanium, or biocompatible polymers may be used. Alternatively, implant 220 may be partially or entirely constructed of a soft, compliant material and may be, for example, a compliant outer membrane filled with a fluid such as water, saline, silicon, hydro gels, gasses, and so forth. Implant 220 may be inserted in an evacuated state and filled in situ after placement, or the prosthesis could be a sealed element pre-filled with gel, fluid, polymeric or metallic beads, or other fluid or with flexible or flowable materials.

Implant 220 may also be a solid, e.g., polymeric or metallic, body of suitable atraumatic shape. A fixed shape implant 220 may alternatively include a bag with an inlet through which a curable material such as bone cement may be injected and allowed to harden. The curable material may also be polymerizable hydrogels that are cured by exposure to radiation (e.g. UV light, visible light, heat, X-rays etc.). The material may be cured by direct or transdermal exposure.

The surface of the implant 220 could be textured or smooth. A solid or compliant implant 220 may include exterior padding or a lubricious outer covering or coating to facilitate the sliding movement of the muscles and tendons along or over the prosthesis. Such padding, coating, or covering may cover a portion of, or all of the exterior of the implant 220. The padding or coatings may, for example, align to support or align a muscle or ligament. The implant may also have extensions that cover the anterior and/or posterior regions of the hip capsule, thereby reinforcing the capsule.

The implant could have a shape or feature adapted to guide the muscles and tendons and retain their position on the implant. For example, a groove or trough could be provided on the outer surface of the prosthesis through which the muscles and tendons would extend. These muscles and/or tendons are aligned with the groove when the implant is installed. Alternatively, the implant could include a ring or eyelet with a discontinuity to allow placement of the ring or eyelet around the muscles/tendons.

Figure 34A:
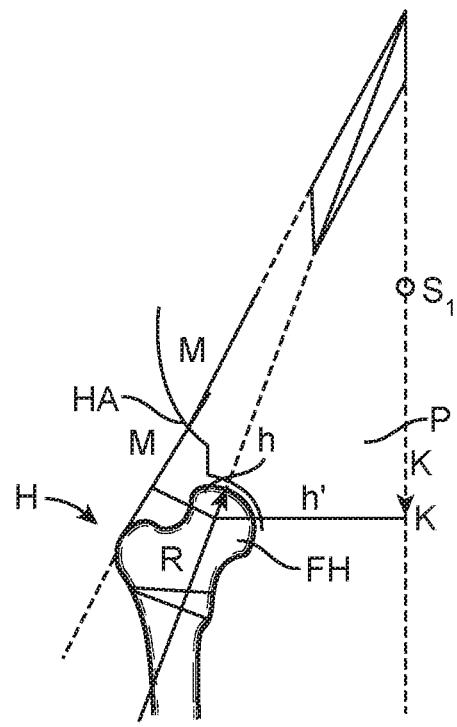
FIGS. 34A and 34B are force diagrams showing the effect of the prosthesis of FIGS. 33A-B on the hip abductor force in accordance with an exemplary embodiment of the present invention.
Figure 34B:
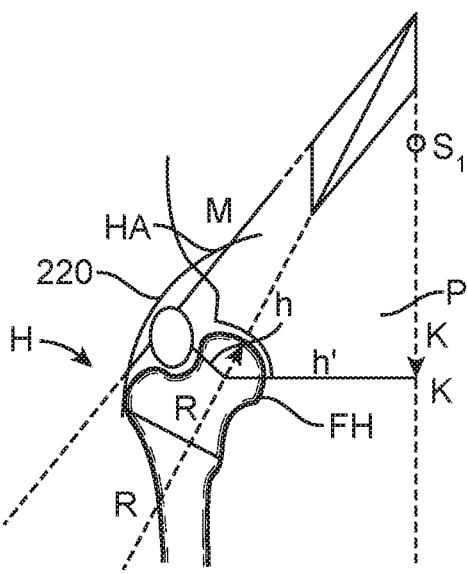

FIGS. 34A and 34B show effects of the implant 220 on the hip abductor force M in accordance with an embodiment. As can be seen in FIG. 34A, the hip abductor muscles HA, prior to installation of the implant 220, extend in a first direction. A force concentration M toward the lateral edge of acetabulum A may be seen. After installation of the implant 220, as shown in FIG. 34B, the hip abductor muscles HA are displaced outwardly away from the joint, increasing the angle and the length of the moment arm h of the force exerted by the abductor muscles relative to the central axis of the joint. As a result, the resultant force R through the femoral head to counteract the body weight force moves more centrally into the joint and away from the lateral edge of the acetabulum A. As such, the resulting force vector R may be more properly aligned to press the femoral head FH into full contact with the acetabulum A, or to otherwise provide a more desirable force arrangement for the hip.

As with other embodiments of the present invention, prostheses for treatment of hip disorders according to the present invention may include suitable anchors for affixing implants in place, and/or may be stabilized by the surrounding muscle and/or ligament structures. In an embodiment, the prosthesis extends from the pelvis P to the femur F, and may be anchored at one or both of these sides, or may not be anchored at all. Shape, materials or surface texture may be incorporated into the support portion to facilitate and maintain placement by surrounding tissue. Tabs or other features may be provided for an implant to aid in anchoring or positioning the implant in a desired manner with respect to the pelvis P and/or the femur F. Either the femur side or the pelvis side of an implant may include one or more such tabs to attach and/or to arrange the implant in a desired manner. The implant may be a standard shape, or may be custom made for a particular application, either through planning process as described below or inter-operatively.

Figure 35:
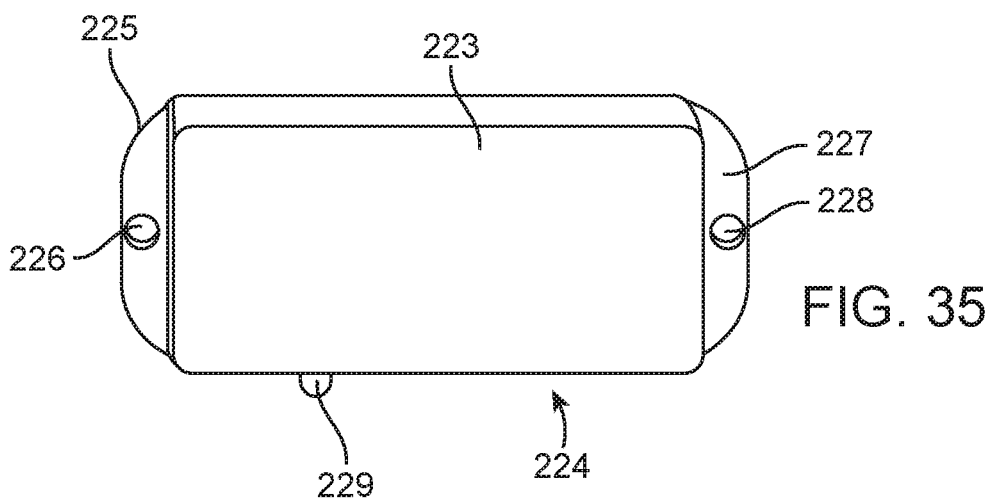
FIG. 35 shows a prosthesis that anchors to the femur and the pelvis in accordance with an exemplary embodiment of the present invention.

As an example, FIG. 35 shows a prosthesis 224 that anchors to the femur F and the pelvis P. The prosthesis 224 includes a main body 223 forming a bearing member and a support member including fixation tabs. First tab 225 has an opening 226 to anchor prosthesis 224 to the greater trochanter and second tab 227, on the opposite end, has an opening 228 to anchor to the pelvis. The body 223 may have various shapes including rectangular prism, sphere, egg-shape, cylinder, conical, trapezoidal, or others as appropriate to achieve the desired realignment of forces in the joint. The prosthesis 224 may be used to shift the force vector M for the hip abductor muscles of a hip joint as described above.

A suture anchor, bone tack, bone screw or other suitable attachment structure may be utilized to attach the trochanter side of the prosthesis 224 utilizing the opening 226. In a similar manner, the opening 228 may be utilized to anchor the prosthesis in the pelvis. The anchoring device may be placed percutaneously after the implant has been positioned.

As described above, embodiments of prostheses may be installed and filled with a fluid in situ. To this end, an access port 229 may be provided for filling the prosthesis 224 either during surgery or may be installed so that it is accessible after surgery.

Figure 36:
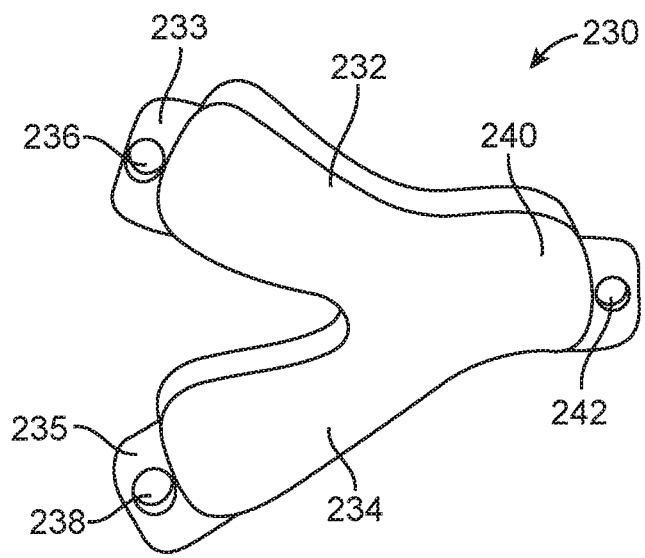
FIG. 36 shows a prosthesis including two tabs for a femur side of the prosthesis in accordance with an exemplary embodiment of the present invention.

As another example, as shown in FIG. 36, a prosthesis 230 includes a body having a wishbone shape, with a main stem 240 and two legs 232, 234 for a femur side of the prosthesis forming at least part of a bearing member. Each of the legs 232, 234 includes a tab 233, 235 extending therefrom, each with an anchor opening 236, 238. The fixation tabs form at least a part of a support member. The main stem 240 is provided for the pelvis side of the prosthesis, and includes an anchor opening 242.

The two tabs 233, 235 may, for example, be anchored on opposite sides of the greater trocanter G. As other alternatives, a femur side of a prosthesis may be fixed or otherwise anchored to the femoral neck F, or at a location on the femur F below the greater trochanter G. The main stem 240 may be fixed to the ilium I, the ischium IS, or another suitable location on the pelvis P, either on the posterior or anterior aspect. As an alternative to the arrangement in FIG. 36, two tabs may be provided on the pelvis side of the prosthesis 230. These two tabs may be anchored, for example, one on the posterior and one on the anterior side of the pelvis.

Figure 37:
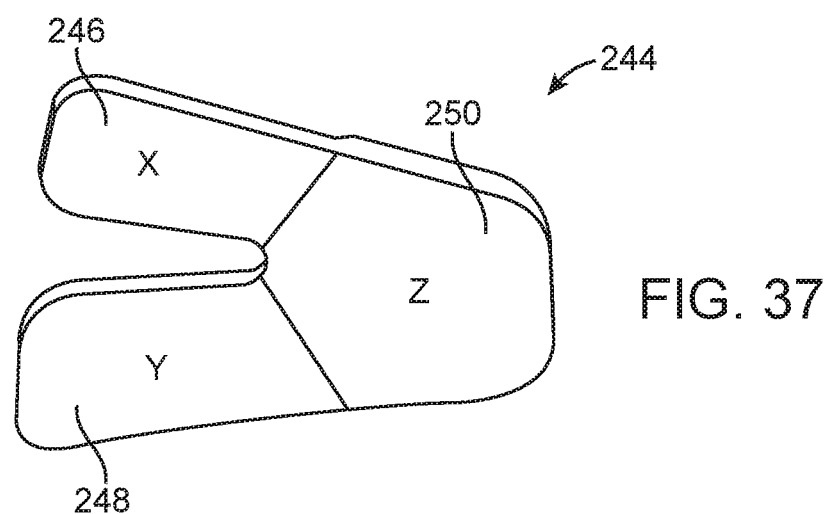
FIG. 37 shows an exemplary prosthesis, similar to the prosthesis in FIG. 36, but not having anchor structures.

FIG. 37 shows another embodiment of a prosthesis 244. Like the prosthesis 230, prosthesis 244 includes two legs 246, 248 on the femur side of the prosthesis, and a main stem 250 that aligns with a pelvis side of the hip joint when the prosthesis is installed. However, unlike the prosthesis 230, the prosthesis 244 does not include structures, such as tabs and/or anchoring holes, for anchoring of the prosthesis to the femur. As described above, such a prosthesis 244 may be fixed in place by the surrounding muscle structures, which are layered tightly around the hip capsule. Similarly, the main stem 250 does not include a tab and/or an anchor for attachment to the pelvis.

If desired, as an alternative, a prosthesis may be anchored only on a femur side or a pelvis side and/or may include legs on either side which may be anchored or held in place by muscle structure. As an example, a single anchor, such as a tab and/or an opening, may be provided on either or both of the legs 246 or 248, and/or an anchor may be provided on the main stem 250. Any combination of anchors or muscle stabilized support may be used. In such embodiments the bearing and support members may be integrated.

In accordance with another exemplary embodiment, a prosthesis may have varying thickness so as to provide varying displacement of the abductor muscles and/or hip tissues. As an example, as shown in FIG. 37, the prosthesis 244 includes three areas having different thicknesses, X, Y and Z. The thickness X corresponds with the leg 246, the thickness Y corresponds with the leg 248, and the thickness Z corresponds with the main stem 250. Varied thickness may also be used along a leg or stem, or across the leg or stem. These areas of varied thickness X, Y and Z may be utilized to advantageously fit the prosthesis 244 in the hip joint H, and/or to provide a desired force offset. Prosthesis 244 may be pre-shaped to have the varied thickness prior to implantation, or each portion of the prosthesis may be separately enlarged to the desired thickness in situ by, e.g., filling with a desired volume of inflation medium to achieve the desired thickness.

Figure 38:
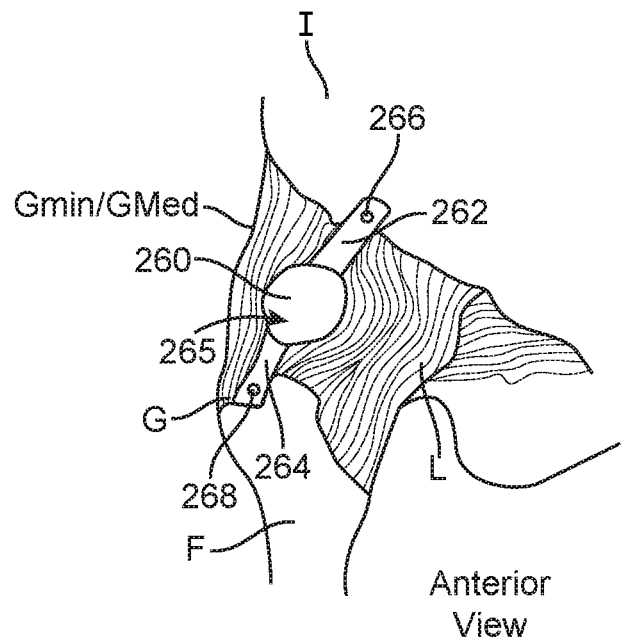
FIG. 38 shows an anterior view example of a prosthesis installed in a hip joint in accordance with another exemplary embodiment of the present invention.
Figure 39:
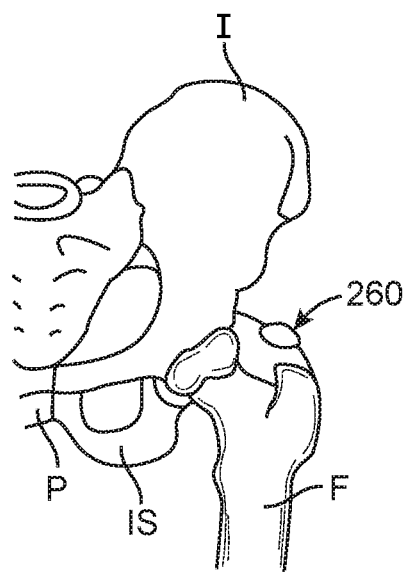
FIG. 39 is a representation of the prosthesis of FIG. 38, with the ligaments and the abductor muscles removed.

FIG. 38 shows an anterior view example of a prosthesis 260 installed in a hip joint H in accordance with an embodiment. FIG. 39 is a representation of the prosthesis 260 in place, with the ligaments L and the abductor muscles removed to show detail. In the embodiment shown in FIG. 38, prosthesis 260 includes a pelvic tab 262 and a femur tab 264, forming at least part of a support member and both extending from a central, rounded, bulbous main section 265 forming a bearing member. The bulbous configuration of the main section 265 aids in a desired displacement of the abductor muscles. Pelvic tab 262 and femur tab 264 may be a thin and highly flexible material to minimize any impact on joint articulation. The pelvic tab 262 is anchored to the pelvis, for example via a pin 266, bone screw, suture, or other suitable anchor fixed to the ilium 1. An opening may be provided in the tab for the anchoring function. The femur tab 264 is anchored by a suitable anchor, for example a pin 268, to the greater trochanter G, femoral neck, or other suitable location. The main section 265 in the embodiment shown in FIG. 38 is centrally mounted, and is arranged so that, when the prosthesis 260 is installed, the main section 265 is positioned between the capsular ligaments L and muscle structure of the gluteus minimus GMin and gluteus medius GMed. However, the main section 265 may be positioned closer to either the pelvis attachment or the femoral attachment, and may be arranged at other locations so as to desirably alter the force vector M.

Figure 40:
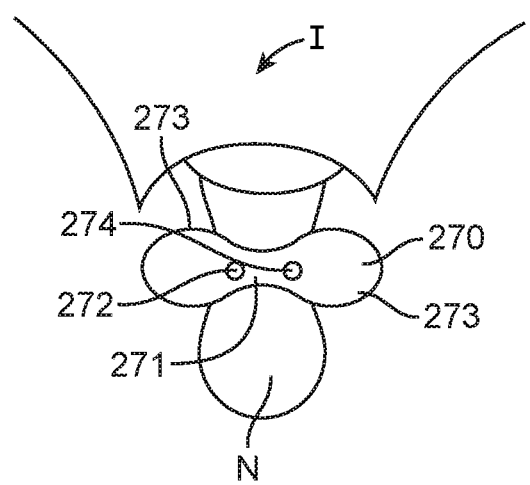
FIG. 40 shows a dog bone-shaped prosthesis extending transverse to a femoral neck in accordance with a further exemplary embodiment.
Figure 41:
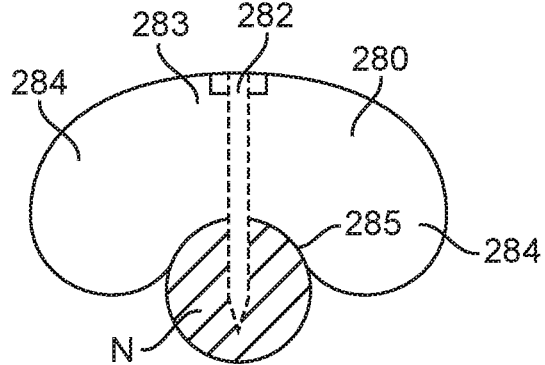
FIG. 41 shows a kidney-shaped prosthesis that extends transverse to a femoral neck in accordance with an embodiment.
Figure 42:
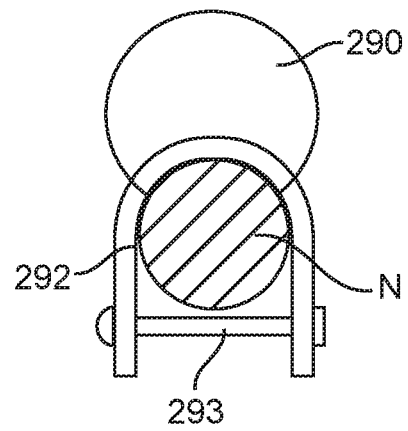
FIG. 42 shows a prosthesis mounted on a U-shaped bracket that extends around a femoral neck in accordance with an exemplary embodiment of the present invention.

In accordance with additional embodiments, illustrated in FIGS. 40-42, an implant may be attached only to the femoral neck N, by a support member and/or may extend transverse to the femoral neck. In this manner, the prosthesis may provide a bearing member for displacement of a larger amount of muscle and/or tissue around the girth of the femoral neck N and/or may be more easily maintained in place due to direct attachment around at least a portion of the femoral neck N. Such a prosthesis may be dog bone or kidney shaped so as to nest around the capsule ligaments L or femoral neck N on one side. Typically, a dog bone shape includes a narrowed, usually elongate, central section, and a bulbous, or rounded, larger diameter shaped at each end. A kidney shape, on the other hand, is more bean shaped, with two outer ends extending in one direction so that a groove or indentation is formed on a side of the shape. For either shape, a groove or other shape may be provided on the other side through which the tendons and muscles may slide without slipping off the prosthesis. Deformable pillow-like structures filled with gel, foam, or beads may also be used to conform to or partially wrap around the capsule ligaments L or femoral neck N.

As an example, as shown in FIG. 40, dog bone shaped prosthesis 270 extends transverse to and nests around a femoral neck N and/or the ligaments L. The dog bone shaped prosthesis 270 in FIG. 40 includes a narrow central section 271 between two outer, bulbous, rounded ends 273. The narrow section is of sufficient length so that the two ends nest on opposite sides of the ligaments L or femoral neck N.

In the embodiment shown in FIG. 40, the prosthesis is attached by two anchors, such as pins or screws 272, 274, through the central section 271 into the femoral neck N. However, as described in previous embodiments, a prosthesis may be installed without fasteners, or the prosthesis may be anchored in another way or location. An upper part of the prosthesis 270 may channel muscles through the upper saddle formed between the two ends 273 and along the central section 271 of the dog bone shaped prosthesis 270.

FIG. 41 shows another embodiment of a prosthesis 280 that extends transverse to a femoral neck. The prosthesis 280 is kidney-shaped, and includes a narrower central section 283 and two outer, rounded ends 284. An indentation 285 is formed between the ends. In an embodiment, the prosthesis is shaped so that the indentation matches the curvature of the femoral neck and/or ligaments L onto which the prosthesis attaches, and thus the prosthesis nests at least partly around the femoral neck N when installed. In the embodiment shown in the drawings, an optional pin or screw 282 is used for anchoring the prosthesis 280 to the femoral neck N, but other anchors, or no anchor at all, may be used.

As another alternative, a prosthesis may be anchored to the femoral neck utilizing a U-shaped or C-shaped bracket or band or other structure that extends around the femoral neck. As an example, FIG. 42 shows a prosthesis 290 mounted on a U-shaped bracket 292 that extends around a femoral neck N and/or ligaments L. The U-shaped bracket 292 is curved to fit closely around the femoral neck N and includes a bolt 293 that extends through openings (not shown) on ends of the bracket and along an opposite side of the femoral neck. The bolt 293 may be used to lock the U-shaped bracket 292 in place. The prosthesis 290 in FIG. 42 is bulbous-shaped, but the U-shaped bracket 292 may alternatively be used with other shapes of prostheses, such as the dog bone shaped prosthesis 270, or the kidney-shaped prosthesis 280.

Figure 43:
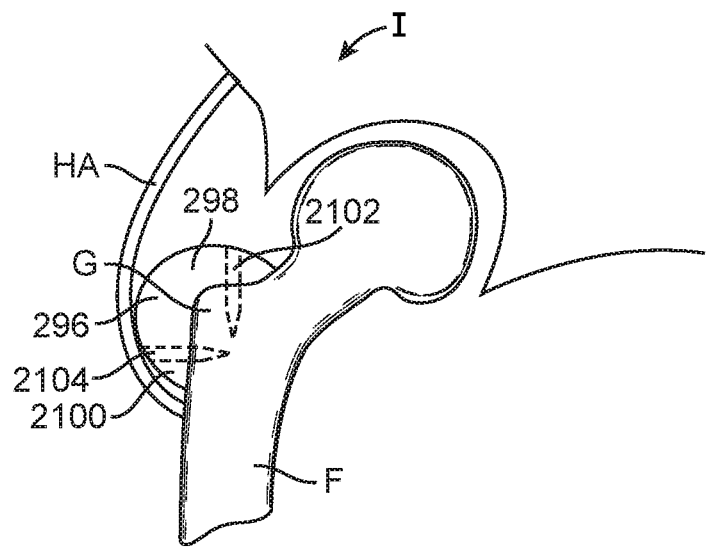
FIG. 43 shows a prosthesis mounted as a cap on the greater trochanter in accordance with another exemplary embodiment of the present invention.

In accordance with further embodiments, a prosthesis may be mounted as a cap on the greater trochanter G for displacing hip abductor muscles. As an example, FIG. 43 shows a prosthesis 296 mounted as a cap on the greater trochanter G. The prosthesis 296 includes a horizontal extension 298 and a vertical extension 2100 that form an L-shape that extends upside down against the greater trochanter G. In the embodiment shown in FIG. 43, the prosthesis 296 is anchored by pins 2102, 2104, but may be anchored or attached in another manner, including a U-shaped or C-shaped bracket or band or other structure that extends around the femoral neck, as described above. As can be seen in FIG. 43, the prosthesis 296 is rounded on an outer side, and projects laterally from the hip so as to substantially displace the hip abductor muscles HA. In this exemplary embodiment, the bearing and support members are combined in a manner similar to implant 40 as described above.

Figure 44:
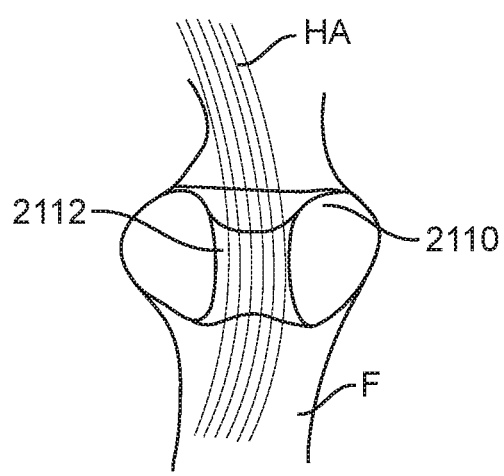
FIG. 44 shows a prosthesis including a groove or channel for receiving the hip abductor muscles in accordance with an exemplary embodiment of the present invention.

To aid the hip abductor muscles HA and/or tendons or other tissue sliding over the prosthesis 296 or another cap prosthesis, the outer surface of the cap may be lubricious. Alternatively, a guide or other structure may be provided for maintaining tendons and muscles in place, and for providing a sliding feature. As an example, as shown in FIG. 44, a prosthesis 2110, which may be shaped like the prosthesis 296, includes a groove or channel 2112 for slidably receiving and guiding the hip abductor muscles HA as prosthesis 2110 moves with the femur. Other structures, such as rings, eyelets, tunnels, or other features may be used to guide and position the hip abductor muscles HA and/or ligaments and tendons.

Figure 45:
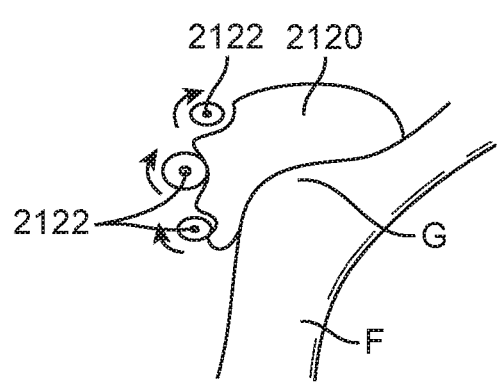
FIG. 45 shows a prosthesis including external rollers for permitting hip abductor muscles to roll over the prosthesis as the femur moves in accordance with an exemplary embodiment of the present invention.
Figure 46:
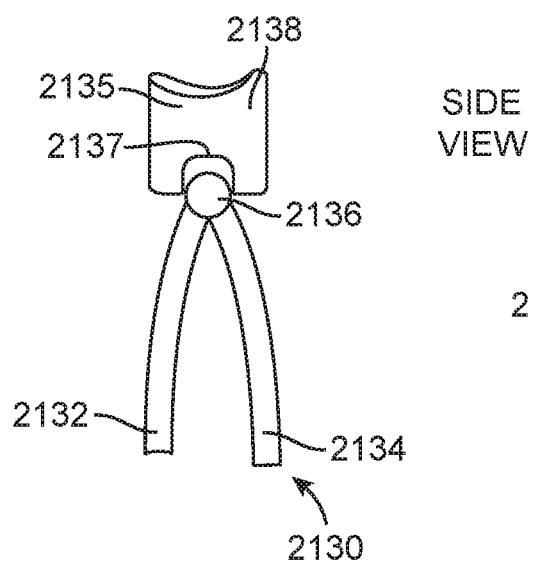
FIGS. 46, 47, 48 and 49 show another example of a prosthesis which includes two legs connected by a hinge.
Figure 47:
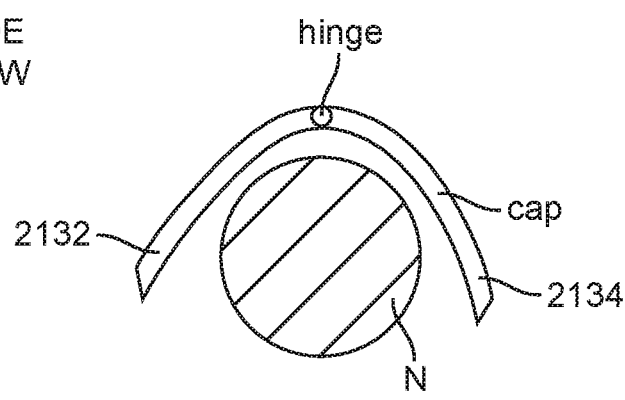

As another example, a prosthesis, such as the prosthesis 2120 shown in FIG. 45 may include one or more external rollers 2122 for permitting the hip abductor muscles HA to roll over the prosthesis 2120 as the femur F moves. The prosthesis 2120 includes a series of three rollers 2122 rotationally mounted to the lateral and/or superior surface of prosthesis 2120 so as to align with the hip abductor muscles HA and their primary direction of movement.

In accordance with another embodiment, a prosthesis may be configured to expand in situ so that the prosthesis may be inserted into a body in a contracted state via a cannula or mini-open procedure, expanded in situ, and installed in the expanded state. As an example, a device may include one or more hinges or may be flexible so that it may contract to a small space, and expand when installed. A spring or other device may be used for expanding the prosthesis, or the device may be expanded mechanically or in another manner. An example is shown in FIGS. 46-49, where a prosthesis 2130 includes two legs 2132, 2134 connected by a hinge 2136. The two legs 2132, 2134 form a cap that may be fitted as a support member, for example, on the greater trochanter G or on the femoral neck N.

Delivery device 2138 may be provided that captures the hinge 2136 and keeps the legs 2132, 2134 together during insertion, and opens the legs during installation. The delivery device 2138 includes a tubular shaft 2135 configured for receiving the hinge 2136 and legs 2132, 2134 within the shaft during delivery. The walls of the delivery device 2138 capture the legs 2132, 2134 and keep the legs closed during insertion. Prosthesis 2130 is held in the shaft by means of friction with the inner wall thereof, or, optionally, an inner shaft (not shown) may be slidably positioned in shaft 2135 which has a distal coupling mechanism adapted to releasably grasp hinge 2136.

Once the prosthesis 2130 is inserted by the delivery device 2138, retraction of the delivery device may cause the prosthesis to expand, or the prosthesis may be expanded mechanically or in another manner. As an example, an inner shaft (not shown) may be releasably coupled to the prosthesis 2130, the actuation of which causes the legs 2132, 2134 to open and the prosthesis to release from the delivery device. The legs 2132, 2134 may be separated during installation to fit around, for example, the femoral neck N (FIG. 47) and/or the ligaments L, or the greater trochanter G. In an installation embodiment, for example, the prosthesis 2130 may be expanded around the femoral neck N (FIG. 48) and may be moved over and then installed on the greater trochanter G.

Use of the prosthesis 2130 provides minimally invasive surgery, due to the ability to install the prosthesis while closed. Thus, a small incision may be used, and/or the prosthesis may be installed through a cannula. The device, once installed, may be anchored in place via pins or other suitable fasteners, or may be held in place by the muscle or tissue structure around the femur F.

Figures 48, 49:
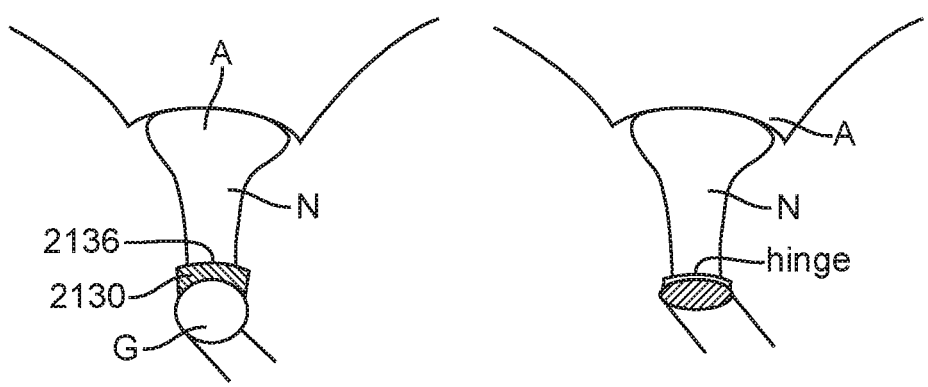

Prosthesis 2130 may be configured to expand outward to form a cap to fit over the greater trochanter G as shown in FIG. 48 or to fit in a suitable manner around a portion of the femoral neck N as shown in FIG. 49. As another embodiment, a prosthesis may include two or more elements, such as hinged or folding elements, that connect together to form a contiguous implant. As an example, two or more hinged or folded elements could be introduced into a space and then locked together to form a contiguous implant. Locking multiple elements together can be achieved through alignment of features, the elements may be snap locked together, or the elements may be connected by fasteners, crimping, or another suitable manner. As an alternative, multiple elements might nest together when put into place and may be attached adjacent to one another via suitable fasteners such as bone screws, tacks, pins or other fasteners. In an embodiment, each element or part is expanded in situ.

Figure 50:
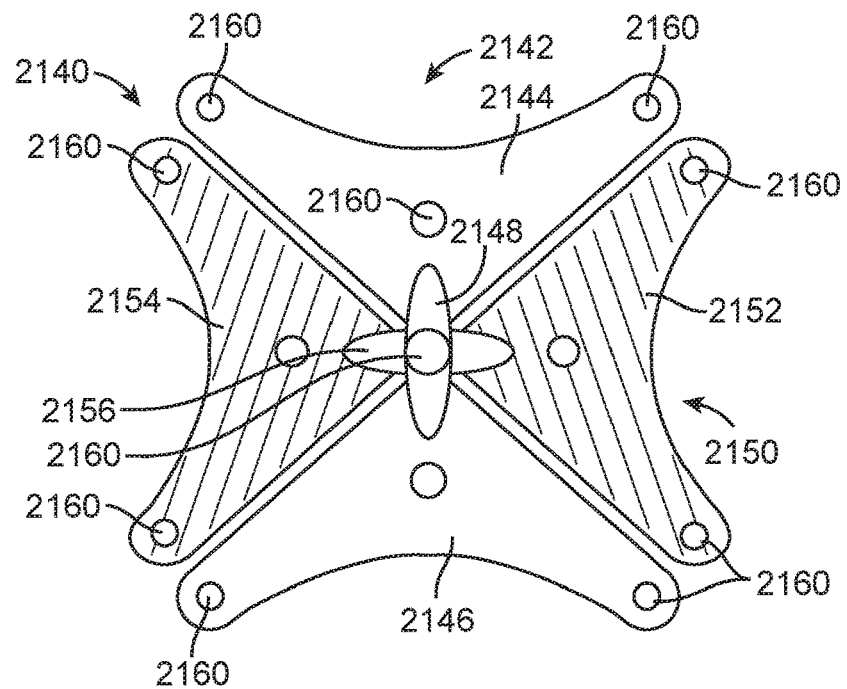
FIG. 50 shows a prosthesis having two hinged elements, each having first and second crescent moon-shaped legs connected by a hinge, with the two hinged elements nested together in accordance with a further exemplary embodiment of the present invention.
Figure 51:
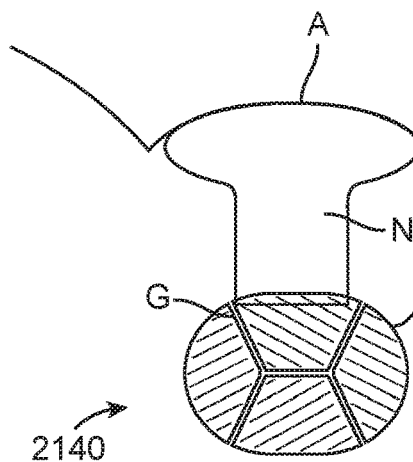
FIG. 51 shows the prosthesis of FIG. 50 installed on a greater trochanter.

An example of such prosthesis 2140 is shown in FIG. 50, where a first hinged element 2142 is butterfly-shaped, with first and second crescent-shaped, wishbone-shaped, or triangular legs 2144, 2146 connected by a hinge 2148. The two crescent-shaped legs 2144, 2146 are arranged so that the concave portion of each of the legs faces outward and directly opposite each other. A second hinged element 2150 also includes two similar crescent-shaped legs 2152, 2154 attached by a hinge 2156. The two hinged elements 2142, 2150 may be attached to each other prior to implantation, or may be introduced separately and attached in situ. The two hinged elements 2142, 2150 may be installed by, for example, first installing the first hinged element 2142, and then installing hinged element 2150 on top of and nested around the first hinged element 2142. In each case, the hinged elements are folded before and during installation, and expanded in situ. The hinged elements 2142, 2150 may be anchored in a suitable manner, for example at anchor locations 2160 to a position throughout the prosthesis 2140. One such anchor position may be at the overlap of the two hinges 2148, 2156. As shown in FIG. 51, the prosthesis 2140 may be mounted, for example, on the greater trochanter G or in another suitable location.

In accordance with another embodiment, a belt, strap, or other tension mechanism may be extended around and tightened on the femoral neck N and the hip abductor muscles HA and/or the hip capsule ligaments/tendons. The band or strap or other structure may be tightened to increase tension, thereby increasing the force pulling on the femur F. This approach might be used, for example, where the increased tension produces a resultant force suited for the particular pathology of the patient. For example, for patients with excessive loading on the medial side of the joint, the belt may be used to increase tension on the lateral side of the joint producing a higher lateral force component and reducing loads on the medial side of the joint. In such an embodiment, the belt or strap would extend around the femoral neck and the hip abductor muscles and/or capsule ligaments/tendons on the lateral side of the joint, but would extend under the hip abductor muscles/tendons on the medial side of the joint. For patients with excessive loading on the lateral side of the joint, the arrangement of the belt or strap may be reversed.

As with previous embodiments, the belt or strap could have a lubricious interior surface to allow sliding movement of the muscles relative to the belt or strap. The belt or strap may optionally extend only part of the way around the femoral neck and may be a rigid partial ring or hoop. The belt or strap may optionally be fixed to the femoral neck by one or more anchors, such as a pin or screw. The belt or strap may be flexible, or it may be a rigid ring or hoop, composed of fabric, metal or a polymer. A rigid structure may be circular, oval, racetrack, or another suitable shape, and may have a discontinuity to allow insertion around the muscles and the femoral neck N. The belt or strap may be elastic to act like a spring, or may be non-distensible.

Figure 52:
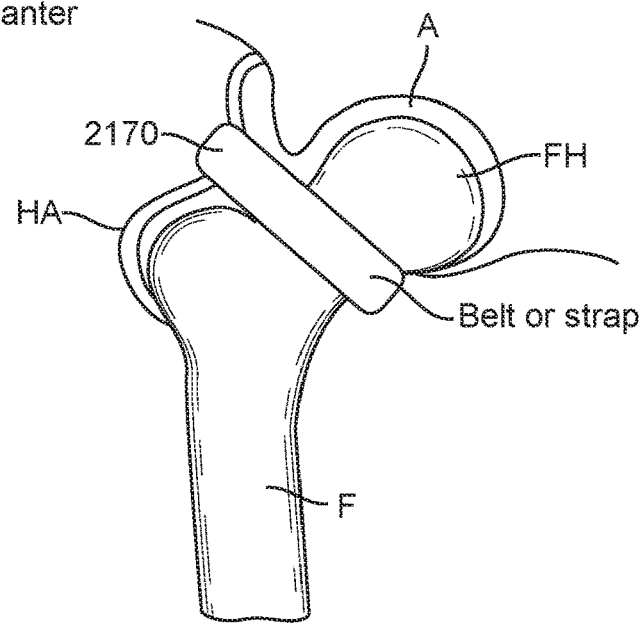
FIG. 52 shows a strap extending around the femoral neck and the hip abductor muscles in accordance with an exemplary embodiment of the present invention.

An example of such a belt or strap is shown in FIG. 52, where a strap 2170 extends around the femoral neck N and the hip abductor muscles HA. The belt or strap may take many forms, and may be arranged as needed for a desired force effect. In such embodiments the bearing member is formed to act inwardly and the support member is opposite and surrounds the bone or other tissue at the fixation location.

If desired, the belt or strap, such as the belt or strap 2170, may include an adjustment mechanism to allow cinching of the belt or strap to increase tension in the muscles and/or ligaments. Examples of cinching mechanisms that may be used are shown in FIGS. 53-56. In FIG. 53, a one-way clamp is provided that allows a physician to install the tension strap and pull on a free end 2182 to cinch the strap 2180 around the femoral neck N and the hip abductor muscles HA. The device in FIG. 53 includes a catch strap 2183 and a pawl 2184. The strap 2180 includes a number of openings 2186 along its length. An installer pulls on the free end 2182 of the strap, pulling up to keep the openings from catching on the pawl 2184. The catch strap 2183 maintains alignment of the free end 2182 when pulled. When the strap 2180 is tight, the installer pulls down on the free end 2182 and aligns the pawl 2184 with a desired opening 2186 on the strap. The catch strap 2183 and the pawl 2184 hold the free end 2182 in position.

Another example of one-way clamp 2190 is shown in FIG. 54, in which pawl 2192 engages teeth 2194 on a strap 2196. The teeth 2194 include a sloped front side and a blunt rear side. The pawl 2192 engages the blunt rear side to prevent retraction of the teeth 2194. The sloped front sides permit indexing of the teeth in one direction past the pawl 2192 when a physician pulls on the free end of the strap 2196.

Another example of a cinching mechanism is shown in FIG. 55, where a device 2200 is configured like a hose clamp and includes a screw 2202 that engages openings 2204 in a strap 2206. Rotation of the screw 2202 causes the strap to tighten or loosen depending on the rotation direction.

FIG. 56 shows an example of another device 2210 that may be used as a cinching mechanism. The device 2210 includes two rigid C-shaped members 2212, 2214 connected at one edge by a hinge 2216 and at another edge by screw 2218. The device 2210 may be tightened or loosened by rotation of the screw 2218.

Figure 57:
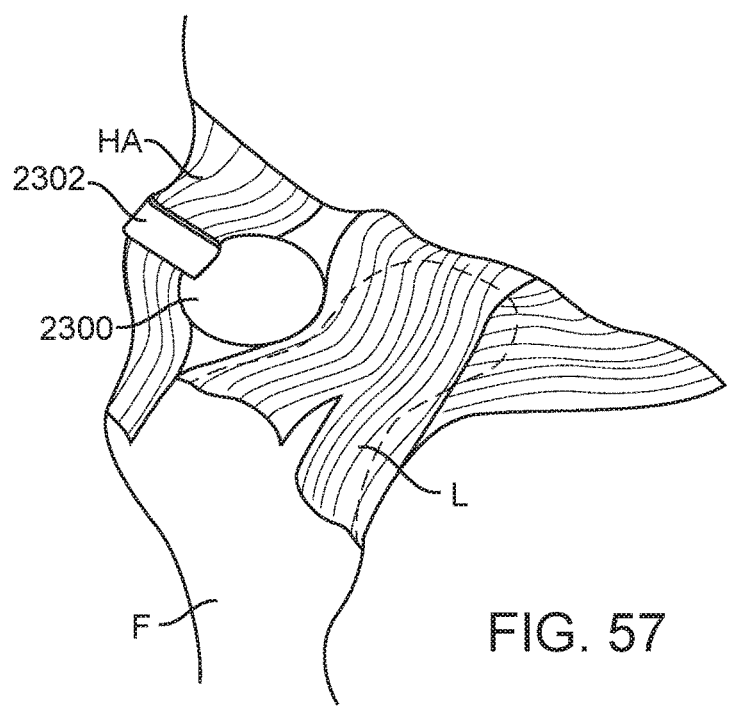
FIG. 57 shows an alternative attachment of a prosthesis in which the prosthesis is connected to hip abductor muscles via a band.

FIG. 57 shows a prosthesis 2300, similar to the prosthesis 220, in which the prosthesis is connected to hip abductor muscles HA via a band 2302. The band 2302 anchors the prosthesis 2300 in place. The band 2302 may be tied or clasped into place. In an embodiment, the band uses a cinching mechanism, such as any of the cinching mechanisms described above, to cinch the band 2302 into place around the hip abductor muscles HA. Alternatively, a prosthesis, such as the prosthesis 2300, may be installed in position, and a band or belt may extend around the muscles or capsular ligaments to maintain the position of the prosthesis without the belt being attached to the prosthesis. In this manner, the band or belt aids in capturing the prosthesis in place.

Figure 58:
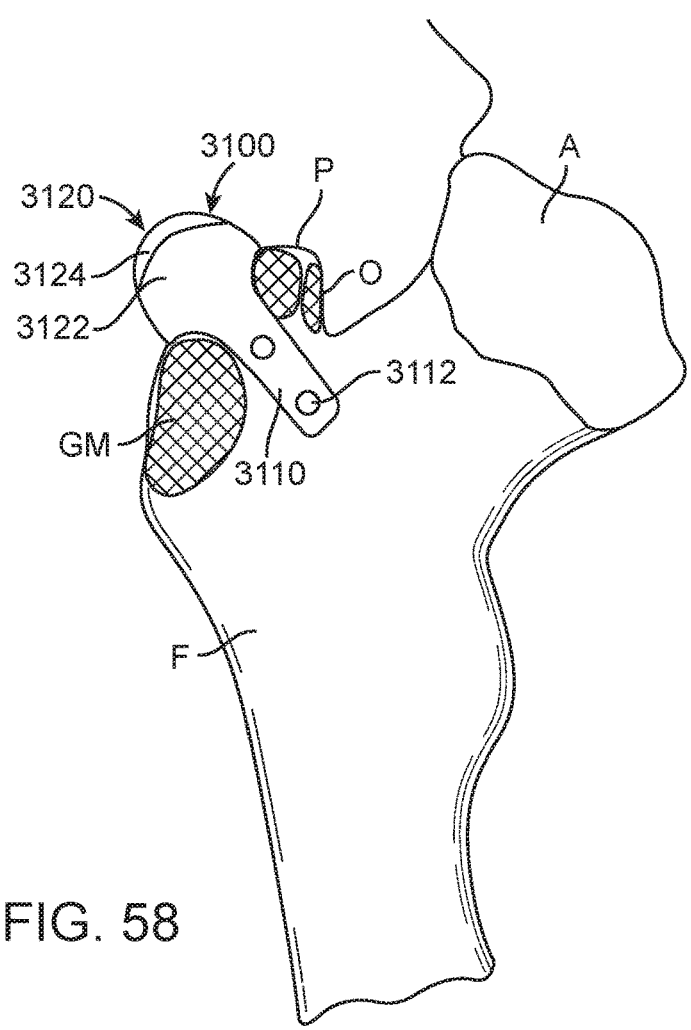
FIG. 58 is an anterior view of a human hip with an alternative implant mounted according to an alternative embodiment of the present invention.
Figure 59:
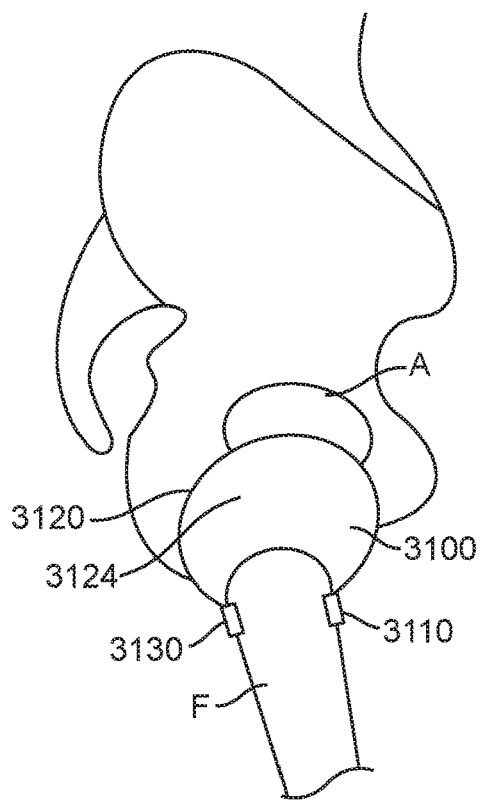
FIG. 59 is a lateral view of the embodiment shown in FIG. 58.
Figure 60:
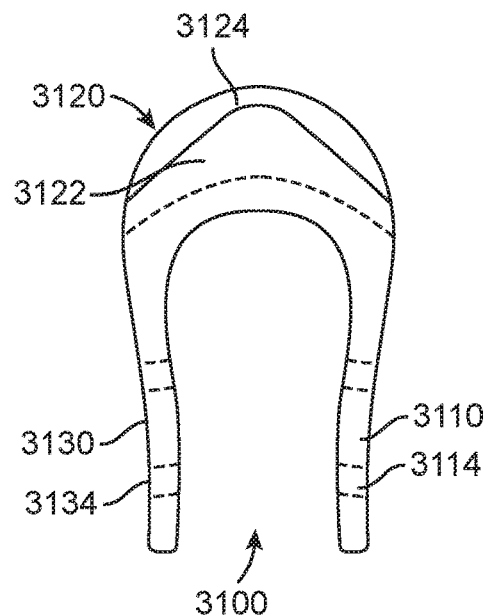
FIG. 60 is a side view of the implant shown in FIGS. 58 and 59.

In another embodiment of the present invention, illustrated for example in FIGS. 58-60, an implant 3100 for treatment of hip disorders is shaped to jog around the insertion point(s) of connective tissues (including target tissues) around the joint. Depending on specific joint anatomy and patient conditions, the implant may be designed to permit secure fixation at a suitable site while still placing the bearing and displacement portion under the target tissue while minimizing trauma to important intervening tissues. For example, as shown in FIGS. 58 and 60, implant 3100 may include three sections—anterior section 3110, superior section 3120 and posterior section 3130. Sections 3110 and 3130 are support members providing the fixation sections and may include means such as screw holes 3114, 3134 to accommodate bone screws 3112 (as shown in FIG. 58) for securing to the bone. Section 3120 comprises bearing member 3122 with a bearing surface 3124 as described herein above.

Implant 3100 may be of unitary construction or may include two or more interlocking units assembled together. The different sections could be made for identical materials or different materials, for example the bearing section 3120 may be fabricated out of pyrolytic carbon and the fixation sections from titanium or other similar bone compatible material.

In order to address the specific anatomy, anterior section 3110 may be shaped to attach to the femur by circumventing muscle attachment sites such as for the Gluteus minimus (GM), Piriformis (P), and Obturator internus and superior and inferior gemelus (O). Other sites to be avoided include the vastus lateralis medially, and the vastus intermedius and medialis superiorly. Posterior section 3130 may be shaped to attach to the femur between the attachment sites of the quadratus femoris and the iliopsoas muscles. In the sagittal plane, sections 3110 and 3130 also may be shaped as needed to avoid any muscles (non-target tissue) that are traversing medial to lateral.

In a further alternative embodiment, instead of installing a device, a fluid may be injected into the desired space within or adjacent to the hip abductor muscles that hardens to a solid, allowing the fluid to harden into a solid, the solid then providing the function of the prosthesis. As examples, the prosthesis may be injected as a liquified polymer or foam material into the space between the gluteus muscles and femoral neck and allowed to harden. The material could have adhesive properties to stick to the capsular ligaments around the femoral neck. A balloon or other expandable member or retractor could be inserted to create space between the femoral neck and the gluteus muscles into which the material is injected.

Figure 61A:
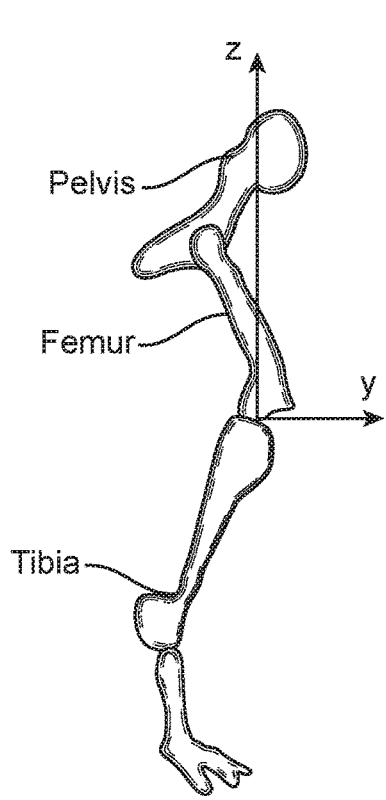
FIGS. 61A and 61B are lateral and anterior views, respectively, of a canine right hind limb and hip.
Figure 61B:
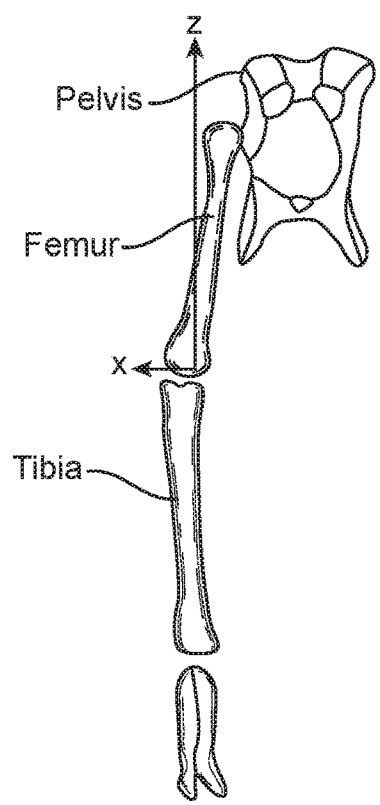
Figure 62:
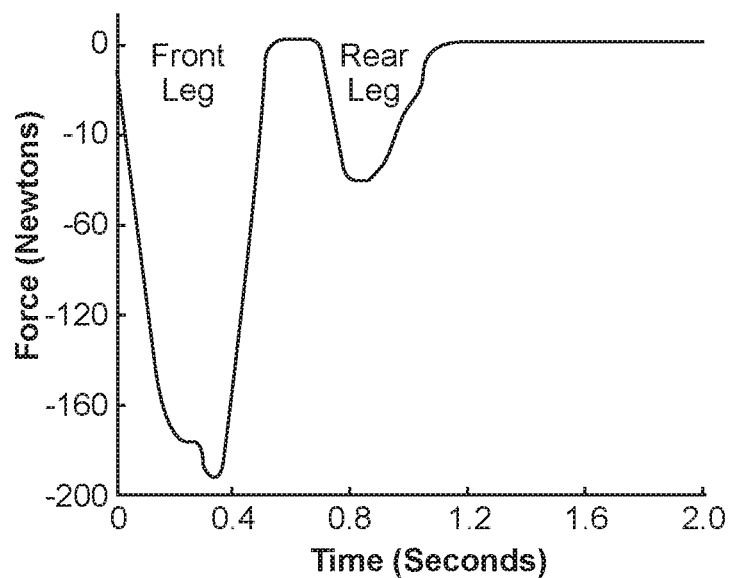
FIG. 62 is a diagram illustrating vertical force exerted at the canine hip during normal gait.
Figure 63:
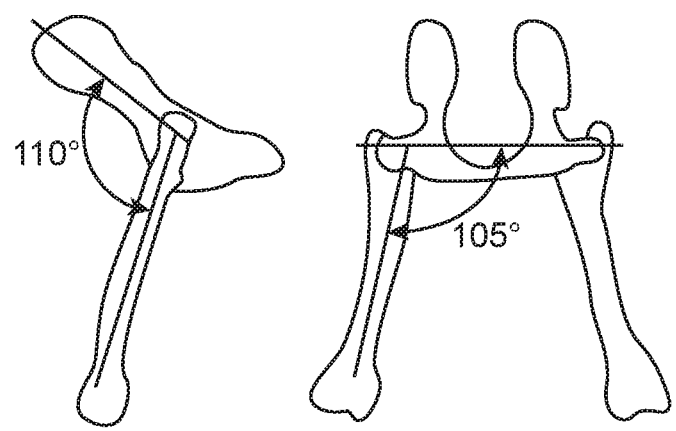
FIG. 63 is a diagram illustrating relative orientation of the femur and pelvis at the stance phase of the gait cycle in a canine hind limb.

In another aspect of the present invention, the principals and teachings may be applied in the veterinary context to the articular joints of animals. One exemplary embodiment of such a veterinary application is the canine hip. The general arrangement of the bones associated with a canine hip, with reference to the hind limb, is illustrated in FIGS. 61A and 61B. As indicated in FIG. 62, force plate studies have shown that the peak vertical force that the rear leg exerts on the floor during the stance phase of a gait cycle varies between 24% and 41% of the total body weight. Dogs place more load on their front legs, between 53% and 65% of their body weight. During the midstance phase of the gait cycle, the orientation of the femur with reference to the pelvis is shown in FIG. 63.

Of particular interest in canine hip dysplasia are the forces acting on the frontal plane (abduction/adduction) during the three legged stance (i.e. with one pelvic limb raised) of the gait cycle. A two dimensional biomechanical model of the canine hip is shown in FIG. 64, in which I represents the ilium; S, the sacrum; H, the femoral head; $F_0$, the force due to gravity; $M_0$, the moment induced by the axial musculature; $F_a$, abductor muscle force; $F_h$, hip reaction force; $\theta_a$, angle of application of $F_a$; $\theta_h$, angle of application of $F_h$.

In a three-legged stance model, the external forces acting on the canine frame must be balanced by the internal forces to achieve equilibrium. External forces include the force $F_0$ exerted by the gravity forces of the trunk and head, and moment (torque) $M_0$ exerted by the twisting forces of the axial musculature. The canine hip joint is subjected to loads greater than the body weight due to additional abductor muscle forces and the pelvic torque. The hip force $F_h$ and the abductor force $F_a$ are directly affected by the femoral neck angle and the abduction/adduction angle of the weight bearing pelvic limb. A large femoral neck angle decreases the distance between the femoral head and the greater trochanter, thus requiring greater abductor muscle forces to overcome the shortened lever arm. This increased muscle force results in an increased hip force. Additionally, the greater the abductor muscle angle $\theta_a$, the greater the hip force angle $\theta_h$. The increased $\theta_h$ results in increased loading of the rim of the acetabulum which results in the degeneration of the acetabular cartilage leading to hip osteoarthritis. A decrease in the femoral neck angle will increase the lever arm distance and thereby decrease both the abductor muscle force $F_a$ and the resultant hip force $F_h$.

Excessive loading of the rim of the acetabulum may also occur when the acetabular coverage of the femoral head is insufficient and the resultant hip force $F_h$ acts closer to the rim of the acetabulum. This occurs when the acetabulum is insufficiently ventroverted.

Surgical interventions to address hip dysplasia involve intertrochanteric osteotomy (ITO) whereby the femoral neck angle is decreased to reduce the hip force or triple pelvic osteotomy (TPO) whereby the acetabular ventroversion is increased. One study analyzing the hip forces after TPO concluded that increasing the ventroversion from 0 degrees to 20 degrees provided the most benefit, while increasing ventroversion from 30 degrees to 40 degrees provided limited benefit. The study also concluded that the beneficial clinical results of TPO may be a result of the reduction in the magnitude of forces acting on the hip joint acting in concert with the increased coverage of the femoral head.

In one exemplary embodiment of the invention, implant 4100 is placed on the femur under the hip abductor muscle complex (e.g. gluteus medius, gluteus profundus etc.) as shown in FIG. 65. In this manner, the force vectors can be altered similar to the biomechanical changes associated with an osteotomy but without the need for such invasive surgery. An implant such as implant 4100 would be appropriate for dogs with large femoral neck angles as well as insufficient acetabular ventroversion.

While implant 4100 may be placed around the area of the greater trochanter, it will be appreciated by persons of ordinary skill in the art that the implant may also be placed in other regions (e.g. femoral neck) so as to achieve the appropriate displacement of the abductor muscles. As shown in FIG. 66, the displacement of the abductor muscles alters the line of action of the abductor muscles. This displacement increases the lever arm of the abductor muscles thereby reducing the abductor muscle force necessary to achieve mechanical equilibrium during the gait cycle, thereby reducing the resultant hip force. Additionally, the change in the abductor muscle angle $\theta_a$ results in altering the resultant hip force angle $\theta_h$, directing in more medially. This change in the direction of the resultant hip force would reduce the load on the rim of the acetabulum as well as potentially improve the stability of the joint.

As with other embodiments described herein, implant 4100 would be designed to not interfere with any of the muscle insertion points in the area of the greater trochanter. As also elsewhere described in conjunction with exemplary embodiments of the present invention, implant 4100 may be attached to the underlying bone using anchors, screws, wires or other means of fixation. The prosthesis may include multiple components, for example, the prosthesis may include an anterior component which is attached to the anterior region of the femur, a posterior component which is attached to the posterior region of the femur, and a third component which is attached to the other two components and effect the displacement of the abductor muscles.

Implant 4100 also could be implanted arthroscopically or using a mini-open or open approach. The thickness of the implant may be adjusted during surgery or anytime after surgery. This could be accomplished by mechanical means. The bearing surface of the implant could be textured or smooth. The surface in contact with bone may be textured or porous to enhance bone in-growth while the surface in contact with the soft tissue may be smooth to enable easy tissue motion.

An exemplary treatment regiment in accordance with an embodiment of the invention is illustrated in FIG. 67. For purposes of illustration, this example is described in the context of a hip treatment, but as will be appreciated by persons of ordinary skill in the art, the process is equally applicable to other locations as taught herein. Beginning at 1000, a plan is made for installation of a prosthesis, such as the prosthesis 220. At 1002, the prosthesis is installed, for example by surgery as described above.

The planning 1000 may involve any number of different regimens. Part of a plan 1000 may involve a particular physician evaluating a hip joint in accordance with well-known procedures, and selecting and installing a particular prosthetic based upon an evaluation. A prosthesis may be selected, for example, from among the many embodiments described herein, or a combination of prostheses may be selected.

As another example of a plan 1000, a computer model of a hip joint H may be generated, permitting a physician to determine, via a visual model of the hip joint, where a prosthesis should be installed and/or to determine what type of prosthesis should be installed. In an embodiment, preoperative images (X-ray, MRI etc.) are used to determine the dimensions of the implant and the optimum location of the implant. Information such the Center-Edge angle of Wiberg, Acetabular Depth ratio, Femoral head extrusion ratio, the Lequense anterior center-edge angle, CCD angle etc. may be used in the analysis. The implant may be selected from a set of standard sizes or an implant that is shaped intra-operatively or a custom implant that has been fabricated to meet the specific patient need.

As another example of planning 1000, a given prosthesis may be the default prosthesis for particular abnormal structures or symptoms of a hip, or may be preferred for particular abnormalities. For example, in an embodiment, implant 220 as described above may be appropriate for patients with a shallow acetabulum A, or with coxa valga. Other prostheses described herein may be more appropriate for other hip abnormalities. Similar planning may be used to treat pathologies of the knee, shoulder, ankle and elbow.

Further alternative exemplary embodiments of the present invention are described in the paragraphs below.

In one example, an apparatus for treating an articular joint, wherein the joint includes at least first and second bones with facing articular surfaces and the bones are subject to forces exerted by target tissues around the joint, comprises a support portion adapted for being secured to tissue or bone, and a bearing portion supported by the support portion. The bearing portion is configured and dimensioned for placement proximate the target tissue. The bearing portion has at least one bearing surface configured to displace the target tissue relative to the joint by a distance sufficient to redirect a force exerted by the target tissue on the joint to achieve a therapeutic effect. Such an exemplary apparatus may also include one or more of the following features:

At least one bearing surface adapted to atraumatically engage target tissue.

The support portion underlies the bearing portion and comprises a support surface opposite the bearing surface adapted to contact underlying tissue.

Attachment means for securing the bearing portion to the underlying tissue.

Constructed of or including a soft compliant material.

Constructed of or including a rigid material.

The support surface adapted to contact at least one of the first and second bones.

Attachment means for securing the support portion to the bone.

Means for securing the implant to soft tissue, which may be configured to secure the implant to the target tissue.

The support portion comprises a support member and the bearing portion comprises a bearing member.

The bearing member is a separate member from the support member.

The support member and bearing member form a single integral structure.

The bearing member is adjustable with respect to the support member to control the displacement of the bearing surface from the support surface.

An adjustment mechanism cooperating between the bearing member and the support member.

The adjustment mechanism comprises a screw adjustment.

The adjustment mechanism is configured to be adjusted after the support surface is secured to the tissue or bone.

The adjustment mechanism comprises a wedge adjustment.

The bearing member is a material different from the support member.

The bearing member is a soft compliant material.

The bearing member is made from a material comprising silicone, titanium, stainless steel or pyrolytic carbon.

The bearing member is configured to provide varying amounts of displacement of the target tissue in response to joint flexion angle.

The bearing member has a ramp shape.

The ramp shape is configured and dimensioned to allow the target tissue to move along the ramp to varying degrees of displacement as the joint is moved through different angles of flexion.

The bearing member defines depressions for receiving and guiding the target tissue.

The implant is configured to displace the target tissue in a first direction generally orthogonal to the bearing surface and in a second direction generally parallel to the bearing surface.

The bearing surface is a low friction material.

The support member has a fixation portion and a displacement portion, with the bearing member being disposed in the displacement portion.

The fixation portion includes means for facilitating fixation to the bone.

The displacement portion is configured and dimensioned to be received around a portion of the greater trochanter or femoral neck, and the fixation portion includes a first part configured and dimensioned to extend anteriorly from the bearing portion between the attachments for the piriformis and gluteus minimus, and to extend posteriorly between the attachments for the quadrates femoris and the iliopsoas.

The fixation portion portion is configured and dimensioned to be received around a portion of the femoral neck, and the displacement portion is configured to extend around at least a portion of a hip abductor muscle to displace the muscle towards the femoral neck.

The support member further comprises a spanning section between the fixation portion and the displacement portion.

The spanning section is configured and dimensioned to avoid select anatomical features located between a fixation location and target tissue displacement location.

The fixation portion is configured and dimensioned to be secured against the femur cranially with respect to the lateral head of the gastrocnemius, the spanning portion is configured and dimensioned to extend posteriorly around the lateral head of the gastrocnemius, and the bearing portion is configured and dimensioned to extend caudally with respect to the lateral condyle and underlie at least one of the fibular collateral ligament and the biceps femoris tendon.

The fixation portion is configured and dimensioned to be secured against the tibia adjacent to Gerdy's tubercle and the soft tissue to be displaced is the iliotibial band, the displacement portion is configured and dimensioned to extend cranially from the tibia to a position proximate the iliotibial band, and the spanning section is configured and dimensioned to extend laterally from the fixation portion to the displacement portion.

The fixation portion is configured and dimensioned to be secured against the tibial tuberacity, the spanning section is configured and dimensioned to extend cranially from the fixation portion, and the displacement portion is configured and dimensioned to extend medially from the spanning section and over a central portion of the tibial condyles proximate the patellar tendon.

In another exemplary embodiment of the present invention, an apparatus for treating an articular joint to effect force distribution in the joint, the joint including at least first and second bones with facing articular surfaces, the bones being positioned with respect to one another by associated muscle and connective tissues, the tissues comprising target tissues for therapy, comprises a bearing member configured and dimensioned for placement in a therapeutic location underlying at least one target tissue, the bearing member having a thickness sufficient to displace the target tissue from its natural path to a therapeutic path when placed in the therapeutic location, and a bearing surface disposed on the bearing member, the bearing surface being configured to atraumatically engage the target tissue and to permit movement of the target tissue there along. Such an exemplary apparatus may also include one or more of the following features:

Dimensions of the bearing member are sufficient to displace target tissues by an amount and in a direction that reduces load on at least a portion of the articular surfaces.

Attachment means for securing the bearing member at the therapeutic location by attachment to surrounding tissue.

A support member supporting the bearing member.

The bearing member is a separate member from the support member.

The bearing member is adjustable with respect to the support member to selectively control displacement of the target tissue.

An adjustment mechanism cooperating between the bearing member and the support member.

The bearing member is a soft compliant material.

The bearing member is configured to provide varying amounts of displacement of the target tissue in response to joint flexion angle.

The bearing member has a ramp shape.

The support member has a fixation portion and a displacement portion, with the bearing member being disposed in the displacement portion.

The support member further comprises a spanning section between the fixation portion and the displacement portion.

The spanning section is configured and dimensioned to avoid select anatomical features located between a fixation location and target tissue displacement location.

A support surface disposed on the support member opposite the bearing member, the support surface being configured and dimensioned to support the bearing member against tissue underlying the target tissue.

The support surface is adapted to contact another target tissue.

The support surface is adapted to contact at least one of the first and second bones for support thereon.

In a further exemplary embodiment of the present invention, an apparatus for treating disorders of articular joints, the joint being subject to forces exerted by soft tissues disposed proximate to the joint, comprises a prosthesis implantable in engagement with the soft tissues so as to displace the soft tissues sufficiently to alter the location, angle or magnitude of the forces exerted by the soft tissues so as to achieve a therapeutic effect in the joint. Such an exemplary apparatus may also include one or more of the following features:

The articular joint is a hip joint and the prosthesis is configured and dimensioned to counter forces acting to create a dysplastic joint, wherein the wherein the hip joint is a human hip joint or a canine hip joint.

The articular joint is a knee joint and the prosthesis is configured and dimensioned to counter forces acting to create an osteoarthritic joint and/or to counter forces acting to create excessive patellar compression force.

The prosthesis comprises anchoring means for anchoring the prosthesis in a fixed position relative to at least a portion of the joint.

The prosthesis displaces the soft tissues in a first direction away from the base tissue and in a second direction laterally relative to the base tissue.

The joint is surrounded by a capsule, and wherein the anchoring means is configured for fastening to soft tissue or bone outside of the capsule.

The prosthesis is a hard material.

The prosthesis comprises a soft outer layer defining a chamber and wherein the chamber is filled with a fluid or gel.

The prosthesis comprises a connector for filling the chamber with the fluid or gel after the prosthesis is implanted.

The prosthesis is bifurcated so as to have a wishbone, Y or V shape.

The prosthesis is configured to be mounted over the greater trochanter or femoral neck.

The prosthesis is configured to be mounted over the femoral lateral condyle.

The prosthesis is configured to be mounted to at least one of the femur, pelvis, fibula, tibia, radius, ulna scapula, calcaneus, humerus, spinal vertebrae, tarsal, metatarsal, carpal, metatarsal, or talus.

The prosthesis is configured to be mounted to the tibia adjacent to Gerdy's tubercle and the soft tissue to be displaced is the iliotibial band.

The prosthesis is configured to be mounted to the tibial tuberacity and the soft tissue to be displaced is the patellar tendon.

In yet another exemplary embodiment of the present invention, a method of treating an articular joint to effect force distribution in the joint, the joint including at least first and second bones with facing articular surfaces, the bones being positioned with respect to one another by associated muscle and connective tissues, comprises selecting at least one of the associated muscle and connective tissues as target tissue for treatment, displacing the target tissue without severing the bones or target tissue, and redistributing loading in the joint to achieve a therapeutic affect by the displacing. Such an exemplary method may also include one or more of the following features or steps:

The displacing is in a direction away from the joint.

The displacing comprises placing an implant under the target tissue.

The implant comprises a biocompatible member having a thickness corresponding to a selected tissue displacement.

The placing comprises inserting the implant under the target tissue at a therapeutically effective location, and securing the implant at the therapeutically effective location without substantial restriction of movement of the target tissue.

The joint is a knee and the target tissue is located and displaced laterally with respect to the knee.

The securing comprises attaching the implant to the target tissue.

The securing comprises attaching the implant to a soft tissue underlying the target tissue.

The securing comprises attaching the prosthesis to a bone underlying the target tissue.

The securing comprises attaching the prosthesis to a supporting tissue by suture, screw, staple, adhesive, or band.

The supporting tissue is at least one of the target tissue, a soft tissue underlying the target tissue, bone underlying the target tissue.

The natural force exerted by the target tissue acts on the joint through an effective moment arm, and displacing the target tissue moves the target tissue to a position wherein the effective moment arm is increased.

The effective moment arm is increased by about 10 mm to about 30 mm.

The increase in effective moment arm is sufficient to increase torque by about 20% to about 30%.

The target tissue is an iliotibial tract.

The target tissue is a lateral quadriceps-patellar tendon.

The target tissue is a biceps femoris muscle.

The target tissue is a biceps femoris tendon.

The target tissue is a popliteus muscle.

The target tissue is a lateral gastrocnemius muscle.

The target tissue is one or more abductor muscles.

The joint is the hip and the target tissue is at least one abductor muscle, which may include one or more of the gluteus minimus, gluteus medius and/or gluteus maximus.

The joint is the knee and the target tissue is displaced anteriorly, the target tissue being one or both of the patellar tendon and or the iliotibial band.

Altering the target tissue displacement in response to joint flexion angle.

In a further exemplary embodiment of the present invention, a method of treating an articular joint, the joint including at least first and second bones with facing articular surfaces, the bones being subject to a force exerted by target tissues around the joint, comprises implanting a prosthesis to displace the target tissue relative to the joint, wherein a force exerted by the target tissue is redirected in a manner to redistribute a load on at least one of the articular surfaces without cutting the first or second bones. Such an exemplary method may also include one or more of the following features or steps:

The target tissue is displaced laterally, anteriorly or posteriorly relative to the joint.

The prosthesis is implanted on the same side of the joint as the target tissue.

Adjusting the magnitude of displacement of the target tissue after the prosthesis is implanted.

The joint is a knee, and the prosthesis is implanted on a first side of the knee to reduce loading on the articular surface of a second side of the knee. The first side may be the lateral side and the second side may be the medial side.

The joint is a knee, and the prosthesis is implanted on the tibia to reduce loading on the femur.

The joint is the hip, and the prosthesis is implanted on a first side of the hip to move a resultant force in the joint away from the first side. The first side may be the lateral side The hip may be a human or canine hip.

The force exerted by the target tissue acts through a moment arm prior to displacing the target tissue and the target tissue is displaced to substantially increase the moment arm.

The force exerted by the target tissue opens the joint on a side opposite the target tissue.

In yet another exemplary embodiment of the present invention, a method of treating an articular joint, the joint including at least first and second bones with facing articular surfaces, the bones being subject to forces exerted by target tissues around the joint, comprises creating a surgical opening to access the target tissue, displacing the target tissue relative to the joint into a displaced configuration to redirect a force exerted on the joint by the target tissue without cutting the first or second bone, and closing the surgical opening with the target tissue remaining in the displaced configuration. The displacing may comprise positioning a prosthesis under the target tissue.

In a further exemplary embodiment of the present invention, a method for treating a hip joint having hip abductor muscles acting hereon, comprises installing a prosthesis in engagement with at least a portion of the hip abductor muscles or connective tissue connected thereto to alter a force vector applied by the hip abductor muscles to the hip joint. Such an exemplary method may also include one or more of the following features or steps:

The prosthesis is installed without cutting bone associated with the hip joint.

The hip joint has a hip capsule and the prosthesis is installed superficial to the hip capsule.

The prosthesis displaces the hip abductor muscles to alter the force vector.

The displacement of the hip abductor muscles is lateral.

The displacement of the hip abductor muscles is anterior or posterior.

The prosthesis alters the angle of the force vector relative to the hip joint.

Installing comprises installing the prosthesis between gluteus muscles and capsular ligaments that surround the hip joint.

Installing comprises inserting the prosthesis in an evacuated state and filling the prosthesis with a fluid.

Installing comprises inserting a bag having an inlet, and filling the bag with a curable material and allowing the curable material to harden.

The prosthesis includes a feature for guiding at least one of muscles and tendons, and wherein installing comprises aligning the one of muscles and tendons with the feature.

Anchoring the prosthesis to a pelvis and/or femur of the patient.

Anchoring the prosthesis to a femoral neck of the patient.

Installing comprises installing the prosthesis transverse to the femoral neck.

Installing comprises nesting the prosthesis around the femoral neck of the patient.

Installing comprises inserting the prosthesis in a contracted state and expanding the prosthesis in situ into an expanded state.

Installing comprises inserting the prosthesis in a contracted state, installing the prosthesis in the contracted state and expanding the prosthesis in situ into and expanded state.

Installing comprises assembling two or more parts to form the prosthesis, each part expanded in situ.

Installing comprises injecting a fluid into the hip joint and allowing the fluid to harden into the prosthesis.

Installing comprises attaching the prosthesis to soft tissue proximate the hip joint.

The prosthesis is attached to at least a portion of the hip abductor muscles or connective tissue attached thereto.

Installing comprises extending a belt or strap around at least a portion of the hip abductor muscles and tightening the belt or strap around the at least a portion of the hip abductor muscles to alter the force vector applied by the hip abductor muscles.

The belt or strap draws the at least a portion of the hip abductor muscles toward the femoral neck.

Treating a hip joint comprises treating a hip joint of a human or a non-human animal.

Computer aided planning to prepare prosthesis shape and location.

Preparing the prosthesis shape inter-operatively.

In yet a further exemplary embodiment of the present invention, a method for treating a hip joint having hip abductor muscles acting thereon, comprises installing a prosthesis in engagement with a greater trochanter of the hip joint to alter a force vector applied by the hip abductor muscles to the hip joint. Such an exemplary method may also include one or more of the following features or steps:

The prosthesis is mounted on the greater trochanter of the patient to form a cap over the greater trochanter.

Installing comprises inserting the prosthesis in a contracted state and expanding the prosthesis in situ into an expanded state.

Installing comprises assembling two or more parts to form the prosthesis, wherein each part may have a pair of movable legs, the legs being collapsible for introduction and expandable for installation.

Installing comprises placing the prosthesis in a delivery device in a collapsed form, and releasing the prosthesis from the delivery device in an expanded form.

Installing comprises articulating a pair of hinged legs of the prosthesis from a collapsed configuration to an expanded configuration.

In another exemplary embodiment of the present invention, a method for treating a knee joint having connective tissues including an iliotibial band, a biceps femoris, a collateral fibular ligament, and a patellar tendon acting thereon, comprises installing a prosthesis in engagement with at least a portion of one of the connective tissues to alter a force vector applied by the connective tissues to the knee joint. Such an exemplary method may also include one or more of the following features or steps:

The prosthesis is installed without cutting bone associated with the knee joint.

The knee joint has a joint capsule and the prosthesis is installed superficial to the joint capsule.

The prosthesis displaces the at least one of the connective tissues to alter the force vector.

The displacement of the connective tissues is lateral and/or anterior.

The prosthesis alters the angle of the force vector relative to the knee joint.

The connective tissue is the iliotibial band and the prosthesis displaces the iliotibial band in the lateral direction.

The connective tissue is the biceps femoris and the prosthesis displaces the biceps femoris in the lateral direction.

The connective tissue is the collateral fibular ligament and the prosthesis displaces the collateral fibular ligament in the lateral direction.

The connective tissue is the patellar tendon and the prosthesis displaces the patellar tendon in the anterior direction.

In a further exemplary embodiment of the present invention, a method of treating inflammation or pain due to rubbing or pressure of soft tissue against other tissue, comprises implanting a prosthesis proximate the soft tissue wherein the prosthesis displaces the soft tissue sufficiently to reduce the inflammation or pain. Such an exemplary method may also include one or more of the following features or steps:

The prosthesis displaces the soft tissue in a manner which reduces the pressure of the soft tissue against the other tissue.

The soft tissue is the iliotibial band.

The other tissue is the lateral femoral epicondyle.

The prosthesis is implanted between the tibia and iliotibial band to displace the iliotibial band laterally or anteriorly.

Securing the prosthesis to the tibia.

The prosthesis is secured to the tibia adjacent Gerdy's tubercle.

While the invention has been illustrated by examples in various contexts of treating human and animal osteoarthritis and dysplasia associated with force imbalances in a joint, it will be understood that the invention may also have application to treatment of focal defects caused by trauma or other reasons. In particular, pain associated with focal defects in the medial condyle in the knee may be reduced by applying the devices and methods of the invention to reduce loading on the medial condyle.

Other applications of devices and methods of the invention include use in conjunction with meniscal repair treatment to reduce loading on the medial condyle. The contoured bearing surface for the iliotibial band could also alleviate pain associated with the iliotibial band friction syndrome. Another application includes use in conjunction with total hip replacement devices to alter the mechanical forces on the new joint, thereby increasing the stability of the replaced joint and reducing the risk of implant wear. The invention may further be adapted to displace tissues acting on various other joints so as to reduce or otherwise alter loads therein, including the elbow, shoulder, wrist, fingers, spine, ankle, interphalangeal joints, jaw or other joints. For example, the implants of the invention may be configured for attachment to the acetabulum, vertebrae of the spine, scapula, humerus, radius, ulna, carpals, metacarpals, tarsals, metatarsals, talus or other bones of the foot, among other bones.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A method for treating a human hip joint having hip abductor muscles acting thereon, comprising:
   implanting a prosthesis in engagement with at least a portion of the hip abductor muscles or connective tissue connected thereto to alter a force vector applied by the hip abductor muscles to the hip joint.

2. The method of claim 1, wherein the prosthesis is implanted without cutting bone associated with the hip joint.

3. The method of claim 1, wherein the hip joint has a hip capsule and the prosthesis is implanted outside the hip capsule.

4. The method of claim 1, wherein the prosthesis displaces the hip abductor muscles to alter at least one of the force vector or an angle of the force vector relative to the hip joint.

5. The method of claim 4, wherein the displacement of the hip abductor muscles is in a circumferentially outward direction with respect to the hip joint.

6. The method of claim 1, wherein implanting comprises installing the prosthesis between gluteus muscles and capsular ligaments that surround the hip joint.

7. The method of claim 1, wherein implanting comprises assembling at least two interlocking parts to form the prosthesis.

8. The method of claim 1, wherein said implanting comprises securing the prosthesis to an outer surface of the femur in between muscle attachment points on an upper portion of the femur.

* * * * *